United States Patent
Yanai et al.

(10) Patent No.: US 6,255,286 B1
(45) Date of Patent: Jul. 3, 2001

(54) DEPSIPEPTIDES AND DRUGS CONTAINING THE SAME AS THE ACTIVE INGREDIENT

(75) Inventors: Makoto Yanai; Masashi Suzuki; Norio Oshida; Koji Kawamura; Shigeru Hiramoto; Orie Yasuda; Nobuhiro Kinoshita; Akiko Shingai; Masako Takasu, all of Saitama-ken (JP)

(73) Assignee: Nisshin Flour Milling Co., Ltd., Tokyo (JP)

(*) Notice: Subject to any disclaimer, the term of this patent is extended or adjusted under 35 U.S.C. 154(b) by 0 days.

(21) Appl. No.: 09/214,002

(22) PCT Filed: Jun. 25, 1997

(86) PCT No.: PCT/JP97/02195

§ 371 Date: Dec. 24, 1998

§ 102(e) Date: Dec. 24, 1998

(87) PCT Pub. No.: WO97/49722

PCT Pub. Date: Dec. 31, 1997

(30) Foreign Application Priority Data

Jun. 25, 1996 (JP) ........................................ 8-183960

(51) Int. Cl.$^7$ ........................... A61K 38/00; A61K 38/05; A61K 38/06; A61K 38/07
(52) U.S. Cl. .......................... 514/19; 514/18; 530/330; 530/331; 530/333; 530/323
(58) Field of Search ................................. 514/16, 18, 19; 530/330, 331, 333, 323

(56) References Cited

U.S. PATENT DOCUMENTS 5,801,143   9/1998   Hiramoto et al. .

OTHER PUBLICATIONS

Shin et al., "Phase I/II Clinical Trial of Didemnin B in Non–Small–Cell Lung Cancer: Neuromuscular Toxicity is Dose–Limiting", Cancer Chemother Pharmacol, 29:145–149, 1991.*

Morrison, J.D. et al., The synthesis of norsurfactin, a hemolytic, anticoagulant cyclodepsipeptide., Tetrahedron Letters, 1976, No. 21, (pp. 1773–1776).

Hardy, P.M. et al. Polypeptides. Part XXV, Synthesis of Isariin, J. Chem. Soc. Perkin Trans. I, 1974, No. 7, (pp. 802–808).

Michael J. Ignatius, et al. "Expression of apolipoprotein E during nerve degeneration and regeneration", Proc. Natl. Acad. Sci. USA, vol. 83. (pp. 1125–1129), Feb. 1986.

Nobuhiro Yamada, et al. "Increased clearance of plasma cholesterol after injection of apolipoprotein E into Watanabe heritable hyperlipidemic rabbits", Proc. Natl. Acad. Sci. USA, vol. 86, Jan. 1989, (pp. 665–669).

Hitoshi Shimano, et al. "Plasma Lipoprotein Metabolism in Transgenic Mice Overexpressing Apolipoprotein E", The American Society for Clinical Investigation, Inc., vol. 90, Nov. 1992 (pp. 2084–2091).

* cited by examiner

*Primary Examiner*—F. T. Moezie
(74) *Attorney, Agent, or Firm*—Oblon, Spivak, McClelland, Maier & Neustadt, P.C.

(57) ABSTRACT

Depsipeptides represented by the formula (1):

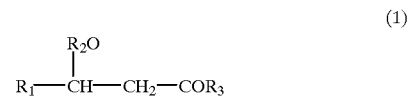

(wherein:

$R_1$ is a straight or branched alkyl group of 5–20 carbon atoms or a straight or branched alkoxymethyl group of 5–15 carbon atoms; $R_2$ is —A—B, —A—B—W, —A—B—W—D or —A—B—W—D—E, $R_3$ is a hydroxyl group, a lower alkoxy group, a benzyloxy group, —Z, —Z—G or —Z—G—J, the above A, B, D, E, G and J independently each other are a residue of an amino acid selected from alanine, valine, leucine, isoleucine, serine, threonine, lysine, hydroxylysine, arginine, cysteine, methionine, phenylalanine, tyrosine, aspartic acid, asparagine, glutamic acid, glutamine and the like or an N—($C_1$–$C_4$) alkyl derivative of these amino acid residues; the above W and Z independently each other are a residue of an amino acid selected from aspartic acid, asparagine, glutamic acid, glutamine, alanine, serine or lysine) or pharmacologically acceptable salts thereof.

The depsipeptides have an activity of promoting the production of apolipoprotein E and are useful as a therapeutic agent for neurologic damages, especially for dementia, and further as a therapeutic agent for hyperlipemia.

10 Claims, No Drawings

US 6,255,286 B1

DEPSIPEPTIDES AND DRUGS CONTAINING THE SAME AS THE ACTIVE INGREDIENT

TECHNICAL FIELD

This invention relates to a novel depsipeptide and a pharmaceutical preparation containing the same as an active ingredient. The depsipeptides of the invention have a promoting activity on the production of apolipoprotein E, and they are useful as a therapeutic agent for neurologic damages, especially for dementia, and also as a therapeutic agent for hyperlipemia.

BACKGROUND ART

As a therapeutic agent for senile dementia, there have been mainly applied activators of cerebral circulation and metabolism, but these drugs have no improving effect on disintegration of the central nervous system which is believed to cause senile dementia. Consequently, they possess no improving effect on dysmnesia and acalculia which are said to be central symptoms of dementia. In view of the above, there has been desired a new therapeutic agent for senile dementia which promotes the repair and growth of nervous systems while inhibiting the disintegration of the central nervous system.

On the other hand, it was reported that apolipoprotein E may be generated at a high level at the sites of nervous systems which were damaged and are being repaired (For example, refer to M. J. Ignatius et al., Proc. Natl. Acad. Sci. U.S.A., 83, 1125 (1986)), which suggests that apolipoprotein E will play an important role in repairing nervous systems. Moreover, it has recently been reported that a remarkable reduction in a plasma cholesterol level can be observed by intravenous administration of apolipoprotein E to WHHL rabbit, which is a model animal for human familial hypercholesterolemia homozygote (Yamada et al., Proceeding of National Academy Science USA, Vol. 86, pp. 665–669, 1989). Also, it has been reported that plasma cholesterol and plasma triglyceride can be noticeably decreased by transducing a gene for apolipoprotein E into the mouse liver and expressing apolipoprotein E in a large mass (Shimano, H. et al., Journal of Clinical Investigation, Vol. 90, pp. 2084–2091, 1992).

As is apparent from these reports, the increase in plasma apolipoprotein E concentration has been regarded as extremely effective for the treatment of hyperlipemia, especially, familial hypercholesterolemia homozygote which has been hitherto considered as difficult to be treated with the prior art drugs.

DISCLOSURE OF THE INVENTION

The present invention relates to a depsipeptide represented by the formula (1):

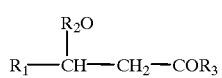

(wherein:
$R_1$ is a straight or branched alkyl group of 5–20 carbon atoms or a straight or branched alkoxymethyl group of 5–15 carbon atoms; $R_2$ is —A—B, —A—B—W, —A—B—W—D or —A—B—W—D—E, $R_3$ is a hydroxyl group, a lower alkoxy group, a benzyloxy group, —Z, —Z—G or —Z—G—J, said A, B, D, E, G and J independently each other are a residue of an amino acid selected from alanine, valine, leucine, isoleucine, serine, threonine, lysine, hydroxylysine, arginine, cysteine, methionine, phenylalanine, tyrosine, tryptophan, histidine, proline, 4-hydroxyproline, piperizine-4-carboxylic acid, homoproline, octahydroindole-2-carboxylic acid, norvaline, norleucine, α-t-butylglycine, cyclohexylglycine, azetidine-2-carboxylic acid, 3-(3-pyridyl)alanine, (3-N-methyl)piperizylalanine, 3-(2-naphthyl)alanine, β-cyclohexylalanine, β-t-butylalanine, 9-anthracenylalanine, α-methylalanine, 2-aminobutanoic acid, aspartic acid, asparagine, glutamic acid and glutamine or an N—($C_1$–$C_4$) alkyl derivative of said amino acid residue; W and Z independently each other are a residue of an amino acid selected from aspartic acid, asparagine, glutamic acid, glutamine, alanine, serine or lysine; and wherein a free amino group, a free carboxyl group or a free ω-carbamido group of said amino acid residue and/or an N-terminal amino group may be protected by a protecting group commonly used in peptide chemistry, and when said amino acid residue in the above A, B, D, E, G, J, W and Z is a residue of lysine, hydroxylysine, glutamic acid or aspartic acid, the amino group or carboxyl group capable of being bound to an adjacent amino acid by peptide linkage may be located at either the α-position or the ω-position) or a pharmacologically acceptable salt thereof.

The present invention also relates to pharmaceutical preparations, an agent for promoting the production of apolipoprotein E, therapeutic agents for neurologic damages, dementia and hyperlipemia, which contains as an active ingredient a depsipeptide represented by the above formula (1) or a pharmacologically acceptable salt thereof.

The invention also relates to a method for the promotion of the production of apolipoprotein E, a method for the treatment of neurologic damages or a method for the treatment of dementia, which comprises administering a depsipeptide represented by the above formula (1) or a pharmacologically acceptable salt thereof.

The invention also relates to a method for the treatment of hyperlipemia, which comprises administering a depsipeptide represented by the above formula (1) or a pharmacologically acceptable salt thereof.

In the above formula (1), it is preferable that A, B, D, E, G and J independently each other are alanine, valine, leucine, isoleucine, phenylalanine, tyrosine, proline, β-t-butylalanine or aspartic acid, and W and Z independently each other are aspartic acid, asparagine, glutamic acid, glutamine, alanine, serine or lysine.

It is more preferable that A is isoleucine, alanine or aspartic acid, B is leucine, phenylalanine, β-t-butylalanine or aspartic acid, D is valine, phenylalanine, alanine or aspartic acid, E is leucine or alanine, G is leucine or alanine, J is leucine or alanine, W is aspartic acid, glutamic acid, asparagine, glutamine or serine and Z is aspartic acid, glutamic acid, asparagine, glutamine or lysine.

It is still more preferable that A is isoleucine or alanine, B is leucine or alanine, D is valine or alanine, E is leucine, alanine or glutamic acid, G is leucine or alanine, J is leucine or alanine, W is asparagine or glutamic acid and Z is glutamine, asparagine, glutamic acid, aspartic acid or lysine.

It is particularly preferable that A is isoleucine, B is leucine, D is valine, E is leucine, G is leucine, J is leucine, W is aspartic acid or glutamic acid and Z is glutamine, asparagine, glutamic acid, aspartic acid or lysine.

In the above formula (1), $R_1$ is preferably a straight alkyl or alkoxymethyl group of 6–12 carbon atoms.

The above-recited amino acids which compose the depsipeptides having the formula (1) of the invention may be either L-isomers or D-isomers, while the amino acids represented by A, D, G, J, W and Z are preferably L-isomers and the amino acid represented by B and E are preferably D-isomers. A protecting group for the free amino groups in said amino acid residues includes, for example, a t-butoxycarbonyl (hereinafter referred to as "Boc") group, a benzyloxycarbonyl group (hereinafter referred to as "Cbz"), a p-methoxy-benzyloxycarbonyl group or a 9-fluorenylmethoxycarbonyl group (hereinafter referred to as "Fmoc") or the like, a protecting group for the free carboxyl groups in said amino acid residues includes a benzyloxy group (hereinafter referred to as "Obzl") or a t-butoxy group (hereinafter referred to as "OtBu") or the like, and a protecting group for ω-carbamido groups in Gln or Asn includes 4,4'-dimethoxybenzhydryl (hereinafter referred to as "Mbh") group or the like.

As a protecting group for the N-terminal amino group in said depsipeptide, there may be used those conventionally employed in peptide chemistry, such as a Boc group, a Cbz group, a p-methoxybenzyloxycarbonyl group, a Fmoc group and the like.

As a protecting group for the C-terminal carboxy group in said depsipeptide, there may be used an OBzl group, an OtBu group and the like.

The depsipeptides of the above formula (1) have an action of promoting the production of apolipoprotein E in Hep G2 cells, which possess various functions of the liver. Apolipoprotein E has an action of repairing neurologic damages and also an action of lowering blood cholesterol and triglyceride levels. Therefore, the depsipeptides of the invention which may promote the production of apolipoprotein E are useful as a therapeutic agent for neurologic damages, especially dementia, or for hyperlipemia.

The depsipeptides represented by the above formula (1) or pharmacologically acceptable salts thereof may be prepared according to any methods conventionally employed for peptide synthesis. For example, there may be employed a process with a condensing agent, a process with an azide, a process with an acid chloride, a process with an acid anhydride, a process with an active ester, a process by redox, a process by an enzyme or the like as disclosed in Nobuo Izumiya et al., "Fundamentals and Experiments for Peptide Synthesis (in Japanese)", issued by Maruzen Co., Ltd., 1985.

The depsipeptides of the invention or pharmacologically acceptable salts thereof can be prepared, for example, by protecting or activating the carboxyl group or hydroxyl group of 3-hydroxycarboxylic acid represented by the formula (2)

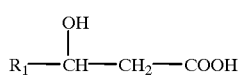

(2)

(wherein $R_1$ is as defined above) and then condensing the resulting product successively with the desired amino acids according to a conventional method.

The protection of the carboxyl group in the compound of the above formula (2) may be carried out according to esterification for methyl esters by reacting the compound with diazomethane in a solvent such as ether, methanol or the like under ice-cooling or at a room temperature or esterification for benzyl esters by reacting the compound with benzyl bromide in the presence of a basic substance such as triethylamine in a solvent such as dimethylformamide (hereinafter referred to as "DMF"), dimethyl sulfoxide (hereinafter referred to as "DMSO") or the like at a temperature of from room temperature to heating temperature.

The condensation of an amino acid with the hydroxyl group in a compound having the protected carboxyl group may be carried out using as a condensing agent N,N'-dicyclohexylcarbodiimide (hereinafter referred to as "DCC") or 1-ethyl-3-(3'-dimethylaminopropyl) carbodiimide hydrochloride, i.e. water-soluble carbodiimide (hereinafter referred to as "WSCI") or the like in a solvent such as ether, acetone, chloroform, dichloromethane, ethyl acetate, DMF, tetrahydrofuran (hereinafter referred to as "THF"), acetonitrile, DMSO or the like under ice-cooling or at room temperature, preferably in the presence of an acylation catalyst such as dimethylaminopyridine (hereinafter referred to as "DMAP") or the like.

As the 3-hydroxycarboxylic acid of the formula (2), which is a starting material of the depsipeptide of the invention, there may be illustratively mentioned 3-hydroxy-capric acid, 3-hydroxy-pelargonic acid, 3-hydroxy-capric acid, 3-hydroxy-lauric acid, 3-hydroxy-myristic acid, 3-hydroxy-palmitic acid, 3-hydroxy-margaric acid and 3-hydroxy-stearic acid.

In preparing the depsipeptide of the above formula (1) by the process with a condensing agent, it is preferable to use DCC or WSCI. It is also preferable to simultaneously add additives commonly used to prevent racemization such as N-hydroxysuccinimide, N-hydroxybenzotriazole (hereinafter referred to as "HOBt"), N-hydroxy-5-norbornene-2,3-dicarbodiimide, benzotriazole and the like.

Main condensing agents which may be employed in the azide process include diphenylphosphoric acid azide (hereinafter referred to as "DPPA"), diethylphosphoric acid cyanide and the like.

Prior to the condensation reaction, it is preferable to apply any known protection procedures to the carboxyl group, amino group, ω-carbamido group and the like which do not participate in the reaction.

The protecting group which can be used for the protection procedure is any of the afore-mentioned ones.

Removal of the protecting group during the preparation of the depsipeptide of the invention should be carried out without influencing the peptide bond and may be well-chosen depending upon the type of the protecting group used.

The solvent which may be employed in individual peptide synthesis as mentioned above includes, for example, anhydrous or hydrous chloroform, dichloromethane, ethyl acetate, DMF, DMSO, pyridine, dioxane, THF, dimethoxyethane, acetonitrile and the like, and they may be used in combination with two or more thereof, if necessary. The condensation reaction may be carried out at a temperature ranging from about −20 to 50° C. as usually employed.

Peptide synthesis may be carried out according to any of liquid phase method and solid phase method, while column method or batch method may be also applicable.

When the depsipeptides of the invention are in the form of salts thereof, they may be converted to the corresponding free form, and the thus obtained depsipeptides in the free form may be converted to the corresponding pharmacologically acceptable salts thereof. In the latter case, when the depsipeptide is in the form of an acidic compound because of the presence of carboxyl group, there may be formed salts with inorganic bases such as sodium, potassium, calcium and ammonium salts or the like and with organic bases such as triethylamine salt, and when the peptide derivative is in the form of a basic compound because of the presence of the amino group, there may be formed salts with inorganic acids such as hydrochloric acid, hydrobromic acid, sulfuric acid and phosphoric acid or the like and with organic acids such as acetic acid, succinic acid, oxalic acid, malic acid, tartaric acid or the like.

The depsipeptides or pharmacologically acceptable salts thereof according to the invention can be formulated into pharmaceutical preparations of various dosage forms. More specifically, such pharmaceutical preparations may be administered orally in the forms of solid preparations such as tablets, hard capsules, soft capsules, granules, powders, etc. and in the forms of liquid preparations such as solutions, emulsions, suspensions, etc. They may be also administered parenterally in the forms of injections, suppositories, etc.

In preparing such pharmaceutical preparations, conventional additives may be added, for example, excipients, stabilizers, antiseptics, solubilizing agents, wetting agents, emulsifying agents, lubricants, sweetening agents, coloring agents, flavoring agents, isotonic agents, buffering agents, antioxidants and the like.

As the additives, there may be mentioned, for example, starch, sucrose, fructose, lactose, glucose, mannitol, sorbitol, precipitated calcium carbonate, crystalline cellulose, carboxymethylcellulose, dextrin, gelatin, acacia, magnesium stearate, talc, hydroxypropylmethylcellulose and the like.

Where the depsipeptides of the invention are to be applied in the form of solutions or injections, they may be dissolved or suspended in any conventional diluent. The diluent includes, for example, physiological saline, Ringer's solution, an aqueous glucose solution, alcohols, fatty acid esters, glycols, glycerols, oils and fats derived from plant or animal sources, paraffins and the like.

These preparations may be prepared according to any conventional method.

A usual clinical dose may be in the range of 1–2000 mg per day for adult when orally given. More preferably, it is in the range of 5–1000 mg.

The preparation of the present depsipeptides will be illustratively explained hereinafter by way of Referential Examples and Examples, while the apolipoprotein E productivity of the present depsipeptides will be illustratively explained by way of Test Examples and Preparation Examples.

EXAMPLE

The synthesis of the compounds of the invention will be explained hereinafter by way of Referential Examples and Examples, but the invention is not to be limited thereto. In the following Referential Examples and Examples, where the amino acid forming the depsipeptide is in the form of D-isomer, it shall be specifically indicated, and unless otherwise specified the amino acid shall be in the form of L-isomer. The reaction schemes in Referential Examples and Examples will be illustrated by Schemes 1–40.

Referential Example 1
Preparation of Intermediate (1)

To a solution of 5.00 g of 3-hydroxymyristic acid in 50 ml of DMF were added at room temperature 2.85 ml of triethylamine and 2.43 ml of benzyl bromide. The reaction mixture was stirred at room temperature overnight. The solvent was concentrated under reduced pressure, ethyl acetate and water were added to the residue, the organic layer was separated and washed twice with water and dried over anhydrous sodium sulfate. After the solvent was removed in vacuo, the crude product was subjected to column chromatography using silica gel and eluted with chloroform: methanol= 100:0–10 to afford 3.69 g of Intermediate (1).

$^1$H-NMR ($\delta$ ppm, CDCl$_3$) 7.33–7.40 (m, 5H), 5.16 (s, 2H), 3.95–4.05 (m, 1H), 2.85 (d, J=4.4 Hz, 1H), 2.56 (dd, J=2.9, 17 Hz, 1H), 2.46 (dd, J=9.0, 17 Hz, 1H), 1.20–1.60 (m, 20H), 0.88 (t, J=6.8 Hz, 3H)

Referential Example 2
Preparation of Intermediate (2)

To a solution of 3.00 g of Intermediate (1) in 25 ml of dichloromethane were added in turn under ice-cooling 2.22 g of t-butoxycarbonyl-L-isoleucine, 77 mg of 4-dimethylaminopyridine and 2.78 g of DCC dissolved in 25 ml of dichloromethane. The reaction mixture was stirred under ice-cooling for one hour and then at room temperature for 2 hours. The precipitates thus separated was filtered off, the filtrate was washed in turn with 0.5N hydrochloric acid, saturated aqueous sodium hydrogencarbonate and saturated aqueous sodium chloride, and dried over anhydrous sodium sulfate. After the solvent was removed in vacuo, the crude product was subjected to column chromatography using silica gel (100 g) and eluted with hexane:ethyl acetate= 200:0–15 to afford 4.62 g of Intermediate (2) as a colorless oily substance.

$^1$H-NMR ($\delta$ ppm, CDCl$_3$) 7.30–7.39 (m, 5H), 5.24–5.33 (m, 1H), 5.12 (s, 1H), 5.10 (d, J=2.5 Hz, 1H), 4.98–5.05 (m, 1H), 4.15–4.25 (m, 1H), 2.56–2.72 (m, 2H), 1.75–1.90 (m, 1H), 1.50–1.70 (m, 2H), 1.20–1.45 (m, 19H), 1.44 (s, 9H), 1.10–1.20 (m, 1H), 0.86–0.93 (m, 9H)

Using the same procedures as described above, the following compounds were prepared:

Intermediate (5)
$^1$H-NMR ($\delta$ ppm, CDCl$_3$) 5.20–5.30 (m, 1H), 4.95–5.05 (m, 1H), 4.23 (br s, 1H), 3.67 (2s, 3H), 2.51–2.68 (m, 2H), 1.70–1.90 (m, 1H), 1.50–1.70 (m, 2H), 1.44 (s, 9H), 1.10–1.50 (m, 20H), 0.85–0.95 (m, 9H)

Intermediate (11)
$^1$H-NMR ($\delta$ ppm, CDCl$_3$) 7.25–7.35 (m, 5H), 7.10–7.15 (m, 4H), 6.80–6.90 (m, 4H), 6.07 (s, 1H), 5.15–5.30 (m, 1H), 4.95–5.10 (m, 2H), 4.20–4.30 (m, 1H), 4.05–4.15 (m, 1H), 3.74–3.76 (m, 6H), 2.15–2.55 (m, 4H), 2.05–2.15 (m, 1H), 1.75–1.95 (m, 2H), 1.50–1.65 (m, 2H), 1.45 (s, 9H), 1.10–1.50 (m, 20H), 0.80–0.95 (m, 9H)

Intermediate (78)
$^1$H-NMR ($\delta$ ppm, CDCl$_3$) 7.76 (d, J=7.3 Hz, 2H), 7.60 (d, J=7.6 Hz, 2H), 7.38–7.42 (m, 2H), 7.29–7.33 (m, 2H), 5.25–5.36 (m, 2H), 4.21–4.38 (m, 4H), 2.40–2.58 (m, 2H), 1.86–1.92 (m, 1H), 1.55–1.62 (m, 2H), 1.41, 1.44 (2s, 9H), 1.23 (bs, 20H), 0.85–0.97 (m, 9H)

Intermediate (83)
$^1$H-NMR ($\delta$ ppm, CDCl$_3$) 7.75–7.77 (m, 2H), 7.56–7.63 (m, 2H), 7.27–7.45 (m, 9H), 5.73–5.78 (m, 1H), 5.25–5.34 (m, 1H), 5.11, 5.12 (2s, 2H), 4.22–4.58 (m, 4H), 2.52–2.91 (m, 4H), 1.44, 1.45 (2s, 9H), 1.16–1.69 (m, 20H), 0.84–0.91 (m, 3H)

Intermediate (98)
$^1$H-NMR ($\delta$ ppm, CDCl$_3$) 7.76 (d, J=7.3 Hz, 2H), 7.60 (d, J=5.9 Hz, 2H), 7.40 (t, J=7.3 Hz, 2H), 7.27–7.37 (m, 7H), 5.39–5.49 (m, 1H), 5.32 (d, J=8.8 Hz, 1H), 5.12 (s, 2H), 4.36–4.41 (m, 2H), 4.32 (dd, J=4.6, 8.8 Hz, 1H), 4.23 (t, J=6.8 Hz, 1H), 3.55 (dd, J=5.1, 11 Hz, 1H), 3.49 (dd, J=4.4, 10 Hz, 1H), 3.31–3.45 (m, 2H), 2.74 (d, J=6.8 Hz, 2H), 1.88 (br s, 1H), 1.36–1.56 (m, 2H), 1.06–1.34 (m, 18H), 0.88 (t, J=6.8 Hz, 3H), 0.85–0.94 (m, 6H)

Intermediate (101)
$^1$H-NMR ($\delta$ ppm, CDCl$_3$) 7.76 (d, J=7.8 Hz, 2H), 7.59 (d, J=5.9 Hz, 2H), 7.39 (t, J=7.6 Hz, 2H), 7.26–7.36 (m, 7H), 5.22–5.36 (m, 2H), 5.10 (s, 2H), 4.34–4.42 (m, 2H), 4.31 (dd, J=4.4, 8.8 Hz, 1H), 4.22 (t, J=7.1 Hz, 1H), 2.69 (dd, J=6.8, 16 Hz, 1H), 2.59 (dd, J=5.6, 15 Hz, 1H), 1.89 (br s, 1H), 1.61 (br s, 2H), 1.05–1.48 (m, 30H), 0.88 (t, J=6.6 Hz, 3H), 0.85–1.00 (m, 6H)

Referential Example 3
Preparation of Intermediate (3)
To 4.62 g of Intermediate (2) obtained in Referential Example 2 was added 9 ml of trifluoroacetic acid. The reaction mixture was stirred at room temperature for 15 minutes. After the solvent was removed in vacuo, the residue was dissolved in ethyl acetate, washed with saturated aqueous sodium hydrogencarbonate, the organic layer was dried over anhydrous sodium sulfate and the solvent was removed in vacuo to afford 3.78 g of
Intermediate (3).

$^1$H-NMR ($\delta$ ppm, $CDCl_3$) 7.31–7.39 (m, 5H), 5.24–5.32 (m, 1H), 5.06–5.14 (m, 2H), 3.02–3.29 (m, 1H), 2.75–2.69 (m, 2H), 1.50–1.75 (m, 4H), 1.30–1.40 (m, 1H), 1.10–1.30 (m, 20H), 0.85–0.94 (m, 9H)

Using the same procedures as described above, the following compounds were prepared:
Intermediate (6)

$^1$H-NMR ($\delta$ ppm, $CDCl_3$) 5.20–5.30 (m, 1H), 3.67 (2s, 3H), 3.33–3.34 (m, 1H), 2.52–2.66 (m, 2H), 1.50–1.80 (m, 5H), 1.10–1.45 (m, 20H), 0.85–1.00 (m, 9H)

Intermediate (70)

$^1$H-NMR ($\delta$ ppm, $d_6$-DMSO) 7.75–7.82 (m, 2H), 7.56–7.68 (m, 2H), 7.25–7.41 (m, 4H), 4.40–4.78 (m, 2H), 4.17–4.25 (m, 1H), 3.74–4.04 (m, 1H), 2.64–3.21 (m, 2H), 1.91–2.15 (m, 1H), 1.03–1.60 (m, 20H), 0.79–0.96 (m, 6H), 0.50–0.70 (m, 3H)

Referential Example 4
Preparation of Intermediate (4)
A solution of 3.46 g of 3-hydroxymyristic acid in a mixed solvent of 50 ml of ether and 10 ml of methanol was cooled in an ice bath. To this solution was slowly added with stirring diazomethane dissolved in ether until the color of the solution changed to a slightly yellowish color. Subsequently, acetic acid was added until the solution became colorless. After the solvent was removed in vacuo, the residue was dissolved in ethyl acetate. The solution was washed with saturated aqueous sodium hydrogencarbonate, dried over anhydrous sodium sulfate and the solvent was removed in vacuo to afford 3.66 g of Intermediate (4).

$^1$H-NMR ($\delta$ ppm, $CDCl_3$) 3.95–4.05 (m, 1H), 3.72 (s, 3H), 2.83 (d, J=3.9 Hz, 1H), 2.52 (dd, J=3.2, 17 Hz, 1H), 2.41 (dd, J=9.0, 17 Hz, 1H), 1.19–1.60 (m, 20H), 0.88 (t, J=6.8 Hz, 3H)

Referential Example 5
Preparation of Intermediate (7)
To a suspension of 5.00 g of N-carbobenzoxy-L-glutamine and 4.36 g of 4,4'-dimethoxybenzhydrol in 45 ml of acetic acid was added dropwise 0.1 ml of conc. anhydrous sulfuric acid and the mixture was stirred at room temperature overnight. To the reaction solution was added 150 ml of water and the crystals thus formed were recovered by filtration and dissolved in ethyl acetate. The resulting solution was washed with water and dried over anhydrous sodium sulfate. After the solvent was removed in vacuo, the residue was dissolved in THF and ether was added thereto to form crystals. The crystals were recovered by filtration and dried under reduced pressure to afford 7.92 g of Intermediate (7).

$^1$H-NMR ($\delta$ ppm, $CDCl_3$) 7.25–7.30 (m, 5H), 7.10 (d, J=8.3 Hz, 4H), 6.82 (d, J=8.3 Hz, 4H), 6.81–6.83 (m, 1H), 6.09 (d, J=7.8 Hz, 1H), 5.91 (d, J=6.8 Hz, 1H), 5.04 (s, 2H), 4.23–4.27 (m, 1H), 3.75 (2s, 6H), 2.45–2.49 (m, 1H), 2.34–2.38 (m, 1H), 2.14–2.17 (m, 1H), 1.96–2.05 (m, 1H)

Referential Example 6
Preparation of Intermediate (8)
To a solution of 17.90 g of Intermediate (7) obtained in Referential Example 5 in 50 ml of DMF were added 0.95 g of 4-dimethylaminopyridine and 1.70 ml of tert-butyl alcohol and then 3.29 g of WSCI was added while stirring under ice-cooling. The reaction mixture was stirred under ice-cooling for 2 hours and then at room temperature overnight. The reaction mixture was concentrated, to the residue thus obtained were added ethyl acetate and water, the organic layer was separated, washed with saturated aqueous sodium hydrogencarbonate and water and dried over anhydrous sodium sulfate. After the solvent was removed in vacuo, the crude product was subjected to column chromatography using 50 g of silica gel and eluted with chloroform:methanol=200:0–2 to afford a product. This product was recrystallized from hexane-ethyl acetate and dried under reduced pressure to afford 4.02 g of Intermediate (8).

$^1$H-NMR ($\delta$ ppm, $CDCl_3$) 7.28–7.37 (m, 5H), 7.11–7.17 (m, 4H), 6.84 (dd, J=2.4, 8.8 Hz, 4H), 6.58 (d, J=8.3 Hz, 1H), 6.14 (d, 7.8 Hz, 1H), 5.52 (d, J=7.8 Hz, 1H), 5.08 (s, 2H), 4.22 (dt, J=3.7, 9.0 Hz, 1H), 3.78 (s, 6H), 2.17–2.36 (m, 3H), 1.85–2.02 (m, 1H), 1.44 (s, 9H)

Referential Example 7
Preparation of Intermediate (9)
In a solution of 4.00 g of Intermediate (8) obtained in Referential Example 6 in 75 ml of methanol was suspended 0.4 g of 5% palladium-carbon at room temperature.

The suspension thus obtained was stirred at room temperature under hydrogen atmosphere for 3 hours. The catalyst was filtered off and the solvent was removed in vacuo from the filtrate to afford 3.00 g of Intermediate (9).

$^1$H-NMR ($\delta$ ppm, $CDCl_3$) 7.13 (d, J=8.7 Hz, 4H), 6.83 (d, J=8.7 Hz, 4H), 6.75 (d, J=7.3 Hz, 1H), 6.13 (d, J=7.8 Hz, 1H), 3.78 (s, 6H), 3.28 (dd, J=4.4, 8.7 Hz, 1H), 2.33–2.45 (m, 2H), 2.06–2.14 (m, 1H), 1.72–1.82 (m, 1H), 1.44 (s, 9H)

Using the same procedures as described above, the following compounds were prepared:
Intermediate (12)

$^1$H-NMR ($\delta$ ppm, $CDCl_3$) 7.13 (d, J=8.3 Hz, 4H), 6.86 (d, J=8.7 Hz, 4H), 6.08 (s, 1H), 5.20–5.30 (m, 1H), 4.20–4.30 (m, 1H), 3.77 (s, 6H), 3.25–3.35 (m, 1H), 2.30–2.55 (m, 4H), 2.10–2.20 (m, 1H), 1.85–1.95 (m, 1H), 1.55–1.75 (m, 3H), 1.46 (s, 9H), 1.15–1.50 (m, 20H), 0.85–0.95 (m, 9H)

Intermediate (14)

$^1$H-NMR ($\delta$ ppm, $CDCl_3$) 7.90 (d, J=7.2 Hz, 1H), 7.72 (d, J=7.6 Hz, 1H), 7.15–7.19 (m, 4H), 6.79–6.84 (m, 4H), 6.11 (d, J=7.6 Hz, 1H), 5.22 (brs, 2H), 4.35 (dt, J=6.0, 8.4 Hz, 1H), 3.90 (t, J=6.8 Hz, 1H), 3.74, 3.75 (2s, 6H), 2.48–2.55 (m, 2H), 2.08–2.19 (m, 2H), 1.44–1.70 (m, 3H), 1.41 (s, 9H), 0.90 (d, J=6.8 Hz, 3H), 0.87 (d, J=6.8 Hz, 3H)

Intermediate (19)

$^1$H-NMR ($\delta$ ppm, $d_6$-DMSO) 7.86 (d, J=7.3 Hz, 2H), 7.67–7.73 (m, 2H), 7.29–7.42 (m, 4H), 4.20–4.64 (m, 4H), 3.35–3.55 (m, 3H), 2.45–2.63 (m, 2H), 1.74–2.12 (m, 4H), 1.38 (s, 9H)

Intermediate (22)

$^1$H-NMR ($\delta$ ppm, $d_6$-DMSO) 7.86 (d, J=7.8 Hz, 1H), 7.68–7.75 (m, 3H), 7.49 (d, J=8.3 Hz, 1H), 7.38–7.42 (m, 2H), 7.29–7.33 (m, 2H), 4.18–4.41 (m, 5H), 2.64–2.69 (m, 1H), 2.43–2.49 (m, 1H), 1.69–1.73 (m, 1H), 1.42–1.48 (m, 1H), 1.37 (s, 9H), 0.86 (s, 9H)

Intermediate (28)

$^1$H-NMR ($\delta$ ppm, $d_6$-DMSO) 7.87 (d, J=7.3 Hz, 2H), 7.68–7.71 (m, 3H), 7.29–7.42 (m, 5H), 7.03 (d, J=8.3 Hz, 2H), 6.70 (d, J=8.3 Hz, 2H), 4.18–4.31 (m, 5H), 2.87–3.25 (m, 2H), 2.59–2.65 (m, 1H), 2.35–2.42 (m, 1H), 1.35 (s, 9H), 1.19 (s, 9H)

Intermediate (38)

¹H-NMR (δ ppm, d₆-DMSO) 8.12 (d, J=7.8 Hz, 2H), 7.86 (d, J=7.3 Hz, 2H), 7.79–7.81 (m,2H), 7.69–7.72 (m,2H), 7.16–7.41 (m, 10H), 4.58–4.64 (m, 1H), 4.38–4.43 (m, 1H), 4.27–4.33 (m, 1H), 4.17–4.20 (m, 2H), 3.85–3.89 (m, 1H), 2.98–3.06 (m, 1H), 2.88–2.93 (m, 1H), 2.60–2.66 (m, 1H), 2.40–2.47 (m, 1H), 1.90–1.96 (m, 1H), 1.34 (s, 9H), 0.80–0.83 (m, 6H)

Intermediate (42)

¹H-NMR (δ ppm, d₆-DMSO) 7.98–8.11 (m, 1H), 7.83–7.91 (m, 3H), 7.56–7.74 (m, 2H), 7.30–7.42 (m, 5H), 4.18–4.38 (m, 5H), 3.88–3.92 (m, 1H), 2.17–2.21 (m, 2H), 1.97–2.02 (m, 1H), 1.84–1.93 (m, 1H), 1.70–1.80 (m, 1H), 1.52–1.63 (m, 3H), 1.35 (s, 9H), 0.82–0.90 (m, 12H)

Intermediate (46)

¹H-NMR (δ ppm, d₆-DMSO) 8.26–8.29 (m, 1H), 7.87 (d, J=7.8 Hz, 2H), 7.56–7.77 (m, 3H), 7.29–7.45 (m, 5H), 4.63–4.69 (m, 1H), 4.12–4.28 (m, 4H), 3.77–3.81 (m, 1H), 2.70–2.75 (m, 1H), 2.39–2.47 (m, 1H), 1.90–1.97 (m, 1H), 1.45–1.63 (m, 3H), 1.37 (s, 9H), 0.78–0.90 (m, 12H)

Intermediate (50)

¹H-NMR (δ ppm, d₆-DMSO) 8.01 (d, J=7.8 Hz, 1H), 7.86 (d, J=7.3 Hz, 2H), 7.70–7.73 (m, 3H), 7.30–7.44 (m, 5H), 4.44–4.47 (m, 1H), 4.21–4.32 (m, 4H), 3.89–3.93 (m, 1H), 3.40–3.50 (m, 2H), 1.98–2.03 (m, 1H), 1.64–1.71 (m, 1H), 1.46–1.58 (m, 2H), 1.08 (s, 9H), 0.83–0.88 (m, 12H)

Intermediate (54)

¹H-NMR (δ ppm, d₆-DMSO) 8.56 (d, J=7.3 Hz, 1H), 8.23–8.31 (m, 1H), 7.85–7.88 (m, 2H), 7.55–7.74 (m, 3H), 7.31–7.40 (m, 5H), 7.09–7.14 (m, 4H), 6.80–6.86 (m, 4H), 5.95 (d, J=8.3 Hz, 1H), 4.65–4.69 (m, 1H), 4.19–4.29 (m, 4H), 3.86–3.90 (m, 1H), 3.70 (s, 3H), 3.69 (s, 3H), 2.57–2.68 (m, 2H), 1.94–2.02 (m, 1H), 1.45–1.60 (m, 3H), 0.78–0.84 (m, 12H)

Intermediate (56)

¹H-NMR (δ ppm, d₆-DMSO) 8.23–8.28 (m, 1H), 7.83–7.98 (m, 3H), 7.54–7.62 (m, 3H), 7.15–7.44 (m, 9H), 4.64–4.69 (m, 1H), 4.11–4.31 (m, 5H), 2.47–3.05 (m, 4H), 1.51–1.68 (m, 3H), 1.36 (s, 9H), 0.87 (d, J=6.3 Hz, 3H), 0.84 (d, J=6.3 Hz, 3H)

Intermediate (66)

¹H-NMR (δ ppm, d₆-DMSO) 7.29–8.27 (m, 11H), 4.61–4.64 (m, 1H), 4.16–4.34 (m, 4H), 3.86–3.97 (m, 1H), 2.44–2.72 (m, 2H), 1.94–2.00 (m, 1H), 1.46–1.63 (m, 3H), 1.35 (s, 9H), 0.79–6.91 (m, 12H)

Intermediate (67)

¹-H-NMR (δ ppm, CDCl₃) 7.73–7.76 (m, 2H), 7.55–7.57 (m, 2H), 7.26–7.40 (m, 4H), 7.03 (d, J=8.1 Hz, 1H), 6.20 (br, 1H), 4.64–4.67 (m, 1H), 4.54–4.57 (m, 1H), 4.35–4.37 (m, 2H), 4.20 (d, J=6.8 Hz, 1H), 2.66–2.84 (m, 2H), 1.52–1.73 (m, 3H), 1.43 (s, 9H), 0.90–0.92 (m, 6H)

Intermediate (86)

¹H-NMR (δ ppm, CDCl₃) 7.96 (d, J=8.4 Hz, 1H), 4.67 (dt, J=4.4, 8.4 Hz, 1H), 3.43 (dd, J=4.8, 7.6 Hz, 1H), 2.89 (dd, J=4.4, 17.2 Hz, 1H), 2.70 (dd, J=4.4, 17.2 Hz, 1H), 2.27–2.42 (m, 2H), 2.03–2.14 (m, 1H), 1.77–1.88 (m, 1H), 1.47–1.63 (m, 2H), 1.463 (s, 9H), 1.455 (s, 9H), 1.436 (s, 9H)

Referential Example 8

Preparation of Intermediate (10)

To a solution of 3.00 g of Intermediate (9) obtained in Referential Example 7 in 50 ml of DMF were added 1.74 g of 3-hydroxymyristic acid and 1.20 g of HOBt and then 1.50 g of WSCI was added while stirring under ice-cooling. The reaction mixture was stirred under ice-cooling for 2 hours and then at room temperature for 6 hours. The solvent was removed in vacuo, ethyl acetate and 10% aqueous citric acid were added to the residue, the organic layer was separated and washed in turn with water, 5% aqueous sodium hydrogencarbonate and water and dried over anhydrous sodium sulfate. After the solvent was removed in vacuo, the crude product was subjected to column chromatography using silica gel (30 g) and eluted with chloroform:methanol= 200:0–10 to afford a product, which was then recrystallized from chloroform-ether to afford 3.90 g of Intermediate (10).

¹H-NMR (δ ppm, CDCl₃) 7.14–7.17 (m, 4H), 6.83–6.86 (m, 4H), 6.70–6.80 (m, 2H), 6.13–6.15 (m, 1H), 4.35–4.45 (m, 1H), 3.92 (br s, 1H), 3.78 (2s, 6H), 3.45, 3.57 (2br s, 1H), 2.15–2.35 (m, 5H), 1.90–2.00 (m, 1H), 1.69 (br s, 2H), 1.45 (s, 9H), 1.20–1.50 (m, 18H), 0.88 (t, J=6.8 Hz, 3H)

Using the same procedures as described above, the following compounds were prepared:

Intermediate (13)

¹H-NMR (δ ppm, CDCl₃) 7.31–7.34 (m, 5H), 7.13–7.22 (m, 5H), 6.83–6.86 (m, 4H), 6.53 (d, J=7.6 Hz, 1H), 6.21 (d, J=8.4 Hz, 1H), 5.76 (d, J=7.6 Hz, 1H), 5.10 d, J=12.4 Hz, 1H), 5.05 (d, J=12.4 Hz, 1H), 4.37 (ddd, J=12.8, 8.4, 4.8 Hz, 1H), 4.16–4.19 (m, 1H), 3.76, 3.77 (2s, 3H), 2.37–2.40 (m, 2H), 2.07 (q, J=6.8 Hz, 2H), 1.43 (s, 9H), 1.25–1.72 (m, 3H), 0.84–0.90 (m, 6H)

Intermediate (15)

¹H-NMR (δ ppm, CDCl₃) 7.12–7.22 (m, 4H), 6.80–7.02 (m, 7H), 6.19 (d, J=8.4 Hz, 1H), 4.37–4.42 (m, 2H), 3.85–3.92 (m, 1H), 3.78 (2s, 6H), 2.08–2.40 (m, 6H), 1.22–1.50 (m, 23H), 1.44 (s, 9H), 0.86–0.90 (m, 9H)

Intermediate (18)

¹H-NMR (δ ppm, CDCl₃) 7.74–7.76 (m, 2H), 7.56–7.59 (m, 2H), 7.25–7.40 (m, 9H), 5.67 (d, J=8.8 Hz, 1H), 5.19 (d, J=12.2 Hz, 1H), 5.11 (d, J=12.2 Hz, 1H), 4.88–4.90 (m, 1H), 4.55–4.58 (m, 3H), 4.19–4.22 (m, 1H), 3.72–3.76 (m, 2H), 2.65 (dd, J=4.9, 15.6 Hz, 1H), 2.48–2.53 (m, 1H), 2.00–2.19 (m, 4H), 1.45 (s, 9H)

Intermediate (21)

¹H-NMR (δ ppm, CDCl₃) 7.76 (d, J=7.8 Hz, 2H), 7.58 (d, J=7.3 Hz, 2H), 7.29–7.42 (m, 9H), 6.90 (d, J=7.8 Hz, 1H), 5.97 (d, J=8.3 Hz, 1H), 5.13 (s, 2H), 4.60–4.66 (m, 1H), 4.51–4.55 (m, 1H), 4.38–4.41 (m, 2H), 4.20–4.24 (m, 1H), 2.85–2.90 (m, 1H), 2.58–2.64 (m, 1H), 1.61–1.80 (m, 2H), 1.45 (s, 9H)

Intermediate (23)

¹H-NMR (δ ppm, CDCl₃) 7.73–7.77 (m, 2H), 7.58–7.61 (m, 2H), 7.27–7.41 (m, 9H), 7.13–7.17 (m, 4H), 6.74–6.87 (m, 5H), 6.56–6.60 (m, 1H), 6.17–6.22 (m, 2H), 5.17 (d, J=12.4 Hz, 1H), 5.09 (d, J=12.4 Hz, 1H), 4.50–4.58 (m, 1H), 4.25–4.48 (m, 2H), 4.17–4.21 (m, 2H), 3.77 (s, 3H), 3.70 (s, 3H), 2.30–2.40 (m, 2H), 2.15–2.19 (m, 1H), 2.05–2.08 (m, 1H), 1.50–1.60 (m, 2H), 1.25–1.36 (m, 1H), 0.82–0.85 (m, 6H)

Intermediate (27)

¹H-NMR (δ ppm, CDCl₃) 7.76 (d, J=7.3 Hz, 1H), 7.58 (d, J=7.3 Hz, 2H), 7.29–7.42 (m, 9H), 7.04 (d, J=7.3 Hz, 1H), 6.94 (d, J=8.3 Hz, 1H), 6.82 (d, J=8.8 Hz, 2H), 5.91 (d, J=7.8 Hz, 1H), 5.13 (d, J=12.2 Hz, 1H), 5.07 (d, J=12.2 Hz, 1H), 4.79–4.84 (m, 1H), 4.49–4.53 (m, 1H), 4.35–4.38 (m, 2H), 4.19–4.23 (m, 1H), 3.03–3.06 (m, 2H), 2.84–2.88 (m, 1H), 2.54–2.60 (m, 1H), 1.43 (s, 9H), 1.28 (s, 9H)

Intermediate (29)

¹H-NMR (δ ppm, CDCl₃) 7.74–7.78 (m, 2H), 7.58 (t, J=8.0 Hz, 2H), 7.27–7.43 (m, 9H), 5.43, 5.72 (2d, J=9.6 Hz, 1H), 4.83–5.45 (m, 3H), 4.50–4.62 (m, 1H), 4.18–4.38 (m, 3H), 3.55–3.82 (m, 2H), 2.80 (dd, J=8.0, 16.4 Hz, 1H), 2.56 (dd, J=5.6, 16.4 Hz, 1H), 2.31–2.54 (m, 1H), 2.09–2.14 (m, 3H), 1.42, 1.46 (2s, 9H)

Intermediate (31)

¹H-NMR (δ ppm, CDCl₃) 7.77 (d, J=7.3 Hz, 2H), 7.59 (d, J=7.8 Hz, 2H), 7.40 (t, J=7.3 Hz, 2H), 7.28–7.37 (m, 7H), 6.94 (d, J=7.8 Hz, 1H), 5.96 (d, J=7.8 Hz, 1H), 5.17 (d, J=12 Hz, 1H), 5.13 (d, J=12 Hz, 1H), 4.53–4.67 (m, 2H), 4.39 (d, J=6.8 Hz, 2H), 4.23 (t, J=7.1 Hz, 1H), 2.89 (dd, J=3.2, 17 Hz, 1H), 2.62 (dd, J=6.8, 17 Hz, 1H), 1.51–1.70 (m, 3H), 1.44 (s, 9H), 0.90 (d, J=2.4 Hz, 3H), 0.88 (d, J=2.4 Hz, 3H)

Intermediate (33)

¹H-NMR (CDCl₃) δ ppm, 7.77 (2H, d, J=7.3 Hz), 7.60 (2H, d, J=8.3 Hz), 7.40 (2H, dt, J=3.4, 7.3 Hz), 7.27–7.37 (7H, m), 7.22 (1H, d, J=7.8 Hz), 7.08 (1H, d, J=7.3 Hz), 5.29 (1H, d, J=6.8 Hz), 5.09 (2H, s), 4.79–4.86 (1H, m), 4.56–4.63 (1H, m), 4.41 (2H, d, J=7.3 Hz), 4.23 (1H, t, J=6.8 Hz), 4.01 (1H, t, J=6.3 Hz), 2.90 (1H, dd, J=4.4, 17 Hz), 2.58 (1H, dd, J=6.5, 17 Hz), 2.10–2.20 (1H, m), 1.56–1.68 (3H, m), 1.42 (9H, s), 0.98 (3H, d, J=6.8 Hz), 0.93 (3H, d, J=6.8 Hz), 0.85–0.91 (6H, m)

Intermediate (35)

¹H-NMR (δ ppm, CDCl₃) 7.04–7.78 (m, 19H), 5.92 (d, J=7.3 Hz, 1H), 5.14 (d, J=12.2 Hz, 1H), 5.08 (d, J=12.2 Hz, 1H), 4.82–4.87 (m, 1H), 4.52 (br s, 1H), 4.31–4.40 (m, 2H), 4.18–4.22 (m, 1H), 3.05–3.15 (m, 2H), 2.85–2.89 (m, 1H), 2.54–2.61 (m, 1H), 1.43 (s, 9H)

Intermediate (37)

¹H-NMR (δ ppm, CDCl₃) 7.75 (d, J=7.8 Hz, 2H), 7.58 (d, J=7.3 Hz, 2H), 7.05–7.40 (m, 11H), 5.42 (d, J=7.8 Hz, 1H), 5.12 (d, J=12.2 Hz, 1H), 5.06 (d, J=12.2 Hz, 1H), 4.75–4.85 (m, 2H), 4.32–4.43 (m, 2H), 4.19–4.22 (m, 1H), 4.00–4.04 (m, 1H), 3.05–3.09 (m, 2H), 2.86–2.95 (m, 1H), 2.49–2.52 (m, 1H), 1.97–2.03 (m, 1H), 1.40 (s, 9H), 0.89 (d, J=6.3 Hz, 3H), 0.84 (d, J=6.3 Hz, 3H)

Intermediate (39)

¹H-NMR (δ ppm, CDCl₃) 7.76 (d, J=7.3 Hz, 2H), 7.59 (d, J=7.3 Hz, 2H), 7.28–7.42 (m, 9H), 6.66–6.68 (m, 1H), 5.77–5.79 (m, 1H), 5.16 (d, J=12.2 Hz, 1H), 5.12(d, J=12.2 5 Hz, 1H), 4.62–4.65 (m, 1H), 4.37 (d, J=7.2 Hz, 1H), 4.21–4.24 (m, 1H), 4.21 (t, J=7.2 Hz, 1H), 2.42–2.47 (m, 1H), 2.30–2.35 (m, 1H), 2.04–2.09 (m, 1H), 1.93–1.98 (m, 1H), 1.58–1.66 (m, 3H), 1.46 (s, 9H), 0.88–0.91 (m, 6H)

Intermediate (41)

¹H-NMR (δ ppm, CDCl₃) 7.76 (d, J=7.4 Hz, 2H), 7.58 (t, J=8.6 Hz, 2H), 7.25–7.41 (m, 9H), 7.05 (d, J=7.8 Hz, 1H), 5.45 (d, J=7.4 Hz, 1H), 5.12 (d, J=12.2 Hz, 1H), 5.06 (d, J=12.2 Hz, 1H), 4.58–4.65 (m, 1H), 4.49–4.54 (m, 1H), 4.32–4.46 (m, 2H), 4.22 (t, J=6.8 Hz, 1H), 4.03 (t, J=6.4 Hz, 1H), 2.41–2.49 (m, 1H), 2.24–2.32 (m, 1H), 1.93–2.22 (m, 4H), 1.65 (m, 3H), 1.43 (s, 9H), 0.88–0.95 (m, 12H)

Intermediate (43)

¹H-NMR (δ ppm, CDCl₃) 7.76 (d, J=7.2 Hz, 2H), 7.58 (d, J=7.2 Hz, 2H), 7.29–7.43 (m, 9H), 6.99 (d, J=8.0 Hz, 1H), 6.00 (d, J=8.0 Hz, 1H), 5.16 (d, J=12.4 Hz, 1H), 5.11 (d, J=12.4 Hz, 1H), 4.58–4.65 (m, 2H), 4.41 (d, J=6.8 Hz, 2H), 4.22 (t, J=6.8 Hz, 1H), 2.92 (dd, J=3.6, 17.2 Hz, 1H), 2.57 (dd, J=6.8, 17.2 Hz, 1H), 1.54–1.65 (m, 3H), 1.45 (s, 9H), 0.90 (d, J=5.2 Hz, 6H)

Intermediate (45)

¹H-NMR (δ ppm, CDCl₃) 7.75 (d, J=7.6 Hz, 2H), 7.57 (d, J=7.6 Hz, 2H), 7.29–7.41 (m, 9H), 7.17 (d, J=8.4 Hz, 1H), 5.33 (d, J=7.8 Hz, 1H), 5.09 (d, J=12.4 Hz, 1H), 5.06 (d, J=12.4 Hz, 1H), 4.79–4.83 (m, 1H), 4.59 (dd, J=7.6, 14.8 Hz, 1H), 4.29–4.41 (m, 2H), 4.20 (t, J=6.8 Hz, 1H), 3.88 (t, J=7.6 Hz, 1H), 3.00 (dd, J=3.6, 17.2 Hz, 1H), 2.51 (dd, J=6.8, 17.2 Hz, 1H), 2.08–2.20 (1H, m), 1.62–1.66 (m, 3H), 1.43 (s, 9H), 0.97 (d, J=6.8 Hz, 3H), 0.89 (d, J=5.6 Hz, 3H), 0.86 (d, J=5.6 Hz, 3H)

Intermediate (47)

¹H-NMR (δ ppm, CDCl₃) 7.75–7.77 (m, 2H), 7.58–7.60 (m, 2H), 7.31–7.41 (m, 9H), 7.06 (brs, 1H), 5.76 (brs, 1H), 5.16 (s, 2H), 4.65–4.71 (m, 1H), 4.38 (d, J=6.8 Hz, 2H), 4.20–4.24 (m, 2H), 3.81–3.83 (m, 1H), 3.35–3.39 (m, 1H), 1.51–1.70 (m, 3H), 1.20 (s, 9H), 0.90–0.93 (m, 6H)

Intermediate (49)

¹H-NMR (δ ppm, CDCl₃) 7.75–7.77 (m, 2H), 7.59–7.61 (m, 2H), 7.28–7.42 (m, 9H), 7.12 (d, J=8.3 Hz, 1H), 6.75–6.77 (m, 1H), 5.36–5.38 (m, 1H), 5.13 (s, 2H), 4.64–4.69 (m, 1H), 4.34–4.68 (m, 3H), 4.22 (t, J=6.8 Hz, 1H), 4.04 (t, J=6.3 Hz, 1H), 3.83 (dd, J=3.4, 8.3 Hz, 1H), 3.34 (t, J=8.3 Hz, 1H), 2.12–2.17 (m, 1H), 1.58–1.70 (m, 3H), 1.17 (s, 9H), 0.90–0.99 (m, 12H)

Intermediate (53)

¹H-NMR (δ ppm, CDCl₃) 7.93 (d, J=5.0 Hz, 1H), 7.75 (d, J=7.2 Hz, 2H), 7.26–7.63 (m, 7H), 7.04 (d, J=7.2 Hz, 4H), 6.74–6.82 (m, 4H), 6.43 (d, J=7.2 Hz, 1H), 6.02 (d, J=7.2 Hz, 1H), 5.33 (d, J=5.0 Hz, 1H), 5.03 (d, J=12.0 Hz, 1H), 4.96 (d, J=12.0 Hz, 1H), 4.75–4.79 (m, 1H), 4.51–4.60 (m, 1H), 4.44 (dd, J=6.4, 10.4 Hz, 1H), 4.31 (t, J=6.8 Hz, 1H), 4.24 (t, J=6.8 Hz, 1H), 4.03 (t, J=6.8 Hz, 1H), 3.76 (s, 3H), 3.70 (s, 3H), 2.91 (dd, J=3.0, 15.5 Hz, 1H), 2.10–2.13 (m, 1H), 1.63–1.67 (m, 3H), 0.88–0.97 (m, 12H)

Intermediate (55)

¹H-NMR (δ ppm, CDCl₃) 6.98–7.76 (m, 20H), 5.16–5.21 (m, 1H), 5.09 (d, J=12.6 Hz, 2H), 5.05 (d, J=12.6 Hz, 2H), 4.74–4.82 (m, 1H), 4.54–4.59 (m, 1H), 4.29–4.41 (m, 3H), 4.18 (t, J=6.8 Hz, 1H), 3.11–3.20 (m, 2H), 2.97–3.06 (m, 1H), 2.82–2.91 (m, 1H), 2.48–2.54 (m, 1H), 1.59–1.64 (m, 3H), 1.38 (s, 9H), 0.88 (d, J=6.3 Hz, 3H), 0.89 (d, J=6.3 Hz, 3H)

Intermediate (65)

¹H-NMR (δ ppm, CDCl₃) 7.77 (d, J=7.3 Hz, 1H), 7.59 (d, J=7.3 Hz, 1H), 7.30–7.42 (m, 9H), 7.18 (d, J=6.8 Hz, 1H), 7.09 (d, J=7.8 Hz, 1H), 5.32 (d, J=7.8 Hz, 1H), 5.10–5.18 (m, 2H), 4.76–4.79 (m, 1H), 4.54–4.57 (m, 1H), 4.35–4.47 (m, 2H), 4.21–4.25 (m, 1H), 4.02–4.06 (m, 1H), 2.88–2.92 (m, 1H), 2.52 (dd, J=7.3, 17.1 Hz, 1H), 2.16–2.19 (m, 1H), 1.51–1.65 (m, 3H), 1.43 (s, 9H), 0.87–1.00 (m, 12H)

Intermediate (71)

¹H-NMR (δ ppm, CDCl₃) 7.76 (d, J=7.8 Hz, 2H), 7.59 (d, J=7.3 Hz, 2H), 7.38–7.42 (m, 2H), 7.29–7.33 (m, 2H), 6.70 (d, J=7.8 Hz, 1H), 5.75 (d, J=7.3 Hz, 1H), 4.19–4.48 (m, 5H), 2.40–2.44 (m, 2H), 2.07–2.11 (m, 1H), 1.92–1.97 (m, 1H), 1.44–1.65 (m, 21H), 0.93 (d, J=6.3 Hz, 3H), 0.92 (d, J=5.9 Hz, 3H)

Intermediate (73)

¹H-NMR (δ ppm, CDCl₃) 7.76 (d, J=7.8 Hz, 2H), 7.58 (d, J=7.8 Hz, 2H), 7.40 (t, J=7.3 Hz, 2H), 7.31 (t, J=7.3 Hz, 2H), 6.26 (d, J=8.3 Hz, 1H), 5.43 (br s, 1H), 4.20–4.51 (m, 5H), 1.40–1.67 (m, 15H), 0.92 (d, J=5.9 Hz, 3H), 0.91 (d, J=6.3 Hz, 3H)

Intermediate (75)

¹H-NMR (δ ppm, CDCl₃) 7.76 (d, J=7.3 Hz, 2H), 7.59 (d, J=7.3 Hz, 2H), 7.39–7.42 (m, 2H), 7.30–7.34 (m, 2H), 6.91 (d, J=8.8 Hz, 1H), 6.00 (d, J=8.3 Hz, 1H), 4.56 (br s, 1H), 4.40–4.48 (m, 3H), 4.23 (t, J=6.8 Hz, 1H), 2.91–2.97 (m, 1H), 2.58–2.64 (m, 1H), 1.48–1.70 (m, 3H), 1.46 (s, 9H), 1.44 (s, 9H), 0.93 (d, J=6.3 Hz, 3H), 0.92 (d, J=6.3 Hz, 3H)

Intermediate (80)

¹H-NMR (δ ppm, CDCl₃) 6.78–6.97 (m, 1H), 6.64–6.68 (m, 1H), 4.39–4.52 (m, 2H), 3.92–4.05 (m, 1H), 3.61–3.88 (m, 1H), 2.19–2.52 (m, 4H), 1.87–2.16 (m, 2H), 1.460 (s, 9H), 1.456 (s, 9H), 1.19–1.72 (m, 23H), 0.86–0.96 (m, 6H)

Intermediate (85)

¹H-NMR (δ ppm, CDCl₃) 7.28–7.39 (m, 5H), 7.01 (d, J=8.4 Hz, 1H), 5.60 (d, J=3.6 Hz, 1H), 5.10 (s, 2H), 4.69 (dt, J=4.4, 8.4 Hz, 1H), 4.22–4.30 (m, 1H), 2.89 (dd, J=4.4, 16.8 Hz, 1H), 2.66 (dd, J=4.4, 16.8 Hz, 1H), 2.07–2.18 (m, 1H), 1.90–1.98 (m, 1H), 1.452 (s, 9H), 1.442 (s, 9H), 1.438 (s, 9H)

Intermediate (87)

$^1$H-NMR (δ ppm, CDCl$_3$) 7.76 (d, J=7.3 Hz, 2H), 7.57 (d, J=7.3 Hz, 2H), 7.39 (t, J=7.6 Hz, 2H), 7.27–7.36 (m, 7H), 6.52 (d, J=7.8 Hz, 1H), 5.19 (d, J=7.8 Hz, 1H), 5.14 (d, J=12 Hz, 1H), 5.09 (d, J=12 Hz, 1H), 4.60–4.68 (m, 1H), 4.34–4.46 (m, 2H), 4.21 (t, J=7.1 Hz, 1H), 4.17–4.29 (m, 1H), 1.43–1.76 (m, 6H), 0.93 (d, J=5.4 Hz, 6H), 0.89 (d, J=5.9 Hz, 6H)

Intermediate (89)

$^1$H-NMR (δ ppm, CDCl$_3$) 8.51 (d, J=8.3 Hz, 1H), 8.23 (d, J=7.8 Hz, 1H), 7.86 (d, J=7.8 Hz, 2H), 7.78 (d, J=7.8 Hz, 1H), 7.70 (t, J=5.9 Hz, 2H), 7.47 (d, J=7.8 Hz, 1H), 7.39 (t, J=7.3 Hz, 2H), 7.26–7.36 (m, 7H), 7.14 (dd, J=1.5, 8.8 Hz, 4H), 6.83 (dd, J=2.4, 8.8 Hz, 4H), 6.02 (d, J=8.3 Hz, 1H), 5.06 (s, 2H), 4.35–4.46 (m, 1H), 4.17–4.34 (m, 4H), 4.00–4.08 (m, 1H), 3.71 (s, 3H), 3.70 (s, 3H), 2.21–2.34 (m, 2H), 1.90–2.01 (m, 1H), 1.74–1.87 (m, 1H), 1.47–1.64 (m, 4H), 1.44 (t, J=7.1 Hz, 2H), 0.75–0.91 (m, 12H)

Intermediate (91)

$^1$H-NMR (δ ppm, CDCl$_3$) 7.21 (d, J=8.8 Hz, 2H), 7.15 (d, J=8.8 Hz, 2H), 6.96 (d, J=8.3 Hz, 1H), 6.87 (d, J=4.9 Hz, 2H), 6.85 (d, J=4.4 Hz, 2H), 6.80 (d, J=7.3 Hz, 1H), 6.67 (d, J=8.3 Hz, 1H), 6.21 (d, J=8.3 Hz, 1H), 4.33–4.45 (m, 2H), 3.92 (br s, 1H), 3.79 (s, 3H), 3.78 (s, 3H), 3.69 (d, J=2.4 Hz, 1H), 2.37–2.51 (m, 2H), 2.34 (dd, J=2.9, 15 Hz, 1H), 2.21 (dd, J=8.8, 15 Hz, 1H), 2.09 (q, J=6.5 Hz, 2H), 1.44 (s, 9H), 1.18–2.07 (m, 23H), 0.90 (t, J=6.4 Hz, 3H), 0.87 (d, J=6.8 Hz, 6H)

Intermediate (94)

$^1$H-NMR (δ ppm, CDCl$_3$) 7.19 (d, J=8.8 Hz, 2H), 7.14 (d, J=8.8 Hz, 2H), 6.92 (d, J=8.3 Hz, 1H), 6.90 (d, J=6.8 Hz, 1H), 6.82–6.88 (m, 4H), 6.81 (d, J=8.3 Hz, 1H), 6.20 (d, J=8.3 Hz, 1H), 4.34–4.42 (m, 2H), 3.96 (br s, 1H), 3.83–3.88 (m, 1H), 3.79 (s, 3H), 3.78 (s, 3H), 2.36–2.51 (m, 2H), 2.30 (dd, J=2.4, 15 Hz, 1H), 2.18 (dd, J=9.8, 15 Hz, 1H), 2.09 (q, J=6.7 Hz, 2H), 1.44 (s, 9H), 1.18–1.61 (m, 23H), 0.85–0.92 (m, 9H)

Referential Example 9

Preparation of Intermediate (17)

To a solution of 9.93 g of Intermediate (16) obtained in the same manner as in Referential Example 2 in 130 ml of DMF was added 10 ml of diethylamine, and the mixture was stirred at room temperature for 3 hours. The reaction solvent was removed in vacuo, the residue was purified by a silica gel column chromatography (chloroform:methanol=90:10) to afford 7.23 g of Intermediate (17).

$^1$H-NMR (δ ppm, CDCl$_3$) 7.12–7.23 (m, 4H), 6.83–6.87 (m, 4H), 6.64–6.71 (m, 2H), 6.16–6.21 (m, 1H), 5.25–5.27 (m, 1H), 4.32–4.40 (m, 2H), 3.78, 3.79 (s, 6H), 3.22–3.28 (m, 1H), 2.37–2.44 (m, 4H), 1.92–2.20 (m, 2H), 1.12–1.65 (m, 26H), 1.43 (s, 9H), 0.83–0.93 (m, 15H)

Using the same procedures as described above, the following compounds were prepared:

Intermediate (26)

$^1$H-NMR (δ ppm, CDCl$_3$) 7.31–7.38 (m, 5H), 7.03 (d, J=8.3 Hz, 2H), 6.88 (d, J=8.3 Hz, 2H), 5.13 (s, 2H), 3.73–3.76 (m, 1H), 3.03 (dd, J=5.4, 13.6 Hz, 1H), 2.85 (dd, J=7.3, 13.6 Hz, 1H), 1.52 (br s, 2H), 1.32 (s, 9H)

Intermediate (36)

$^1$H-NMR (δ ppm, CDCl$_3$) 7.81 (d, J=8.3 Hz, 1H), 7.04–7.36 (m, 10H), 5.15 (d, J=12.2 Hz, 1H), 5.10 (d, J=12.2 Hz, 1H), 3.60–3.63 (m, 1H), 3.05–3.15 (m, 2H), 2.75 (dd, J=3.9, 16.6 Hz, 1H), 2.37 (dd, J=8.3, 16.6 Hz, 1H), 1.76 (br, 2H), 1.44 (s, 9H)

Intermediate (52)

$^1$H-NMR (δ ppm, CDCl$_3$) 7.71 (d, J=7.3 Hz, 1H), 7.27–7.35 (m, 5H), 7.09–7.13 (m, 4H), 6.93 (d, J=7.6 Hz, 1H), 6.81–6.85 (m, 4H), 6.09 (d, J=7.6 Hz, 1H), 5.15 (d, J=12.4 Hz, 1H), 5.07 (d, J=12.4 Hz, 1H), 4.57 (dt, J35.0, 8.5 Hz, 1H), 3.78 (s, 3H), 3.77 (s, 3H), 3.71 (dd, J=3.9, 8.3 Hz, 1H), 2.71 (dd, J=3.9, 15.1 Hz, 1H), 2.43 (dd, J=8.3, 15.1 Hz, 1H), 1.67–1.77 (m, 3H), 1.53–1.64 (m, 2H), 0.89–0.96 (m, 6H)

Intermediate (72)

$^1$H-NMR (δ ppm, CDCl$_3$) 7.54 (d, J=8.3 Hz, 1H), 4.45–4.50 (m, 1H), 3.40–3.43 (m, 1H), 2.34–2.38 (m, 2H), 2.05–2.14 (m, 1H), 1.77–1.86 (m, 1H), 1.48–1.70 (m, 5H), 1.46 (s, 9H), 1.44 (s, 9H), 0.96 (d, J=6.3 Hz, 3H), 0.95 (d, J=5.9 Hz, 3H)

Intermediate (74)

$^1$H-NMR (δ ppm, CDCl$_3$) 7.57 (d, J=8.3 Hz, 1H), 4.45–4.51 (m, 1H), 3.49–3.54 (m, 1H), 1.49–1.70 (m, 5H), 1.46 (s, 9H), 1.33 (d, J=6.8 Hz, 3H), 0.95 (d, J=5.9 Hz, 3H), 0.94 (d, J=5.9 Hz, 3H)

Intermediate (76)

$^1$H-NMR (δ ppm, CDCl$_3$) 7.71 (d, J=7.3 Hz, 1H), 4.44–4.50 (m, 1H), 3.67–3.69 (m, 1H), 2.82 (dd, J=3.4, 17 Hz, 1H), 2.51 (dd, J=8.3, 17 Hz, 1H), 1.71 (br s, 2H), 1.50–1.68 (m, 3H), 1.46 (s, 9H), 1.45 (s, 9H), 0.95 (d, J=6.3 Hz, 3H), 0.94 (d, J=6.3 Hz, 3H)

Intermediate (79)

$^1$H-NMR (δ ppm, CDCl$_3$) 5.21–5.25 (m, 1H), 3.29–3.31 (m, 1H), 2.32–2.57 (m, 2H), 1.19–1.74 (m, 34H), 0.86–0.97 (m, 9H)

Intermediate (82)

$^1$H-NMR (δ ppm, CDCl$_3$) 6.70–6.85 (m, 2H), 5.14–5.23 (m, 1H), 4.38–4.48 (m, 2H), 3.68–3.73 (m, 1H), 2.32–2.76 (m, 6H), 1.44–2.14 (m, 34H), 1.20–1.34 (m, 18H), 0.86–0.96 (m, 9H)

Intermediate (84)

$^1$H-NMR (δ ppm, CDCl$_3$) 7.28–7.40 (m, 5H), 5.23–5.31 (m, 1H), 5.11 (s, 2H), 3.51–3.69 (m, 1H), 2.44–2.74 (m, 4H), 1.44, 1.45 (2s, 9H), 1.04–1.69 (m, 22H), 0.88 (t, J=6.8 Hz, 3H)

Intermediate (93)

$^1$H-NMR (δ ppm, CDCl$_3$) 7.37 (d, J=8.3 Hz, 1H), 7.21 (d, J=8.8 Hz, 2H), 7.14 (d, J=8.8 Hz, 2H), 6.86 (d, J=6.3 Hz, 2H), 6.84 (d, J=6.8 Hz, 2H), 6.65 (d, J=7.3 Hz, 1H), 6.57 (d, J=7.8 Hz, 1H), 6.19 (d, J=8.3 Hz, 1H), 5.23–5.30 (m, 1H), 4.32–4.41 (m, 2H), 3.79 (s, 3H), 3.78 (s, 3H), 3.27 (d, J=4.9 Hz, 1H), 2.31–2.49 (m, 4H), 2.08–2.17 (m, 1H), 1.93–2.04 (m, 1H), 1.44 (s, 9H), 1.08–1.74 (m, 26H), 0.85–0.95 (m, 15H)

Referential Example 10

Preparation of Intermediate (20)

To a solution of 3.12 g of D-tert-butylalanine in 50 ml of benzene were added 10 ml of benzyl alcohol and 4.82 g of p-toluenesulfonic acid-monohydrate and the mixture was heated under reflux for 4.5 hours. The reaction solution was allowed to cool to room temperature, and 50 ml of hexane was added. The crystals thus formed were recovered by filtration and ethyl acetate and 5% aqueous sodium hydrogencarbonate were added. After vigorous stirring, the organic layer was separated and dried over anhydrous sodium sulfate. The solvent was removed in vacuo to afford 5.56 g of Intermediate (20).

$^1$H-NMR (δ ppm, CDCl$_3$) 7.76 (d, J=7.8 Hz, 2H), 7.58 (d, J=7.3 Hz, 2H), 7.29–7.42 (m, 9H), 6.90 (d, J=7.8 Hz, 1H), 5.97 (d, J=8.3 Hz, 1H), 5.13 (s, 2H), 4.51–4.66 (m, 2H), 4.38–4.41 (m, 2H), 4.20–4.24 (m, 1H), 2.85–2.90 (m, 1H), 2.58–2.64 (m, 1H), 1.76–1.81 (m, 1H), 1.59–1.64 (m, 1H), 1.45 (s, 9H), 0.92 (s, 9H)

Referential Example 11
Preparation of Intermediate (77)

To a suspension of 1.00 g of 3-hydroxymyristic acid in 20 ml of tert-butyl acetate was added at room temperature 2.0 ml of boron trifluoride diethyl etherate. The reaction mixture was stirred at room temperature for 3 hours, poured into water and extracted with ethyl acetate. The organic layer was dried over anhydrous sodium sulfate.

After the solvent was removed in vacuo, the crude product was subjected to column chromatography using silica gel and eluted with hexane:ethyl acetate=9:1 to afford 0.71 g of Intermediate (77).

$^1$H-NMR (δ ppm, CDCl$_3$) 3.94–3.97 (m, 1H), 3.06 (d, J=3.7 Hz, 1H), 2.42 (dd, J=2.9, 16 Hz, 1H), 2.31 (dd, J=9.0, 16 Hz, 1H), 1.47 (s, 9H), 1.19–1.30 (m, 2H), 0.88 (t, J=6.8 Hz, 3H)

Referential Example 12
Preparation of Intermediate (68)

To a suspension of 2.10 g of L-valine tert-butyl ester hydrochloride in 20 ml of DMF were added 3.1 ml of triethylamine and 5.7 ml of 1-bromododecane. The reaction solution was stirred at room temperature for 3 days, and then water was added and the mixture was extracted with ethyl acetate. The organic layer was dried over anhydrous sodium sulfate, the solvent was removed in vacuo, and then the crude product was subjected to column chromatography using silica gel and eluted with hexane:ethyl acetate=9:1 to afford 2.03 g of Intermediate (68).

$^1$H-NMR (δ ppm, CDCl$_3$) 2.82 (d, J=6.4 Hz, 1H), 2.55–2.60 (m, 1H), 2.39–2.45 (m, 1H), 1.81–1.89 (m, 1H), 1.48 (s, 9H), 1.20–1.63 (m, 20H), 0.94 (t, J=6.4 Hz, 6H), 0.88 (t, J=7.2 Hz, 3H)

Referential Example 13
Preparation of Intermediate (97)

To a 40% ethanolic solution (15 ml) of sodium cyanide (1.84 g) was added a 40% ethanolic solution of (R)-(+)-1,2-epoxy-3-undecyloxypropane (2.71 g). The reaction solution was heated under reflux for 8 hours and then the ethanol was removed in vacuo. The residue was adjusted to pH 4 by the addition of 1N hydrochloric acid under ice-cooling and extracted with chloroform. The combined chloroform layers were dried over anhydrous sodium sulfate and then the solvent was removed in vacuo. The resulting crude product was purified by a short column to afford an intermediate carboxylic acid.

A solution of the carboxylic acid thus obtained, triethylamine (0.89 ml) and benzyl bromide (0.76 ml) in dimethylformamide (15 ml) was stirred at room temperature for 2 days. After the solvent was removed in vacuo, ethyl acetate and water were added to the residue. The separated ethyl acetate layer was washed twice with water and then dried over anhydrous sodium sulfate. After the ethyl acetate was removed in vacuo, the residue was purified by a silica gel column chromatography (silica gel 30 g, hexane:ethyl acetate=200:10–40) to afford 0.86 g of the desired Intermediate (97).

$^1$H-NMR (δ ppm, CDCl$_3$) 7.28–7.41 (m, 5H), 5.16 (s, 2H), 4.18–4.26 (m, 1H), 3.35–3.49 (m, 4H), 2.87 (br s, 1H), 2.58 (d, J=6.3 Hz, 2H), 1.56 (q, J=6.8 Hz, 2H), 1.20–1.35 (m, 16H), 0.88 (t, J=6.8 Hz, 3H)

Using the same procedures as described above, the following compound was prepared:
Intermediate (100)

$^1$H-NMR (δ ppm, CDCl$_3$) 7.29–7.42 (m, 5H), 5.16 (s, 2H), 3.97–4.07 (m, 1H), 2.84 (br s, 1H), 2.56 (dd, J=3.2, 16 Hz, 1H), 2.46 (dd, J=9.0, 17 Hz, 1H), 1.37–1.67 (m, 4H), 1.06–1.36 (m, 26H), 0.88 (t, J=6.8 Hz, 3H)

Example 1
Preparation of Compound (1)

To a solution of 3.78 g of Intermediate (3) obtained in Referential Example 3 in 50 ml of dichloromethane were added 2.10 g of tert-butoxycarbonyl-D-leucine monohydrate and 1.25 g of HOBt and then 1.78 g of WSCI was added under ice-cooling. The reaction mixture was stirred under ice-cooling for one hour and then at room temperature overnight. After the solvent was removed in vacuo, the residue was dissolved in ethyl acetate. The solution was washed in turn with 10% aqueous citric acid, is water, 5% aqueous sodium hydrogencarbonate and water and then dried over anhydrous sodium sulfate. After the solvent was removed in vacuo, the residue was subjected to column chromatography using silica gel (80 g) and eluted with hexane:ethyl acetate=200:10–25 to afford 5.58 g of Compound (1).

$^1$H-NMR (δ ppm, CDCl$_3$) 7.30–7.39 (m, 5H), 6.60–6.70 (m, 1H), 5.25–5.30 (m, 1H), 5.07–5.14 (m, 2H), 4.75–4.95 (m, 1H), 4.45–4.55 (m, 1H), 4.10–4.20 (m, 1H), 2.55–2.71 (m, 2H), 1.80–1.95 (m, 1H), 1.50–1.70 (m, 3H), 1.35–1.50 (m, 2H), 1.45 (2s, 9H), 1.20–1.35 (m, 19H), 1.00–1.20 (m, 1H), 0.85–0.95 (m, 15H)

Using the same procedures as described above, the following compounds were prepared:
Compound (4)

$^1$H-NMR (δ ppm, CDCl$_3$) 7.30–7.40 (m, 10H), 6.75–6.90 (m, 2H), 5.67 (d, J=7.8 Hz, 1H), 5.20–5.30 (m, 1H), 5.04–5.16 (m, 4H), 4.48–4.60 (m, 3H), 3.13–3.20 (m, 1H), 2.56–2.81 (m, 3H), 1.75–1.95 (m, 2H), 1.45–1.70 (m, 2H), 1.35–1.45 (m, 2H), 1.45 (s, 9H), 1.10–1.35 (m, 20H), 0.80–0.90 (m, 15H)

Compound (8)

$^1$H-NMR (δ ppm, CDCl$_3$) 7.30–7.40 (m, 10H), 7.23 (t, J=9.3 Hz, 1H), 7.05–7.15 (m, 1H), 6.84 (d, J=6.8 Hz, 1H), 5.21–5.28 (m, 1H), 5.04–5.20 (m, 4H), 4.85–5.00 (m, 2H), 4.40–4.50 (m, 2H), 3.89 (t, J=6.1 Hz, 1H), 3.15–3.21 (m, 1H), 2.67–2.81 (m, 2H), 2.55–2.62 (m, 1H), 2.10–2.20 (m, 1H), 1.70–1.90 (m, 2H), 1.50–1.70 (m, 2H), 1.00–1.50 (m, 22H), 1.43 (s, 9H), 0.80–1.00 (m, 15H), 0.96 (d, J=6.8 Hz, 3H), 0.91 (d, J=6.8 Hz, 3H)

Compound (12)

$^1$H-NMR (δ ppm, CDCl$_3$) 7.15–7.45 (m, 12H), 6.85–6.95 (m, 1H), 6.80–6.85 (m, 1H), 6.00–6.10 (m, 1H), 5.20–5.30 (m, 1H), 5.05–5.15 (m, 4H), 4.60–4.70 (m, 1H), 4.35–4.45 (m, 2H), 4.10–4.20 (m, 1H), 3.91 (br s, 1H), 3.10–3.20 (m, 1H), 2.95–3.05 (m, 1H), 2.65–2.75 (m, 1H), 2.55–2.62 (m, 1H), 2.05–2.15 (m, 1H), 1.50–1.90 (m, 5H), 1.00–1.50 (m, 24H), 1.42, 1.43 (2s, 9H), 0.80–1.00 (m, 27H)

Compound (16)

$^1$H-NMR (δ ppm, CDCl$_3$) 7.30–7.40 (m, 5H), 7.04 (br s, 1H), 5.72 (br s, 1H), 5.20–5.30 (m, 1H), 5.14, 5.15 (2s, 2H), 4.45–4.55 (m, 2H), 3.66 (s, 3H), 3.04 (dd, J=4.4, 17 Hz, 1H), 2.73 (dd, J=5.9, 17 Hz, 1H), 2.50–2.66 (m, 2H), 1.80–1.90 (m, 1H), 1.50–1.70 (m, 2H), 1.45 (s, 9H), 1.10–1.50 (m, 20H), 0.85–0.95 (m, 9H)

Compound (22)

$^1$H-NMR (δ ppm, CDCl$_3$) 7.30–7.40 (m, 5H), 6.70–6.80 (m, 2H), 5.67 (br s, 1H), 5.20–5.30 (m, 1H), 5.16 (d, J=12 Hz), 5.08 (d, J=12 Hz), 4.45–4.60 (m, 3H), 3.65 (2s, 3H), 3.10–3.20 (m, 1H), 2.75–2.85 (m, 1H), 2.50–2.65 (m, 2H), 1.70–1.95 (m, 2H), 1.45–1.70 (m, 4H), 1.45 (s, 9H), 1.00–1.45 (m, 20H), 0.85–1.00 (m, 15H)

Compound (28)

$^1$H-NMR (δ ppm, CD$_3$OD) 7.25–7.35 (m, 5H), 7.13 (d, J=8.3 Hz, 4H), 6.80–6.85 (m, 4H), 6.08 (s, 1H), 5.05–5.30 (m, 3H), 4.20–4.35 (m, 3H), 3.76 (2s, 6H), 2.30–2.50 (m, 4H), 2.05–2.15 (m, 1H), 1.75–1.95 (m, 3H), 1.10–1.75 (m, 24H), 1.45 (s, 9H), 0.80–0.95 (m, 15H)

Compound (30)

¹H-NMR (δ ppm, CD₃OD) 7.25–7.40 (m, 5H), 7.10–7.20 (m, 4H), 6.80–6.90 (m, 4H), 6.05–6.10 (m, 1H), 5.15–5.30 (m, 1H), 5.00–5.15 (m, 2H), 4.40–4.50 (m, 2H), 4.20–4.40 (m, 2H), 3.76 (2s, 6H), 2.70–2.80 (m, 1H), 2.55–2.70 (m, 1H), 2.30–2.55 (m, 4H), 2.05–2.20 (m, 1H), 1.80–2.00 (m, 2H), 1.50–1.70 (m, 5H), 1.10–1.50 (m, 20H), 1.45 (2s, 9H), 1.42 (2s, 9H), 0.80–0.95 (m, 15H)

Compound (32)

¹H-NMR (δ ppm, CD₃OD) 7.25–7.40 (m, 5H), 7.15(d, J=8.3 Hz, 4H), 6.84–6.86 (m, 4H), 6.09 (d, J=3.4 Hz, 1H), 5.10–5.30 (m, 2H), 5.00–5.10 (m, 1H), 4.60–4.70 (m, 1H) 4.20–4.50 (m, 3H), 3.85–3.90 (m, 1H), 3.77 (s, 6H), 2.80–2.95 (m, 1H), 2.65–2.80 (m, 1H), 2.30–2.65 (m, 4H), 1.80–2.20 (m, 4H), 1.50–1.80 (m, 5H), 1.10–1.50 (m, 20H), 1.45 (s, 9H), 1.43 (s, 9H), 0.84–0.95 (m, 21H)

Compound (34)

¹H-NMR (δ ppm, CD₃OD) 7.25–7.38 (m, 5H), 7.14 (d, J=8.3 Hz, 4H), 6.85 (d, J=8.8 Hz, 4H), 6.08 (s, 1H), 5.20–5.30 (m, 1H), 5.10–5.20 (m, 2H), 4.20–4.40 (m, 3H), 3.78 (2s, 6H), 2.30–2.55 (m, 4H), 2.10–2.20 (m, 1H), 1.80–2.00 (m, 2H), 1.40–1.75 (m, 5H), 1.45, 1.46 (2s, 9H), 1.10–1.40 (m, 20H), 0.80–0.95 (m, 15H)

Compound (36)

¹H-NMR (δ ppm, CD₃OD) 7.25–7.35 (m, 5H), 7.13 (d, J=7.3 Hz, 4H), 6.85 (d, J=8.3 Hz, 4H), 6.08 (s, 1H), 5.05–5.30 (m, 3H), 4.40–4.50 (m, 2H), 4.20–4.35 (m, 2H), 3.77 (s, 6H), 2.70–2.80 (m, 1H), 2.30–2.60 (m, 5H), 2.05–2.15 (m, 1H), 1.80–1.95 (m, 2H), 1.50–1.70 (m, 5H), 1.45 (s, 9H), 1.41 (s, 9H), 1.10–1.50 (m, 20H), 0.80–0.95 (m, 15H)

Compound (38)

¹H-NMR (δ ppm, CD₃OD) 7.25–7.40 (m, 5H), 7.14 (d, J=8.8 Hz, 4H), 6.85 (d, J=8.3 Hz, 4H), 6.08 (s, 1H), 5.05–5.30 (m, 3H), 4.60–4.70 (m, 1H), 4.40–4.50 (m, 1H), 4.20–4.35 (m, 2H), 3.85–3.95 (m, 1H), 3.77 (s, 3H), 3.76 (s, 3H), 2.45–2.85 (m, 3H), 2.30–2.45 (m, 3H), 1.85–2.20 (m, 4H), 1.50–1.70 (m, 5H), 1.15–1.50 (m, 38H), 0.80–1.00 (m, 21H)

Compound (40)

¹H-NMR (δ ppm, CDCl₃) 7.74–7.77 (m, 2H), 7.51–7.60 (m, 2H), 7.27–7.41 (m, 4H), 7.00–7.22 (m, 5H), 6.78–6.88 (m, 4H), 6.18–6.26 (m, 1H), 5.35–5.90 (m, 1H), 5.20–5.30 (m, 1H), 4.72–4.91 (m, 1H), 4.25–4.60 (m, 6H), 4.14–4.22 (m, 1H), 3.77 (s, 3H), 3.76 (s, 3H), 1.84–2.84 (m, 12H), 1.14–1.80 (m, 46H), 0.86–0.92 (m, 15H)

Compound (43)

¹H-NMR (δ ppm, CDCl₃) 7.74–7.77 (m, 2H), 7.51–7.60 (m, 2H), 7.29–7.42 (m, 6H), 7.12–7.24 (m, 4H), 6.79–7.03 (m, 4H), 6.18–6.26 (m, 1H), 5.46–5.50 (m, 1H), 4.53–5.20 (m, 2H), 4.28–4.47 (m, 5H), 4.01–4.24 (m, 2H), 3.68–3.81 (m, 7H), 2.27–2.85 (m, 5H), 1.79–2.20 (m, 6H), 1.08–1.63 (m, 48H), 0.77–0.88 (m, 21H)

Compound (45)

¹H-NMR (δ ppm, CDCl₃) 6.34–7.76 (m, 22H), 6.20–6.23 (m, 1H), 5.15–5.20 (m, 1H), 4.18–4.64 (m, 8H), 3.77 (s, 3H), 3.75 (s, 3H), 2.67–2.78 (m, 2H), 2.33–2.48 (m, 4H), 1.80–2.07 (m, 3H), 1.16–1.54 (m, 45H), 0.77–0.92 (m, 24H)

Compound (48)

¹H-NMR (δ ppm, CDCl₃) 6.80–7.76 (m, 22H), 6.18–6.20 (m, 1H), 5.67–5.85 (m, 1H), 5.11–5.16 (m, 1H), 4.85–4.91 (m, 1H), 4.19–4.52 (m, 7H), 3.93–3.97 (m, 1H), 3.77 (s, 3H), 3.76 (s, 3H), 2.70–2.84 (m, 2H), 2.29–2.51 (m, 4H), 1.79–2.10 (m, 5H), 1.12–1.58 (m, 44H), 0.80–0.95 (m, 30H)

Compound (50)

¹H-NMR (δ ppm, CDCl₃) 7.73–7.76 (m, 2H), 7.47–7.61 (m, 3H), 6.53–7.43 (m, 26H), 6.06–6.36 (m, 2H), 4.91–5.22 (m, 1H), 4.10–4.56 (m, 8H), 3.67–3.79 (m, 12H), 1.07–2.46 (m, 48H), 0.76–0.92 (m, 21H)

Compound (53)

¹H-NMR (δ ppm, CDCl₃) 7.73–7.76 (m, 2H), 7.49–7.62 (m, 3H), 6.51–7.43 (m, 27H), 6.03–6.34 (m, 2H), 5.07–5.22 (m, 1H), 4.09–4.55 (m, 9H), 3.65–3.80 (m, 12H), 1.07–2.46 (m, 49H), 0.77–0.94 (m, 27H)

Compound (55)

¹H-NMR (δ ppm, CDCl₃) 6.47–7.77 (m, 22H), 6.20–6.24 (m, 1H), 5.84 (d, J=7.3 Hz, 1H), 5.15–5.19 (m, 1H), 4.17–4.61 (m, 9H), 3.74–3.76 (m, 6H), 2.33–3.01 (m, 8H), 2.08–2.11 (m, 2H), 1.03–1.77 (m, 53H), 0.79–0.90 (m, 15H)

Compound (58)

¹H-NMR (δ ppm, d₆-DMSO) 6.77–8.53 (m, 23H), 6.00–6.03 (m, 1H), 5.09–5.15 (m, 1H), 4.10–4.35 (m, 8H), 3.85–3.89 (m, 1H), 3.72 (s, 3H), 3.71 (s, 3H), 2.21–2.96 (m, 8H), 1.08–1.97 (m, 54H), 0.78–0.90 (m, 21H)

Compound (60)

¹H-NMR (δ ppm, CDCl₃) 7.71–7.78 (m, 2H), 7.11–7.63 (m, 12H), 6.77–7.09 (m, 6H), 6.01–6.26 (m, 2H), 5.05–5.26 (m, 1H), 4.74–4.87 (m, 1H), 4.15–4.63 (m, 7H), 3.48–3.81 (m, 8H), 2.75–2.91 (m, 1H), 2.22–2.67 (m, 5H), 1.05–2.18 (m, 50H), 0.76–0.95 (m, 15H)

Compound (62)

¹H-NMR (δ ppm, CDCl₃) 6.81–7.76 (m, 22H), 6.17–6.21 (m, 1H), 5.64–5.83 (m, 1H), 5.10–5.16 (m, 1H), 4.83–4.92 (m, 1H), 4.18–4.51 (m, 7H), 3.86–3.96 (m, 1H), 2.04–2.78 (m, 8H), 1.08–1.71 (m, 48H), 0.81–0.99 (m, 27H)

Compound (72)

¹H-NMR (δ ppm, CDCl₃) 7.73–7.78 (m, 2H), 7.55–7.59 (m, 2H), 7.14–7.44 (m, 8H), 6.79–7.06 (m, 7H), 6.61 (d, J=7 Hz, 1H), 6.19–6.23 (m, 1H), 5.63 (d, J=7.8 Hz, 1H), 5.16–5.20 (m, 1H), 4.55–4.64 (m, 2H), 4.16–4.46 (m, 6H), 3.90–3.96 (m, 1H), 3.00–3.06 (m, 2H), 2.29–2.77 (m, 6H), 2.03–2.11 (m, 3H), 1.71–1.85 (m, 1H), 1.24–1.69 (m, 43H), 0.82–0.90 (m, 21H)

Compound (74)

¹H-NMR (δ ppm, CDCl₃) 7.33–7.78 (m, 2H), 7.55–7.62 (m, 2H), 7.26–7.42 (m, 4H), 7.11–7.18 (m, 4H), 6.78–6.84 (m, 5H), 6.16–6.21 (m, 1H), 5.70–5.94 (m, 1H), 5.02–5.30 (m, 1H), 4.24–4.78 (m, 7H), 4.19–4.22 (m, 1H), 3.99–4.03 (m, 1H), 3.76, 3.77 (s, 3H), 3.75, 3.77 (s, 3H), 2.01–2.25 (m, 6H), 1.40, 1.42 (s, 18H), 1.12–1.99 (m, 34H), 0.77–0.91 (m, 27H)

Compound (76)

¹H-NMR (δ ppm, d₆-DMSO) 7.66–8.52 (m, 11H), 7.38–7.41 (m, 2H), 7.28–7.32 (m, 2H), 7.13 (d, J=8.3 Hz, 4H), 6.84 (d, J=8.3 Hz, 4H), 6.00 (d, J=8.3 Hz, 4H), 5.04–5.11 (m, 1H), 4.61–4.65 (m, 1H), 4.09–4.36 (m, 7H), 3.80–3.84 (m, 1H), 3.72 (s, 3H), 3.71 (s, 3H), 1.10–2.46 (m, 38H), 1.37 (s, 9H), 1.36 (s, 9H), 0.75–0.89 (m, 27H)

Compound (78)

¹H-NMR (δ ppm, CDCl₃) 6.82–7.77 (m, 14H), 5.50–5.67 (m, 1H), 5.13–5.20 (m, 1H), 4.08–4.68 (m, 9H), 3.76–3.77 (m, 6H), 3.66–3.72 (m, 1H), 3.40–3.45 (m, 1H), 2.07–2.42 (m, 6H), 1.09–1.84 (m, 48H), 0.80–0.97 (m, 27H)

Compound (80)

¹H-NMR (δ ppm, d₆-DMSO) 6.82–8.67 (m, 32H), 5.99–6.02 (m, 2H), 5.04–5.10 (m, 1H), 4.63–4.65 (m, 1H), 4.11–4.31 (m, 7H), 3.87–3.89 (m, 1H), 3.67–3.71 (m, 12H), 2.22–2.89 (m, 8H), 1.20–1.96 (m, 39H), 0.71–0.89 (m, 27H)

Compound (82)

¹H-NMR (δ ppm, CDCl₃) 7.72–7.74 (m, 2H), 6.73–7.57 (m, 24H), 6.16–6.21 (m, 1H), 5.56–5.72 (m, 1H), 5.09–5.17 (m, 1H), 4.78–4.89 (m, 1H), 4.08–4.52 (m, 7H), 3.75 (s, 6H), 3.60–3.80 (m, 1H), 3.14–3.20 (m, 1H), 2.92–3.01 (m, 3H), 1.42 (s, 9H), 1.39 (s, 9H), 1.16–2.43 (m, 35H), 0.81–0.90 (m, 21H)

Compound (95)

¹H-NMR (δ ppm, CDCl₃) 7.76 (d, J=7.8 Hz, 2H), 7.56–7.76 (m, 2H), 7.29–7.56 (m, 10H), 7.05–7.08 (m, 1H), 6.63–6.67 (m, 1H), 5.35–5.38 (m, 1H), 5.24–5.30 (m, 1H), 5.06–5.13 (m, 2H), 4.68–4.73 (m, 1H), 3.93–4.51 (m, 6H), 2.54–2.70 (m, 4H), 2.15–2.19 (m, 1H), 1.03–1.94 (m, 35H), 0.86–1.00 (m, 21H)

Compound (98)

¹H-NMR (δ ppm, d₆-DMSO) 8.50 (d, J=8.8 Hz, 1H), 8.20 (d, J=8.3 Hz, 1H), 7.63–8.07 (m, 8H), 7.38–7.42 (m, 2H), 7.28–7.33 (m, 3H), 7.13 (d, J=8.8 Hz, 4H), 6.83–6.85 (m, 4H), 6.01 (d, J=8.5 Hz, 1H), 5.06–5.11 (m, 1H), 4.57–4.61 (m, 1H), 4.09–4.42 (m, 7H), 3.86–3.90 (m, 1H), 3.71 (s, 6H), 2.21–2.70 (m, 8H), 1.22–1.98 (m, 48H), 0.77–0.90 (m, 27H)

Compound (100)

¹H-NMR (δ ppm, CDCl₃) 7.26–7.77 (m, 13H), 6.71–6.92 (m, 2H), 5.97 (d, J=7.6 Hz, 1H), 5.23–5.29 (m, 1H), 5.02–5.15 (m, 2H), 4.39–4.57 (m, 5H), 4.20–4.24 (m, 1H), 2.53–2.98 (m, 4H), 1.16–1.84 (m, 35H), 0.84–0.99 (m, 15H)

Compound (102)

¹H-NMR (δ ppm, CDCl₃) 7.75 (d, J=7.6 Hz, 2H), 7.56 (d, J=7.6 Hz, 2H), 7.24–7.42 (m, 10H), 6.93–7.07 (m, 1H), 6.77–6.86 (m, 1H), 5.19–5.331 (m, 1H), 5.02–5.14 (m, 2H), 4.41–4.78 (m, 5H), 4.16–4.31 (m, 1H), 3.63–3.81 (m, 1H), 2.88–3.07 (m, 2H), 2.25–2.77 (m, 4H), 1.40, 1.43 (2s, 9H), 1.06–1.96 (m, 47H), 0.67–0.97 (m, 24H)

Compound (108)

¹H-NMR (δ ppm, CDCl₃) 6.71–7.76 (m, 21H), 6.19–6.29 (m, 2H), 5.16–5.18 (m, 1H), 4.19–4.68 (m, 8H), 3.73–3.78 (m, 6H), 1.08–2.79 (m, 55H), 0.79–0.91 (m, 21H)

Compound (110)

¹H-NMR (δ ppm, CDCl₃) 6.74–7.41 (m, 20H), 6.19–6.22 (m, 1H), 5.59–5.78 (m, 1H), 4.85–5.17 (m, 4H), 4.30–4.53 (m, 3H), 3.94–4.00 (m, 1H), 3.76–3.78 (m, 6H), 2.73–2.75 (m, 2H), 2.29–2.45 (m, 4H), 2.04–2.09 (m, 3H), 1.08–1.75 (m, 47H), 0.81–0.97 (m, 27H)

Compound (112)

¹H-NMR (δ ppm, CDCl₃) 7.27–7.76 (m, 13H), 6.99 (br, 1H), 6.91 (br, 2H), 6.83 (br, 1H), 5.57 (br, 1H), 5.19–5.24 (m, 1H), 5.02–5.10 (m, 2H), 3.95–4.85 (m, 7H), 2.46–2.86 (m, 4H), 1.08–2.11 (m, 36H), 0.85–0.95 (m, 21H)

Compound (115)

¹H-NMR (δ ppm, CDCl₃) 7.78–7.71 (m, 2H), 5.84–7.66 (m, 12H), 3.85–5.59 (m, 9H), 2.30–3.18 (m, 6H), 1.08–2.18 (m, 60H), 0.73–1.02 (m, 21H)

Compound (117)

¹H-NMR (δ ppm, CDCl₃) 7.75–7.78 (m, 2H), 7.60–7.65 (m, 2H), 7.00–7.41 (m, 10H), 5.07–5.17 (m, 1H), 4.87–4.94 (m, 1H), 3.99–4.52 (m, 8H), 2.77–2.82 (m, 2H), 2.34–2.53 (m, 4H), 2.07–2.12 (m, 2H), 1.39–1.96 (m, 37H), 1.08–1.30 (m, 20H), 0.86–1.01 (m, 27H)

Compound (119)

¹H-NMR (δ ppm, CDCl₃) 7.75–7.77 (m, 2H), 7.60–7.63 (m, 2H), 6.79–7.52 (m, 9H), 5.67–5.81 (m, 1H), 5.05–5.20 (m, 1H), 4.87–4.99 (m, 1H), 3.86–4.53 (m, 8H), 2.75–2.82 (m, 2H), 2.36–2.52 (m, 2H), 2.10–2.15 (m, 1H), 1.05–1.94 (m, 47H), 0.86–0.99 (m, 30H)

Compound (121)

¹H-NMR (δ ppm, CDCl₃) 7.00–7.78 (m, 14H), 3.66–5.11 (m, 10H), 2.13–2.84 (m, 6H), 1.22–1.70 (m, 57H), 0.86–1.00 (m, 27H)

Compound (123)

¹H-NMR (δ ppm, CDCl₃) 7.28–7.77 (m, 9H), 6.67–6.95 (m, 2H), 5.95–5.97 (m, 1H), 5.17–5.25 (m, 1H), 4.21–4.57 (m, 6H), 2.40–2.97 (m, 4H), 1.22–1.93 (m, 44H), 0.83–0.93 (m, 15H)

Compound (125)

¹H-NMR (δ ppm, CDCl₃) 6.84–7.76 (m, 9H), 4.46–5.42 (m, 7H), 2.08–2.59 (m, 4H), 1.13–1.93 (m, 45H), 0.86–1.02 (m, 21H)

Compound (127)

¹H-NMR (δ ppm, CDCl₃) 6.83–7.82 (m, 12H), 5.15–5.22 (m, 1H), 3.96–4.90 (m, 7H), 2.31–2.93 (m, 4H), 1.19–2.15 (m, 45H), 0.86–1.01 (m, 21H)

Compound (133)

¹H-NMR (δ ppm, CDCl₃) 7.72–7.80 (m, 2H), 7.51–7.66 (m, 3H), 7.05–7.44 (m, 7H), 6.90–7.03 (m, 1H), 5.66–5.80 (m, 1H), 5.02–5.18 (m, 1H), 4.71–4.92 (m, 2H), 4.29–4.63 (m, 5H), 4.18–4.26 (m, 1H), 3.99–4.07 (m, 1H), 2.64–2.88 (m, 4H), 2.27–2.49 (m, 4H), 1.33–2.22 (m, 65H), 0.81–1.02 (m, 21H)

Compound (135)

¹H-NMR (δ ppm, CDCl₃) 7.73–7.88 (m, 3H), 7.56–7.64 (m, 2H), 7.27–7.48 (m, 5H), 6.72–7.18 (m, 2H), 6.29–6.42 (m, 1H), 5.06–5.20 (m, 1H), 4.58–4.90 (m, 2H), 4.19–4.56 (m, 5H), 2.66–3.05 (m, 4H), 2.31–2.60 (m, 4H), 2.04–2.17 (m, 1H), 1.88–1.99 (m, 1H), 1.17–1.74 (m, 59H), 0.83–0.97 (m, 9H)

Compound (137)

¹H-NMR (δ ppm, CDCl₃) 8.38–8.45 (m, 1H), 7.46–7.78 (m, 1H), 7.00–7.16 (m, 1H), 6.86–6.70 (m, 1H), 5.07–5.18 (m, 1H), 4.71–4.86 (m, 2H), 4.35–4.52 (m, 2H), 3.64–3.71 (m, 1H), 2.61–2.95 (m, 6H), 2.34–2.57 (m, 4H), 2.06–2.18 (m, 1H), 1.88–1.99 (m, 1H), 1.19–1.73 (m, 68H), 0.86–0.95 (m, 9H)

Compound (139)

¹H-NMR (δ ppm, CDCl₃) 7.74–7.80 (m, 2H), 7.27–7.67 (m, 9H), 6.96–7.08 (m, 2H), 5.72–5.92 (m, 1H), 5.04–5.19 (m, 1H), 4.71–4.94 (m, 3H), 4.29–4.54 (m, 4H), 4.18–4.23 (m, 1H), 4.01–4.11 (m, 1H), 2.64–2.88 (m, 6H), 2.29–2.55 (m, 4H), 1.17–2.24 (m, 71H), 0.82–1.04 (m, 15H)

Compound (141)

¹H-NMR (δ ppm, CDCl₃) 7.27–7.78 (m, 11H), 6.90–7.08 (m, 2H), 6.09–6.18 (m, 1H), 5.06–5.19 (m, 1H), 4.70–4.90 (m, 3H), 4.32–4.61 (m, 5H), 4.21–4.25 (m, 1H), 2.68–2.91 (m, 8H), 2.28–2.56 (m, 4H), 2.03–2.16 (m, 1H), 1.86–1.98 (m, 1H), 1.17–1.76 (m, 77H), 0.84–0.95 (m, 9H)

Compound (143)

¹H-NMR (δ ppm, CDCl₃) 7.75 (d, J=8.0 Hz, 2H), 7.57–7.65 (m, 2H), 7.27–7.43 (m, 10H), 5.96–6.09 (m, 1H), 5.24–5.28 (m, 1H), 5.10, 5.12 (2s, 2H), 4.65–4.74 (m, 1H), 4.53–4.64 (m, 1H), 4.33–4.44 (m, 2H), 4.22–4.26 (m, 1H), 2.51–2.92 (m, 6H), 1.45 (s, 9H), 1.38, 1.40 (2s, 9H), 1.17–1.69 (m, 20H), 0.87 (t, J=7.2 H, 3H)

Compound (145)

¹H-NMR (δ ppm, CDCl₃) 7.75 (d, J=8.0 Hz, 2H), 7.68, 7.80 (2d, J=8.8 Hz, 1H), 7.53–7.65 (m, 2H), 7.27–7.45 (m, 10H), 6.05, 6.33 (2d, J=8.4 Hz, 1H), 5.19–5.30 (m, 1H), 5.03–5.08 (m, 2H), 4.55–4.88 (m, 3H), 4.33–4.42 (m, 2H), 4.17–4.28 (m, 1H), 2.50–3.06 (m, 8H), 1.12–1.69 (m, 47H), 0.88 (t, J=7.2 Hz, 3H)

Compound (147)

¹H-NMR (δ ppm, CDCl₃) 7.51–7.77 (m, 6H), 7.27–7.42 (m, 10H), 5.92–5.98 (m, 1H), 5.19–5.28 (m, 1H), 5.09, 5.10 (2s, 2H), 4.69–4.88 (m, 3H), 4.50–4.60 (m, 1H), 4.32–4.43 (m, 2H), 4.18–4.25 (m, 1H), 2.49–2.97 (m, 10H), 1.14–1.72 (m, 56H), 0.87 (t, J=6.8 Hz, 3H)

Compound (150)

¹H-NMR (δ ppm, CDCl₃) 7.32–7.78 (m, 7H), 7.39 (t, J=7.2 Hz, 2H), 7.30 (t, J=7.2 Hz, 2H), 7.06–7.19 (m, 2H), 6.11 (d, J=8.4 Hz, 1H), 5.08–5.20 (m, 1H), 4.33–4.93 (m, 8H), 4.23 (t, J=7.2 Hz, 1H), 2.61–2.96 (m, 10H), 2.30–2.54 (m, 4H), 2.06–2.17 (m, 1H), 1.86–1.98 (m, 1H), 1.16–1.81 (m, 20H), 0.87 (t, J=6.8 Hz, 3H)

Compound (152)

¹H-NMR (δ ppm, CDCl₃) 7.75 (d, J=7.8 Hz, 2H), 6.69–7.61 (m, 22H), 6.78–6.82 (m, 4H), 6.14, 6.19 (2d, J=7.8 Hz, 1H), 5.62–5.94 (m, 1H), 4.77–5.19 (m, 4H), 4.17–4.61 (m, 8H), 3.96–4.06 (m, 1H), 3.72, 3.74 (2s, 6H), 2.64–2.81 (m, 2H), 2.24–2.44 (m, 4H), 1.92–2.18 (m, 3H), 1.68 (s, 9H), 1.19–1.89 (m, 32H), 0.81–0.93 (m, 33H)

Compound (155)

¹H-NMR (δ ppm, CDCl₃) 7.75 (dd, J=3.4, 7.8 Hz, 2H), 7.60 (dd, J=7.8, 10 Hz, 2H), 7.38 (dt, J=2.4, 7.6 Hz, 2H), 7.15 (t, J=9.0 Hz, 4H), 7.21–7.42 (m, 5H), 7.03–7.10 (m, 1H), 6.97 (d, J=7.3 Hz, 1H), 6.81 (d, J=8.8 Hz, 4H), 6.78–6.84 (m, 1H), 6.19 (d, J=8.3 Hz, 1H), 5.77 (d, J=5.4 Hz, 1H), 5.13 (br s, 1H), 4.81–4.89 (m, 1H), 4.29–4.49 (m, 6H), 4.20 (t, J=6.8 Hz, 1H), 3.91–3.99 (m, 1H), 3.76 (s, 6H), 2.77 (t, J=5.6 Hz, 2H), 2.24–2.42 (m, 4H), 1.99–2.15 (m, 3H), 1.80–1.90 (m, 1H), 1.43 (s, 9H), 1.41 (s, 9H), 1.11–1.78 (m, 28H), 0.73–1.00 (m, 27H)

Compound (157)

¹H-NMR (δ ppm, CDCl₃) 7.75 (d, J=7.8 Hz, 2H), 7.55–7.62 (m, 2H), 7.45 (d, J=7.8 Hz, 1H), 7.39 (t, J=7.3 Hz, 2H), 7.30 (t, J=7.6 Hz, 2H), 7.18 (d, J=8.3 Hz, 2H), 7.14 (d, J=8.3 Hz, 2H), 7.10–7.35 (m, 3H), 6.99 (d, J=6.3 Hz, 1H), 6.82 (dd, J=2.4, 8.8 Hz, 4H), 6.80–6.90 (m, 1H), 6.19 (d, J=8.3 Hz, 1H), 5.61 (d, J=7.3 Hz, 1H), 5.12–5.21 (m, 1H), 4.87–4.95 (m, 1H), 4.27–4.54 (m, 6H), 4.16–4.24 (m, 1H), 3.93–4.05 (m, 1H), 3.77 (2s, 6H), 2.75 (d, J=5.9 Hz, 2H), 2.26–2.51 (m, 4H), 1.99–2.17 (m, 3H), 1.68–1.84 (m, 1H), 1.43 (s, 9H), 1.40 (s, 9H), 1.05–1.67 (m, 28H), 0.76–0.98 (m, 27H)

Compound (160)

¹H-NMR (δ ppm, CDCl₃) 7.52–7.82 (m, 6H), 7.27–7.44 (m, 5H), 6.95–7.24 (m, 6H), 6.73–6.89 (m, 5H), 6.12–6.26 (m, 1H), 5.41–5.77 (m, 1H), 5.10–5.35 (m, 1H), 4.91–5.09 (m, 1H), 3.90–4.64 (m, 8H), 3.28–3.81 (m, 8H), 1.09–2.92 (m, 57H), 0.72–0.99 (m, 21H)

Compound (162)

¹H-NMR (δ ppm, CDCl₃) 7.74 (d, J=7.3 Hz, 2H), 7.61 (t, J=8.1 Hz, 2H), 7.38 (t, J=6.8 Hz, 2H), 7.22–7.36 (m, 7H), 7.14 (d, J=6.8 Hz, 1H), 7.00 (d, J=5.9 Hz, 1H), 6.83 (d, J=7.3 Hz, 1H), 5.55 (d, J=5.4 Hz, 1H), 5.33–5.44 (m, 1H), 5.01–5.15 (m, 2H), 4.75–4.89 (m, 1H), 4.35–4.55 (m, 4H), 4.22 (t, J=6.6 Hz, 1H), 3.93 (br s, 1H), 3.50 (dd, J=5.6, 11 Hz, 1H), 3.44 (dd, J=4.4, 11 Hz, 1H), 3.25–3.41 (m, 2H), 2.86 (dd, J=5.9, 17 Hz, 1H), 2.70–2.80 (m, 1H), 2.66 (d, J=6.3 Hz, 2H), 2.06–2.19 (m, 1H), 1.71–1.96 (m, 2H), 1.42 (s, 9H), 1.13–1.70 (m, 22H), 0.78–1.04 (m, 21H)

Compound (165)

¹H-NMR (δ ppm, CDCl₃) 7.74 (d, J=7.3 Hz, 2H), 7.61 (t, J=6.8 Hz, 2H), 7.23–7.40 (m, 9H), 7.17 (d, J=7.3 Hz, 1H), 7.00 (br s, 1H), 6.81 (d, J=8.8 Hz, 1H), 5.58 (d, J=4.9 Hz, 1H), 5.30–5.57 (m, 1H), 4.99–5.16 (m, 2H), 4.75–4.91 (m, 1H), 4.33–4.63 (m, 4H), 4.21 (t, J=6.6 Hz, 1H), 3.93 (br s, 1H), 2.86 (dd, J=5.6, 18 Hz, 1H), 2.74 (dd, J=6.6, 17 Hz, 1H), 2.58–2.68 (m, 1H), 2.48 (dd, J=6.8, 15 Hz, 1H), 2.10 (br s, 1H), 1.91 (br s, 1H), 1.42 (s, 9H), 1.10–1.85 (m, 35H), 0.80–1.04 (m, 21H)

Example 2
Preparation of Compound (2)

To 5.48 g of Compound (1) obtained in Example 1 was added 9 ml of trifluoroacetic acid. The reaction mixture was stirred at room temperature for 15 minutes. After the solvent was removed, the residue was dissolved in ethyl acetate and washed with saturated aqueous sodium hydrogencarbonate. The organic layer was dried over anhydrous sodium sulfate and the solvent was removed in vacuo to afford 4.64 g of Compound (2).

¹H-NMR (δ ppm, CDCl₃) 7.90, 8.04 (2d, J=8.8 Hz, J=7.8 Hz, 1H), 7.30–7.38 (m, 5H), 5.24–5.29 (m, 1H), 5.12 (s, 1H), 5.10 (s, 1H), 4.42–4.50 (m, 1H), 3.70–3.82 (m, 1H), 3.20–3.85 (m, 2H), 2.56–2.73 (m, 2H), 1.82–1.95 (m, 1H), 1.45–1.75 (m, 5H), 1.35–1.45 (m, 1H), 1.10–1.35 (m, 19H), 0.82–0.97 (m, 15H)

Using the same procedures as described above, the following compounds were prepared:

Compound (6)

¹H-NMR (δ ppm, CDCl₃+CD₃OD) 7.25–7.35 (m, 10H), 7.17 (t, J=9.5 Hz, 1H), 5.20–5.30 (m, 1H), 5.05–5.17 (m, 4H), 4.40–4.50 (m, 2H), 3.69–3.72 (m, 1H), 2.79–2.96 (m, 2H), 2.56–2.73 (m, 2H), 1.80–2.00 (m, 2H), 1.70–1.80 (m, 1H), 1.50–1.70 (m, 4H), 1.00–1.45 (m, 19H), 0.80–0.95 (m, 15H)

Compound (10)

¹H-NMR (δ ppm, CDCl₃) 8.35–8.45 (m, 1H), 7.25–7.40 (m, 10H), 7.10–7.20 (m, 1H), 6.75–7.85 (m, 1H), 5.20–5.30 (m, 1H), 5.05–5.15 (m, 4H), 4.75–4.85 (m, 1H), 4.40–4.50 (m, 2H), 3.40 (br s, 1H), 2.95–3.00 (m, 1H), 2.82–2.89 (m, 1H), 2.65–2.72 (m, 1H), 2.55–2.61 (m, 1H), 2.15–2.25 (m, 1H), 1.45–2.15 (m, 9H), 1.00–1.45 (m, 19H), 0.80–1.00 (m, 21H)

Compound (14)

¹H-NMR (δ ppm, CD₃OD) 7.15–7.30 (m, 10H), 5.10–5.25 (m, 1H), 5.00–5.10 (m, 4H), 4.55–4.65 (m, 1H), 4.15–4.35 (m, 2H), 3.80–3.90 (m, 1H), 3.35–3.45 (m, 1H), 2.95–3.05 (m, 1H), 2.75–2.85 (m, 1H), 2.50–2.70 (m, 2H), 1.90–2.05 (m, 1H), 1.45–1.90 (m, 8H), 1.10–1.45 (m, 21H), 0.70–0.90 (m, 27H)

Compound (18)

¹H-NMR (δ ppm, CDCl₃) 7.85–7.90 (m, 1H), 7.30–7.40 (m, 5H), 5.20–5.30 (m, 1H), 5.15 (s, 1H), 5.14 (s, 1H), 4.50–4.55 (m, 1H), 3.70–3.80 (m, 1H), 3.66 (2s, 3H), 2.94 (dd, J=3.9, 17 Hz, 1H), 2.74 (ddd, J=2.3, 7.8, 17 Hz, 1H), 2.50–2.67 (m, 2H), 1.80–1.95 (m, 1H), 1.50–1.75 (m, 4H), 1.10–1.50 (m, 20H), 0.85–0.95 (m, 9H)

Example 3
Preparation of Compound (3)

In 70 ml of methanol was dissolved 0.50 g of Compound (2) obtained in Example 2 and 50 mg of 5% palladium-carbon was added to form a suspension. The resulting suspension was stirred under hydrogen atmosphere (1 atmospheric pressure) at room temperature for 3 hours. The catalyst was removed by filtration and the solvent was removed in vacuo from the filtrate to afford 0.41 g of Compound (3).

¹H-NMR (δ ppm, CDCl₃) 5.10–5.30 (m, 1H), 4.15, 4.43 (2d, J=8.3 Hz, J=6.8 Hz, 1H), 3.85–3.95 (m, 1H), 2.50–2.60 (m, 2H), 1.80–2.00 (m, 1H), 1.40–1.75 (m, 5H), 1.10–1.40 (m, 20H), 0.85–1.10 (m, 15H)

Using the same procedures as described above, the following compounds were prepared:

Compound (5)

¹H-NMR (δ ppm, CD₃OD) 5.10–5.20 (m, 1H), 4.38–4.45 (m, 2H), 4.29–4.34 (m, 1H), 2.75–2.78 (m, 2H), 2.57–2.61 (m, 2H), 1.93 (br s, 1H), 1.55–1.70 (m, 5H), 1.45 (s, 9H), 1.10–1.40 (m, 20H), 0.85–1.00 (m, 15H)

Compound (7)

¹H-NMR (δ ppm, CD₃OD) 5.20–5.30 (m, 1H), 4.55 (br s, 1H), 4.32–4.38 (m, 1H), 4.20 (br s, 1H), 2.85–2.95 (m, 2H), 2.50–2.65 (m, 2H), 1.91 (br s, 1H), 1.40–1.70 (m, 5H), 1.10–1.40 (m, 20H), 0.85–1.00 (m, 15H)

Compound (9)

¹H-NMR (δ ppm, CD₃OD) 5.10–5.20 (m, 1H), 4.50–4.60 (m, 1H), 4.15–4.30 (m, 2H), 3.75 (d, J=5.9 Hz, 1H), 2.70–2.80 (m, 2H), 2.40–2.55 (m, 2H), 1.90–2.05 (m, 1H), 1.75–1.90 (m, 1H), 1.45–1.70 (m, 5H), 1.38 (s, 9H), 1.00–1.40 (m, 20H), 0.70–0.90 (m, 21H)

Compound (11)
$^1$H-NMR (δ ppm, CD$_3$OD) 5.20–5.30 (m, 1H), 4.55–4.75 (m, 1H), 4.30–4.50 (m, 2H), 3.60–3.65 (m, 1H), 2.60–2.80 (m, 2H), 2.50–2.60 (m, 2H), 2.15–2.30 (m, 1H), 1.85–2.00 (m, 1H), 1.10–1.75 (m, 25H), 0.80–1.10 (m, 21H)

Compound (13)
$^1$H-NMR (δ ppm, CD$_3$OD) 5.20–5.30 (m, 1H), 4.54 (br s, 1H), 4.25–4.40 (m, 2H), 4.05–4.20 (m, 2H), 2.70–3.00 (m, 2H), 2.50–2.70 (m, 2H), 2.05–2.15 (m, 1H), 1.90–2.00 (m, 1H), 1.45 (s, 9H), 1.10–1.75 (m, 28H), 0.80–1.00 (m, 27H)

Compound (15)
$^1$H-NMR (δ ppm, CD$_3$OD) 5.25–5.35 (m, 1H), 4.55–4.65 (m, 1H), 4.45–4.55 (m, 1H), 4.10–4.25 (m, 2H), 3.98 (t, J=6.4 Hz, 1H), 2.79 (d, J=5.9 Hz, 2H), 2.45–2.55 (m, 2H), 2.15–2.25 (m, 1H), 1.85–1.95 (m, 1H), 1.55–1.85 (m, 7H), 1.40–1.55 (m, 1H), 1.10–1.40 (m, 20H), 0.80–1.10 (m, 27H)

Compound (17)
$^1$H-NMR (δ ppm, CDCl$_3$) 7.10–7.20(m, 1H), 5.71 (br s, 1H), 5.20–5.30 (m, 1H), 4.45–4.60 (m, 2H), 3.67 (2s, 3H), 2.90–3.00 (m, 1H), 2.65–2.75 (m, 1H), 2.50–2.65 (m, 2H), 2.70 (br s, 1H), 1.85–1.95 (m, 1H), 1.50–1.70 (m, 2H), 1.46 (s, 9H), 1.10–1.50 (m, 20H), 0.85–0.95 (m, 9H)

Compound (19)
$^1$H-NMR (δ ppm, CDCl$_3$) 8.30–8.50 (m, 1H), 5.20–5.30 (m, 1H), 4.35–4.45 (m, 2H), 3.65, 3.64 (2s, 3H), 2.70–2.80 (m, 1H), 2.50–2.70 (m, 3H), 2.60 (br s, 1H), 1.85–1.95 (m, 1H), 1.50–1.70 (m, 2H), 1.15–1.45 (m, 22H), 0.80–0.95 (m, 9H)

Compound (23)
$^1$H-NMR (δ ppm, CDCl$_3$) 6.70–7.10 (m, 2H), 5.75–5.85 (m, 1H), 5.20–5.30 (m, 1H), 4.40–4.60 (m, 3H), 3.71, 3.68 (2s, 3H), 3.15–3.30 (m, 1H), 2.55–2.75 (m, 3H), 2.20–3.00 (br m, 1H), 1.70–1.90 (m, 2H), 1.50–1.70 (m, 4H), 1.46 (s, 9H), 1.00–1.50 (m, 20H), 0.80–0.95 (m, 15H)

Compound (25)
$^1$H-NMR (δ ppm, CDCl$_3$) 8.65 (br s, 1H), 7.60 (br s, 1H), 5.20–5.30 (m, 1H), 4.25–4.45 (m, 3H), 3.66, 3.65 (2s, 3H), 2.20–2.90 (m, 7H), 1.80–1.95 (m, 1H), 1.50–1.70 (m, 5H), 1.10–1.40 (m, 20H), 0.75–1.00 (m, 15H)

Compound (27)
$^1$H-NMR (δ ppm, CDCl$_3$) 7.50–7.60 (m, 1H), 7.30–7.45 (m, 1H), 6.98, 7.19 (2d, J=8.8 Hz, J=8.3 Hz, 1H), 5.20–5.30 (m, 1H), 4.95–5.05 (m, 1H), 4.80–4.90 (m, 1H), 4.35–4.50 (m, 2H), 3.85–3.95 (m, 1H), 3.72, 3.68 (2s, 3H), 3.25–3.40 (m, 1H), 2.50–2.70 (m, 3H), 2.20–2.30 (m, 1H), 1.60 (br s, 1H), 1.50–1.90 (m, 6H), 1.43 (s, 9H), 1.00–1.50 (m, 23H), 0.80–1.00 (m, 18H)

Compound (29)
$^1$H-NMR (δ ppm, CD$_3$OD) 7.10–7.20 (m, 4H), 6.80–6.90 (m, 4H), 6.07 (s, 1H), 5.20–5.35 (m, 1H), 4.11–4.28 (m, 2H), 3.80–3.90 (m, 1H), 3.77 (s, 6H), 2.30–2.55 (m, 4H), 1.80–2.20 (m, 3H), 1.55–1.75 (m, 5H), 1.05–1.55 (m, 20H), 1.46 (s, 9H), 0.80–1.00 (m, 15H)

Compound (31)
$^1$H-NMR (δ ppm, CD$_3$OD) 7.10–7.18 (m, 4H), 6.80–6.90 (m, 4H), 6.09 (d, J=4.4 Hz, 1H), 5.15–5.30 (m, 1H), 4.25–4.50 (m, 3H), 3.77 (s, 6H), 3.60–3.65 (m, 1H), 2.30–2.70 (m, 6H), 2.10–2.20 (m, 1H), 1.80–2.20 (m, 2H), 1.50–1.70 (m, 5H), 1.15–1.50 (m, 20H), 1.46 (s, 9H), 1.45 (s, 9H), 0.85–0.95 (m, 15H)

Compound (35)
$^1$H-NMR (δ ppm, DCDl$_3$) 7.13 (d, J=7.8 Hz, 4H), 6.86 (d, J=8.8 Hz, 4H), 6.07 (s, 1H), 5.20–5.30 (m, 1H), 4.20–4.40 (m, 2H), 3.85–3.90 (m, 1H), 3.77 (s, 6H), 2.30–2.55 (m, 4H), 1.80–2.20 (m, 3H), 1.55–1.80 (m, 4H), 1.10–1.55 (m, 21H), 1.46 (s, 9H), 0.80–1.00 (m, 15H)

Compound (37)
$^1$H-NMR (δ ppm, CD$_3$OD) 7.13 (d, J=8.3 Hz, 4H), 6.86 (d, J=8.8 Hz, 4H), 6.07 (s, 1H), 5.15–5.30 (m, 1H), 4.50–4.55 (m, 1H), 4.15–4.35 (m, 3H), 3.77 (s, 6H), 2.95–3.00 (m, 1H), 2.70–2.77 (m, 1H), 2.30–2.60 (m, 4H), 2.00–2.15 (m, 1H), 1.80–2.00 (m, 2H), 1.50–1.75 (m, 5H), 1.49 (s, 9H), 1.46 (s, 9H), 1.10–1.40 (m, 20H), 0.85–1.05 (m,15H)

Compound (96)
$^1$H-NMR (δ ppm, DCDl$_3$) 9.55 (d, J=10 Hz, 0.5H), 8.57 (d, J=9 Hz, 0.5H), 6.80–7.86 (m, 12H), 5.48–5.51 (m, 1H), 5.21–5.23 (m, 1H), 4.75–4.80 (m, 1H), 3.82–4.52 (m, 5H), 2.19–2.74 (m, 4H), 1.89–1.93 (m, 1H), 0.84–1.59 (m, 53H), 0.53–0.62 (m, 3H)

Compound (103)
$^1$H-NMR (δ ppm, CD$_3$OD) 7.75–7.88 (m, 2H), 7.56–7.69 (m, 2H), 7.26–7.43 (m, 4H), 5.19–5.30 (m, 1H), 3.85–4.96 (m, 7H), 2.46–2.93 (m, 6H), 1.42 (s, 9H), 1.00–2.21 (m, 47H), 0.48–0.98 (m, 24H)

Compound (107)
$^1$H-NMR (δ ppm, d6-DMSO) 7.29–7.97 (m, 11H), 5.08–5.12 (m, 1H), 4.16–4.38 (m, 6H), 2.42–2.66 (m, 4H), 1.09–1.78 (m, 26H), 0.75–0.90 (m, 15H)

Compound (113)
$^1$H-NMR (δ ppm, d6-DMSO) 12.25 (br, 1H), 7.28–8.27 (m, 12H), 5.04–5.09 (m, 1H), 4.56–4.58 (m, 1H), 4.14–4.31 (m, 5H), 3.81–3.84 (m, 1H), 2.38–2.70 (m, 4H), 1.87–2.01 (m, 1H), 1.74–1.78 (m, 1H), 1.09–1.53 (m, 34H), 0.78–0.87 (m, 21H)

Compound (148)
$^1$H-NMR (δ ppm, d6-DMSO) 8.34 (d, J=7.6 Hz, 2H), 7.96–8.12 (m, 2H), 7.88 (d, J=7.6 Hz, 2H), 7.66–7.75 (m, 3H), 7.41 (t, J=7.6 Hz, 2H), 7.28–7.34 (m, 2H), 4.99–5.10 (m, 1H), 4.45–4.63 (m, 3H), 4.18–4.40 (m, 4H), 2.36–2.75 (m, 10H), 1.38 (s, 18H), 1.36 (s, 18H), 1.14–1.57 (m, 20H), 0.81–0.88 (m, 3H)

Example 4

Preparation of Compound (33)

A solution of 100 mg of Compound (32) dissolved in 1 ml of trifluoroacetic acid was stirred at room temperature for 3 hours. After the solvent was removed, to the residue were added ethyl acetate and 5% aqueous sodium hydrogencarbonate and the organic layer was separated. The aqueous layer was washed with ethyl acetate and adjusted to pH 4 with conc. hydrochloric acid. It was then extracted with chloroform and the resulting organic layer was dried over anhydrous sodium sulfate. After the solvent was removed in vacuo, to the resulting residue were added ether and hexane, the precipitate thus separated was recovered by filtration and dried to afford 70 mg of Compound (33).

$^1$H-NMR (δ ppm, CD$_3$OD) 7.25–7.40 (m, 5H), 5.00–5.30 (m, 3H), 4.25–4.55 (m, 4H), 3.85–3.90 (m, 1H), 2.70–2.95 (m, 2H), 2.45–2.70 (m, 2H), 2.25–2.35 (m, 2H), 2.05–2.25 (m, 2H), 1.85–2.00 (m, 2H), 1.55–1.80 (m, 5H), 1.15–1.50 (m, 20H), 0.85–1.10 (m, 21H)

Using the same procedures as described above, the following compounds were prepared:

Compound (39)
$^1$H-NMR (δ ppm, CD$_3$OD) 7.25–7.40 (m, 5H), 5.05–5.30 (m, 3H), 4.65–4.80 (m, 1H), 4.30–4.50 (m, 3H), 3.85–3.95 (m, 1H), 2.40–2.90 (m, 4H), 2.25–2.35 (m, 2H), 1.90–2.20 (m, 4H), 1.40–1.70 (m, 6H), 1.15–1.40 (m, 19H), 1.04 (t, J=7.8 Hz, 3H), 0.80–1.00 (m, 18H)

Compound (41)
$^1$H-NMR (δ ppm, CD$_3$OD) 7.28–7.80 (m, 8H), 5.19–5.24 (m, 1H), 4.18–4.54 (m, 7H), 3.78–3.83 (m, 1H), 2.31–2.91 (m, 7H), 1.15–2.10 (m, 34H), 0.86–0.97 (m, 15H)

Compound (44)

¹H-NMR (δ ppm, CD₃OD) 7.10–7.99 (m, 10H), 5.15–5.29 (m, 1H), 4.18–5.02 (m, 8H), 3.75–3.97 (m, 2H), 2.26–3.01 (m, 6H), 1.24–2.15 (m, 36H), 0.83–0.98 (m, 21H)

Compound (46)

¹H-NMR (δ ppm, d6-DMSO) 6.68–8.28 (m, 13H), 5.06–5.13 (m, 1H), 4.04–4.38 (m, 8H), 2.10–2.49 (m, 8H), 1.21–1.98 (m, 28H), 0.78–0.86 (m, 24H)

Compound (49)

¹H-NMR (δ ppm, d6-DMSO) 6.71–8.55 (m, 14H), 5.07–5.18 (m, 1H), 3.89–4.62 (m, 9H), 1.34–2.51 (m, 17H), 1.22 (br s, 20H), 1.07 (t, J=6.8 Hz, 3H), 0.78–0.86 (m, 27H)

Compound (51)

¹H-NMR (δ ppm, CD₃OD) 7.29–8.41 (m, 10H), 5.10–5.27 (m, 1H), 4.11–4.50 (m, 8H), 2.26–2.58 (m, 6H), 1.13–2.14 (m, 33H), 0.76–1.00 (m, 21H)

Compound (54)

¹H-NMR (δ ppm, CD₃OD) 7.88–7.92 (m, 2H), 7.66–7.70 (m, 2H), 7.37–7.41 (m, 2H), 7.29–7.33 (m, 2H), 5.13–5.30 (m, 1H), 4.30–4.51 (m, 7H), 4.20–4.27 (m, 1H), 3.86–3.94 (m, 1H), 2.43–2.61 (m, 2H), 2.19–2.24 (m, 4H), 1.14–2.18 (m, 34H), 0.81–1.02 (m, 27H)

Compound (56)

¹H-NMR (δ ppm, d6-DMSO) 6.62–7.87 (m, 15H), 5.04–5.09 (m, 1H), 4.04–4.46 (m, 8H), 3.67–3.72 (m, 2H), 2.67–2.92 (m, 2H), 1.22–2.50 (m, 32H), 0.79–0.85 (m, 15H)

Compound (59)

¹H-NMR (δ ppm, d6-DMSO) 6.61–8.54 (m, 18H), 5.05–5.13 (m, 1H), 4.40–4.54 (m, 2H), 4.07–4.29 (m, 7H), 3.64–3.90 (m, 2H), 2.65–2.92 (m, 2H), 2.24–2.59 (m, 4H), 2.05–2.10 (m, 2H), 1.11–1.99 (m, 27H), 0.79–0.88 (m, 21H)

Compound (61)

¹H-NMR (δ ppm, d6-DMSO) 12.35 (br s, 2H), 8.01 (d, J=7.3 Hz, 1H), 7.85 (d, J=7.3 Hz, 2H), 7.68 (d, J=6.8 Hz, 2H), 7.65–8.02 (m, 2H), 7.40 (t, J=7.3 Hz, 2H), 7.31 (t, J=7.1 Hz, 2H), 7.30–7.42 (m, 1H), 7.17 (s, 1H), 6.64 (s, 1H), 5.03–5.14 (m, 1H), 4.49–4.61 (m, 1H), 4.11–4.42 (m, 7H), 3.53–3.77 (m, 2H), 3.12–3.48 (m, 3H), 2.64–2.80 (m, 1H), 2.31–2.57 (m, 3H), 1.41–2.17 (m, 11H), 1.02–1.40 (m, 20H), 0.65–0.93 (m, 15H)

Compound (63)

¹H-NMR (δ ppm, CD₃OD) 7.77–7.79 (m, 2H), 7.65–7.72 (m, 2H), 7.28–7.40 (m, 4H), 5.11–5.20 (m, 1H), 4.65–4.71 (m, 1H), 4.36–4.48 (m, 5H), 4.22–4.31 (m, 2H), 3.81–3.84 (m, 1H), 2.94–3.00 (m, 2H), 2.79–2.87 (m, 2H), 2.44–2.58 (m, 2H), 2.28–2.34 (m, 2H), 2.03–2.12 (m, 2H), 1.15–1.99 (m, 28H), 0.84–1.00 (m, 27H)

Compound (67)

¹H-NMR (δ ppm, CD₃OD) 5.16–5.31 (m, 1H), 4.57–4.64 (m, 1H), 4.19–4.50 (m, 4H), 3.95–4.03 (m, 1H), 2.77–2.98 (m, 2H), 2.46–2.63 (m, 2H), 2.27–2.37 (m, 2H), 2.03, 2.04 (2s, 3H), 1.15–2.15 (m, 32H), 0.83–1.01 (m, 27H)

Compound (69)

¹H-NMR (δ ppm, d6-DMSO) 12.38 (br s, 1H), 6.67–8.78 (m, 13H), 5.09–5.12 (m, 1H), 3.38–4.79 (m, 8H), 1.42–2.71 (m, 18H), 1.13–1.32 (m, 20H), 0.77–0.97 (m, 27H)

Compound (71)

¹H-NMR (δ ppm, d6-DMSO) 12.31 (br s, 1H), 6.65–8.32 (m, 13H), 5.07–5.09 (m, 1H), 4.53–4.56 (m, 1H), 4.18–4.31 (m, 4H), 3.68–3.73 (m, 1H), 1.43–2.72 (m, 18H), 1.23 (br s, 20H), 0.76–0.93 (m, 27H)

Compound (73)

¹H-NMR (δ ppm, CD₃OD) 7.76–7.80 (m, 2H), 7.61–7.63 (m, 2H), 7.35–7.40 (m, 2H), 7.27–7.31 (m, 2H), 7.11–7.24 (m, 5H), 5.18–5.22 (m, 1H), 4.30–4.45 (m, 6H), 4.20–4.24 (m, 1H), 3.85–3.91 (m, 1H), 3.70–3.76 (m, 1H), 3.10–3.22 (m, 1H), 2.90–2.99 (m, 1H), 2.76–2.83 (m, 1H), 2.61–2.69 (m, 1H), 2.46–2.57 (m, 2H), 2.27–2.35 (m, 2H), 1.82–2.17 (m, 4H), 1.61–1.80 (m, 5H), 1.15–1.40 (m, 20H), 0.88–0.96 (m, 21H)

Compound (75)

¹H-NMR (δ ppm, CD₃OD) 7.90–8.20 (m, 3H), 7.79 (d, J=7.6 Hz, 2H), 7.68 (dd, J=7.6, 12.4 Hz, 2H), 7.39 (t, J=7.4 Hz, 2H), 7.30 (t, J=7.4 Hz, 2H), 7.20–7.25 (m, 1H), 5.10–5.30 (m, 1H), 4.24–4.42 (m, 8H), 3.87–3.95 (m, 1H), 2.30–2.52 (m, 6H), 1.14–2.10 (m, 34H), 0.86–0.99 (m, 27H)

Compound (77)

¹H-NMR (δ ppm, CD₃OD) 7.64–7.79 (m, 4H), 7.30–7.39 (m, 4H), 5.12–5.18 (m, 1H), 4.20–4.42 (m, 8H), 3.77–3.81 (m, 1H), 2.83–2.87 (m, 1H), 2.65–2.70 (m, 1H), 2.41–2.55 (m, 2H), 2.29–2.32 (m, 2H), 1.45–2.10 (m, 12H), 1.21–1.40 (m, 20H), 0.85–1.02 (m, 27H)

Compound (79)

¹H-NMR (δ ppm, d6-DMSO) 7.23–8.27 (m, 15H), 6.63 (br s, 1H), 5.07–5.11 (m, 1H), 3.94–4.36 (m, 9H), 3.54–3.63 (m, 2H), 2.33–2.50 (m, 2H), 1.22–2.08 (m, 34H), 1.10 (t, J=6.8 Hz, 3H), 0.78–0.86 (m, 24H)

Compound (81)

¹H-NMR (δ ppm, d6-DMSO) 7.24–8.49 (m, 16H), 6.84 (brs, 1H), 6.64 (brs, 1H), 5.07–5.14 (m, 1H), 3.68–4.58 (m, 1H), 1.92–2.59 (m, 8H), 1.02–1.70 (m, 30H), 0.79–0.86 (m, 27H)

Compound (83)

¹H-NMR (δ ppm, CD₃OD) 7.16–7.84 (m, 21H), 5.14–5.25 (m, 1H), 4.10–4.90 (m, 9H), 1.18–3.34 (m, 39H), 0.81–0.95 (m, 21H)

Compound (85)

¹H-NMR (δ ppm, d6-DMSO) 6.67–8.59 (m, 15H), 5.01–5.24 (m, 1H), 3.99–4.55 (m, 9H), 1.04–2.84 (m, 41H), 0.68–0.90 (m, 27H)

Compound (90)

FAB-MS 1200 (MK⁺)

Compound (94)

FAB-MS 1200 (MK⁺)

Compound (97)

¹H-NMR (δ ppm, d6-DMSO) 7.99–8.26 (m, 1H), 7.85–7.87 (m, 3H), 7.71–7.74 (m, 2H), 7.29–7.42 (m, 6H), 5.19–5.31 (m, 1H), 4.04–4.74 (m, 6H), 3.89–3.93 (m, 1H), 1.14–2.54 (m, 31H), 0.77–0.94 (m, 21H)

Compound (99)

¹H-NMR (δ ppm, CD₃OD) 7.77–7.81 (m, 2H), 7.65–7.69 (m, 2H), 7.37–7.41 (m, 2H), 7.29–7.33 (m, 2H), 5.15–5.27 (m, 1H), 4.64–4.73 (m, 1H), 4.20–4.50 (m, 7H), 3.85–3.93 (m, 1H), 2.71–2.95 (m, 2H), 2.29–2.62 (m, 4H), 1.86–2.16 (m, 4H), 1.17–1.80 (m, 28H), 0.80–1.00 (m, 27H)

Compound (104)

¹H-NMR (δ ppm, CD₃OD) 7.75–7.84 (m, 4H), 7.25–7.43 (m, 4H), 5.21–5.39 (m, 1H), 4.18–4.90 (m, 6H), 3.60–4.05 (m, 1H), 2.39–2.92 (m, 6H), 0.99–2.22 (m, 47H), 0.48–0.97 (m, 24H)

Compound (106)

FAB-MS 1354 (MK⁺)

Compound (111)

¹H-NMR (δ ppm, d6-DMSO) 12.33 (br s, 1H), 6.64–8.28 (m, 13H), 4.95–5.15 (m, 3H), 3.69–4.55 (m, 6H), 1.00–2.70 (m, 38H), 0.77–0.89 (m, 27H)

Compound (114)

¹H-NMR (δ ppm, d6-DMSO) 12.25 (br s, 2H), 7.29–8.28 (m, 12H), 5.07–5.10 (m, 1H), 4.52–4.55 (m, 1H), 4.14–4.30 (m, 5H), 3.83–3.89 (m, 1H), 2.45–2.69 (m, 4H), 1.04–2.00 (m, 27H), 0.81–0.87 (m, 21H)

Compound (116)

¹H-NMR (δ ppm, d6-DMSO) 8.18–8.35 (m, 2H), 7.38–7.93 (m, 9H), 7.28–7.32 (m, 2H), 5.05–5.12 (m, 1H), 4.08–4.54 (m, 7H), 3.79–3.84 (m, 1H), 2.32–2.76 (m, 6H), 1.01–1.99 (m, 33H), 0.75–0.85 (m, 21H)

Compound (118)
$^1$H-NMR (δ ppm, d6-DMSO) 12.20 (br s, 3H), 7.99–8.27 (m, 3H), 7.68–7.87 (m, 6H), 7.29–7.42 (m, 5H), 5.07–5.12 (m, 1H), 4.52–4.57 (m, 1H), 4.11–4.36 (m, 7H), 3.82–3.89 (m, 1H), 2.21–2.69 (m, 8H), 1.03–2.00 (m, 30H), 0.77–0.89 (m, 27H)

Compound (120)
$^1$H-NMR (δ ppm, d6-DMSO) 12.31 (br s, 2H), 7.29–8.27 (m, 14H), 5.07–5.12 (m, 1H), 4.52–4.56 (m, 1H), 4.10–4.37 (m, 7H), 3.83–3.88 (m, 1H), 2.33–2.73 (m, 4H), 1.04–2.00 (m, 30H), 0.76–0.90 (m, 30H)

Compound (122)
$^1$H-NMR (δ ppm, d6-DMSO) 12.27 (br s, 2H), 8.13–8.28 (m, 2H), 7.70–7.92 (m, 7H), 7.29–7.42 (m, 6H), 5.07–5.09 (m, 1H), 4.55–4.62 (m, 2H), 4.12–4.31 (m, 6H), 3.83–3.88 (m, 1H), 2.32–2.70 (m, 6H), 1.04–1.99 (m, 30H), 0.79–0.88 (m, 27H)

Compound (126)
$^1$H-NMR (δ ppm, d6-DMSO) 7.28–8.36 (m, 9H), 4.99–5.09 (m, 3H), 4.40–4.57 (m, 2H), 3.87–4.08 (m, 2H), 2.34–2.57 (m, 4H), 1.99–2.04 (m, 1H), 1.76–1.82 (m, 1H), 1.22–1.52 (m, 25H), 0.81–0.88 (m, 21H)

Compound (131)
$^1$H-NMR (δ ppm, d6-DMSO) 8.63 (br s, 1H), 7.92–7.98 (m, 4H), 7.37–7.51 (m, 5H), 5.01–5.13 (m, 1H), 4.08–4.57 (m, 4H), 2.18–2.64 (m, 4H), 1.05–1.79 (m, 27H), 0.78–0.93 (m, 21H)

Compound (132)
$^1$H-NMR (δ ppm, d6-DMSO) 7.17–8.40 (m, 9H), 4.12–5.26 (m, 5H), 3.42–3.74 (m, 2H), 2.15–2.77 (m, 4H), 1.18–1.83 (m, 27H), 0.78–0.86 (m, 21H)

Compound (134)
$^1$H-NMR (δ ppm, d6-DMSO) 8.08–8.36 (m, 4H), 7.69–7.90 (m, 5H), 7.30–7.48 (m, 5H), 5.01–5.08 (m, 1H), 4.45–4.61 (m, 2H), 4.12–4.37 (m, 6H), 3.81–3.91 (m, 1H), 2.52–2.81 (m, 4H), 2.33–2.46 (m, 2H), 2.20–2.29 (m, 2H), 1.07–2.05 (m, 29H), 0.77–0.92 (m, 21H)

Compound (140)
$^1$H-NMR (δ ppm, d6-DMSO) 8.34–8.45 (m, 1H), 8.03–8.18 (m, 4H), 7.85–7.89 (m, 2H), 7.67–7.79 (m, 2H), 7.28–7.46 (m, 5H), 5.00–5.09 (m, 1H), 4.46–4.62 (m, 3H), 4.15–4.35 (m, 5H), 3.82–3.91 (m, 1H), 2.19–2.80 (m, 10H), 1.09–2.06 (m, 26H), 0.78–0.91 (m, 15H)

Compound (142)
$^1$H-NMR (δ ppm, d6-DMSO) 8.32–8.40 (m, 1H), 8.00–8.17 (m, 4H), 7.85–7.89 (m, 2H), 7.65–7.75 (m, 3H), 7.39–7.43 (m, 2H), 7.31–7.35 (m, 2H), 4.99–5.08 (m, 1H), 4.45–4.63 (m, 3H), 4.15–4.41 (m, 6H), 2.18–2.81 (m, 12H), 1.09–1.94 (m, 25H), 0.79–0.90 (m, 9H)

Compound (149)
$^1$H-NMR (δ ppm, d6-DMSO) 8.32–8.38 (m, 1H), 8.00–8.09 (m, 2H), 7.87 (d, J=7.6 Hz, 2H), 7.63–7.75 (m, 3H), 7.41 (t, J=7.6 Hz, 2H), 7.33 (t, J=7.6 Hz, 2H), 4.98–5.09 (m, 1H), 4.44–4.61 (m, 3H), 4.15–4.40 (m, 4H), 2.41–2.78 (m, 10H), 1.12–1.56 (m, 20H), 0.81–0.88 (m, 3H)

Compound (151)
$^1$H-NMR (δ ppm, d6-DMSO) 7.98–8.37 (m, 5H), 7.87 (d, J=7.6 Hz, 2H), 7.64–7.75 (m, 3H), 7.41 (t, J=7.6 Hz, 2H), 7.33 (t, J=7.6 Hz, 2H), 5.00–5.10 (m, 1H), 4.16–4.63 (m, 9H), 2.18–2.82 (m, 14H), 1.84–1.96 (m, 1H), 1.65–1.79 (m, 1H), 1.09–1.56 (m, 20H), 0.83–0.86 (m, 3H)

Compound (154)
$^1$H-NMR (δ ppm, d6-DMSO) 8.10–8.50 (m, 3H), 6.60–7.70 (m, 4H), 7.83–7.90 (m, 2H), 7.70–7.77 (m, 2H), 7.26–7.43 (m, 4H), 5.00–5.17 (m, 1H), 3.86–4.60 (m, 10H), 2.31–2.56 (m, 4H), 0.94–2.16 (m, 39H), 0.75–0.93 (m, 33H)

Compound (156)
$^1$H-NMR (δ ppm, d6-DMSO) 12.5 (br s, 2H), 8.52 (s, 1H), 7.98–8.14 (m, 3H), 7.86 (d, J=7.3 Hz, 2H), 7.73 (t, J=8.8 Hz, 2H), 7.60 (br s, 1H), 7.40 (t, J=7.6 Hz, 2H), 7.31 (dt, J=3.9, 7.1 Hz, 2H), 7.26–7.36 (m, 1H), 7.24 (br s, 1H), 6.84 (br s, 1H), 5.10–5.17 (m, 1H), 4.53–4.59 (m, 1H), 4.05–4.39 (m, 7H), 3.89 (t, J=7.1 Hz, 1H), 3.24 (br s, 2H), 2.35–2.51 (m, 4H), 2.09 (t, J=7.8 Hz, 2H), 1.97–2.14 (m, 1H), 1.86–1.96 (m, 1H), 1.76–1.85 (m, 1H), 1.09–1.76 (m, 27H), 0.67–0.93 (m, 27H)

Compound (158)
$^1$H-NMR (δ ppm, d6-DMSO) 8.48 (s, 1H), 8.39 (br s, 1H), 8.30 (br s, 1H), 7.86 (d, J=7.3 Hz, 2H), 7.73 (t, J=8.8 Hz, 2H), 7.68 (br s, 1H), 7.53 (br s, 1H), 7.40 (t, J=7.6 Hz, 2H), 7.28–7.35 (m, 2H), 7.25–7.48 (m, 2H), 6.79 (br s, 1H), 5.08 (br s, 1H), 4.60 (br s, 1H), 4.43 (br s, 1H), 3.90–4.30 (m, 7H), 3.22 (br s, 2H), 2.30–2.55 (m, 4H), 1.70–2.15 (m, 5H), 1.10–1.70 (m, 27H), 0.70–0.95 (m, 27H)

Compound (161)
$^1$H-NMR (δ ppm, d6-DMSO) 8.00–8.40 (m, 3H), 7.85–7.88 (m, 2H), 7.54–7.76 (m, 2H), 7.11–7.43 (m, 5H), 6.66–6.88 (m, 1H), 5.02–5.17 (m, 1H), 3.85–4.98 (m, 9H), 3.23–3.76 (m, 2H), 1.06–2.85 (m, 39H), 0.64–0.93 (m, 21H)

Compound (164)
$^1$H-NMR (δ ppm, d6-DMSO) 12.36 (s, 2H), 8.29 (d, J=7.8 Hz, 1H), 8.00 (d, J=8.3 Hz, 1H), 7.87 (d, J=7.8 Hz, 2H), 7.81 (d, J=8.8 Hz, 1H), 7.75 (d, J=7.3 Hz, 1H), 7.71 (d, J=7.3 Hz, 1H), 7.41 (t, J=7.3 Hz, 2H), 7.38–7.43 (m, 1H), 7.32 (t, J=7.6 Hz, 2H), 5.15–5.25 (m, 1H), 4.50–4.60 (m, 1H), 4.17–4.43 (m, 5H), 3.86 (t, J=7.11 Hz, 1H), 3.46 (dd, J=5.9, 15 Hz, 1H), 3.41 (dd, J=3.9, 11 Hz, 1H), 3.24–3.41 (m, 4H), 2.69 (dd, J=5.4, 17 Hz, 1H), 2.42–2.63 (m, 1H), 1.91–2.05 (m, 1H), 1.78 (br s, 1H), 1.32–1.65 (m, 5H), 1.11–1.31 (m, 18H), 0.70–0.95 (m, 21H)

Compound (167)
$^1$H-NMR (δ ppm, d6-DMSO) 12.34 (s, 2H), 8.29 (d, J=7.3 Hz, 1H), 7.91 (d, J=7.8 Hz, 1H), 7.87 (d, J=7.3 Hz, 2H), 7.83 (d, J=8.3 Hz, 1H), 7.75 (d, J=7.3 Hz, 1H), 7.72 (d, J=7.8 Hz, 1H), 7.41 (t, J=7.6 Hz, 2H), 7.38–7.43 (m, 1H), 7.31 (dt, J=2.9, 7.3 Hz, 2H), 5.03–5.14 (m, 1H), 4.54 (q, J=7.0 Hz, 1H), 4.13–4.41 (m, 5H), 3.86 (t, J=7.1 Hz, 1H), 3.32 (s, 2H), 2.68 (dd, J=5.1, 17 Hz, 1H), 2.42–2.64 (m, 1H), 1.92–2.05 (m, 1H), 1.79 (br s, 1H), 1.10–1.66 (m, 35H), 0.76–0.93 (m, 21H)

Example 5

Preparation of Compound (42)

To a solution of 1.41 g of Compound (40) dissolved in 10 ml of DMF was added 1.0 ml of diethylamine and the mixture was stirred at room temperature for 3 hours. After the solvent was removed in vacuo, the residue was subjected to column chromatography using silica gel and eluted with chloroform:methanol=97:3 to afford 1.17 g of Compound (42).

$^1$H-NMR (δ ppm, DCDl$_3$) 6.83–7.23 (m, 9H), 6.16–6.25 (m, 1H), 5.17–5.36 (m, 1H), 4.27–4.60 (m, 4H), 3.84–4.00 (m, 1H), 3.78–3.80 (m, 6H), 3.55–3.59 (m, 2H), 1.14–1.84 (m, 58H), 0.84–0.92 (m, 15H)

Using the same procedures as described above, the following compounds were prepared:

Compound (47)
$^1$H-NMR (δ ppm, DCDl$_3$) 6.71–7.89 (m, 13H), 6.19–6.24 (m, 1H), 5.18–5.20 (m, 1H), 4.31–4.55 (m, 4H), 3.79 (s, 3H), 3.78 (s, 3H), 3.59–3.62 (m, 1H), 2.32–2.83 (m, 8H), 1.13–2.14 (m, 48H), 0.84–0.93 (m, 24H)

Compound (52)
$^1$H-NMR (δ ppm, DCDl$_3$) 7.33–8.07 (m, 5H), 6.97–7.24 (m, 9H), 6.60–6.89 (m, 9H), 6.02–6.23 (m, 2H), 4.81–5.25

(m, 1H), 4.20–4.53 (m, 4H), 3.74–3.78 (m, 12H), 3.41–3.61 (m, 1H), 1.08–2.45 (m, 48H), 0.77–0.93 (m, 21H)

Compound (57)

$^1$H-NMR (δ ppm, DCDl3) 6.68–7.87 (m, 13H), 6.20 (d, J=8.3 Hz, 1H), 5.16–5.24 (m, 1H), 4.29–4.66 (m, 6H), 3.78 (s, 3H), 3.77 (s, 3H), 3.44–3.54 (m, 1H), 2.03–2.70 (m, 8H), 1.24–1.79 (m, 55H), 0.81–0.91 (m, 15H)

Compound (64)

$^1$H-NMR (δ ppm, CD$_3$OD) 5.21–5.28 (m, 1H), 4.70–4.79 (m, 1H), 4.21–4.50 (m, 4H), 3.60–3.70 (m, 1H), 2.50–2.73 (m, 4H), 2.27–2.33 (m, 2H), 1.26–2.21 (m, 32H), 0.87–0.96 (m, 27H)

Compound (65)

$^1$H-NMR (δ ppm, DCDl$_3$) 6.76–7.76 (m, 14H), 6.21–6.29 (m, 1H), 5.14–5.20 (m, 1H), 4.85–4.88 (m, 1H), 4.23–4.57 (m, 4H), 3.76–3.79 (m, 6H), 3.23–3.33 (m, 1H), 1.96–2.73 (m, 8H), 1.10–1.85 (m, 50H), 0.81–0.97 (m, 27H)

Compound (86)

$^1$H-NMR (δ ppm, d6-DMSO) 6.60–8.73 (m, 7H), 5.03–5.24 (m, 1H), 3.96–4.71 (m, 6H), 1.11–2.68 (m, 41H), 0.68–0.91 (m, 27H)

Compound (101)

$^1$H-NMR (δ ppm, DCDl$_3$) 6.87 (d, J=8.3 Hz, 1H), 5.23–5.28 (m, 1H), 5.11 (s, 2H), 4.45–4.53 (m, 2H), 3.63–3.65 (m, 1H), 2.55–2.85 (m, 4H), 1.05–1.91 (m, 37H), 0.84–0.99 (m, 15H)

Compound (109)

$^1$H-NMR (δ ppm, DCDl$_3$) 6.68–7.86 (m, 12H), 6.16–6.24 (m, 1H), 5.17–5.21 (m, 1H), 4.32–4.58 (m, 4H), 3.79 (s, 3H), 3.73 (s, 3H), 3.63–3.66 (m, 1H), 2.78–2.83 (m, 1H), 2.32–2.64 (m, 5H), 2.01–2.14 (m, 2H), 1.11–2.00 (m, 50H), 0.84–0.93 (m, 21H)

Compound (124)

$^1$H-NMR (δ ppm, DCDl$_3$) 6.86–7.76 (m, 3H), 5.17–5.23 (m, 1H), 4.46–4.53 (m, 2H), 3.63–3.66 (m, 1H), 2.41–2.86 (m, 4H), 1.25–2.00 (m, 46H), 0.86–0.95 (m, 15H)

Compound (128)

$^1$H-NMR (δ ppm, DCDl$_3$) 8.33–8.37 (m, 1H), 7.01–7.05 (m, 1H), 6.67–6.73 (m, 1H), 5.15–5.23 (m, 1H), 4.76–4.80 (m, 1H), 4.44–4.52 (m, 2H), 3.37 (d, J=3.9 Hz, 1H), 2.40–2.84 (m, 4H), 2.21–2.28 (m, 1H), 1.10–1.98 (m, 46H), 0.83–1.01 (m, 21H)

Compound (136)

$^1$H-NMR (δ ppm, DCDl$_3$) 8.22–8.30 (m, 1H), 6.97–7.08 (m, 1H), 6.75–6.83 (m, 1H), 5.08–5.21 (m, 1H), 4.74–4.82 (m, 1H), 4.32–4.50 (m, 2H), 3.67–3.76 (m, 1H), 2.31–3.08 (m, 8H), 2.05–2.17 (m, 1H), 1.87–1.98 (m, 1H), 1.19–1.78 (m, 59H), 0.86–0.96 (m, 9H)

Compound (138)

$^1$H-NMR (δ ppm, DCDl$_3$) 8.38–8.45 (m, 1H), 7.46–7.78 (m, 1H), 7.00–7.16 (m, 1H), 6.83–6.87 (m, 1H), 5.07–5.18 (m, 1H), 4.71–4.86 (m, 2H), 4.35–4.52 (m, 2H), 3.64–3.71 (m, 1H), 2.61–2.95 (m, 6H), 2.34–2.57 (m, 4H), 2.06–2.18 (m, 1H), 1.88–1.99 (m, 1H), 1.19–1.73 (m, 68H), 0.86–0.95 (m, 9H)

Compound (146)

$^1$H-NMR (δ ppm, DCDl$_3$) 8.41–8.46 (m, 1H), 7.28–7.46 (m, 6H), 5.20–5.28 (m, 1H), 5.11, 5.12 (2s, 2H), 4.69–4.84 (m, 2H), 3.64–3.69 (m, 1H), 2.52–2.97 (m, 8H), 1.18–1.72 (m, 49H), 0.88 (t, J=6.8 Hz, 3H)

Compound (159)

$^1$H-NMR (δ ppm, DCDl$_3$) 7.05–7.66 (m, 7H), 6.54–6.90 (m, 5H), 6.16–6.26 (m, 1H), 5.07–5.26 (m, 1H), 4.26–4.61 (m, 4H), 3.83–3.95 (m, 1H), 3.48–3.81 (m, 8H), 1.08–2.71 (m, 56H), 0.78–0.95 (m, 15H)

Example 6

Preparation of Compound (66)

To a solution of 1.07 g of Compound (65) obtained in the same manner as described in Example 5 in 4 ml of methylene chloride were added 0.08 g of pyridine and 0.12 g of acetic anhydride and the mixture was stirred at room temperature for 16 hours. After the solvent was removed in vacuo, the residue was crystallized from chloroformisopropyl ether to afford 0.91 g of Compound (66).

$^1$H-NMR (δ ppm, DCDl$_3$) 7.74–7.86 (m, 1H), 7.57–7.70 (m, 1H), 7.26–7.44 (m, 3H), 7.12–7.24 (m, 5H), 6.91–7.00 (m, 1H), 6.82–6.85 (m, 4H), 6.14–6.18 (m, 1H), 5.12–5.22 (m, 1H), 4.59–4.75 (m, 1H), 4.24–4.49 (m, 4H), 4.02–4.10 (m, 1H), 3.783 (s, 3H), 3.779 (s, 3H), 2.69–2.93 (m, 2H), 1.97, 1.98 (2s, 3H), 1.21–2.52 (m, 54H), 0.80–0.96 (m, 27H)

Example 7

Preparation of Compound (68)

To a solution of 0.71 g of Compound (65) obtained in the same manner as described in Example 5 in 5 ml of methanol were added 0.07 g of saturated aqueous sodium cyanoborohydride and 0.11 g of benzaldehyde and the mixture was stirred at room temperature for 3.5 hours. The reaction solution was diluted with chloroform, washed with sodium hydrogencarbonate and dried over anhydrous sodium sulfate. After the solvent was removed in vacuo, the residue was subjected to column chromatography using silica gel (50 g) and eluted with chloroform:methanol=50:0–1 to afford 0.39 g of Compound (68).

$^1$H-NMR (δ ppm, DCDl$_3$) 6.46–8.28 (m, 19H), 6.24–6.28 (m, 1H), 4.26–5.20 (m, 7H), 3.52–3.87 (m, 8H), 2.05–2.84 (m, 8H), 1.07–1.83 (m, 48H), 0.69–0.96 (m, 27H)

Using the same procedures as described above, the following compound was prepared:

Compound (130)

$^1$H-NMR (δ ppm, DCDl$_3$) 8.18–8.29 (m, 1H), 7.23–7.43 (m, 5H), 7.01–7.04 (m, 1H), 6.73–6.82 (m, 1H), 5.13–5.19 (m, 1H), 4.75–4.80 (m, 1H), 4.44–4.53 (m, 2H), 3.87 (d, J=13 Hz, 1H), 3.60 (d, J=13 Hz, 1H), 3.01–3.06 (m, 1H), 2.85–2.92 (m, 1H), 2.63–2.71 (m, 1H), 2.37–2.53 (m, 2H), 1.08–2.14 (m, 45H), 0.81–0.98 (m, 21H)

Example 8

Preparation of Compound (70)

To a solution of 0.55 g of Compound (65) obtained in the same manner as described in Example 5 in 5 ml of pyridine was added 0.08 ml of benzoyl chloride while stirring in an ice-bath and the mixture was stirred under ice-cooling for one hour. The reaction solution was diluted with ethyl acetate, washed with water and dried over anhydrous sodium sulfate. Then, the solvent was removed in vacuo to afford 0.94 g of Compound (70).

$^1$H-NMR (δ ppm, DCDl$_3$) 6.80–8.17 (m, 20H), 6.21 (d, J=8.3 Hz, 1H), 4.77–5.13 (m, 2H), 4.27–4.48 (m, 5H), 3.76–3.77 (m, 6H), 2.71–2.87 (m, 2H), 2.01–2.44 (m, 7H), 1.12–1.81 (m, 47H), 0.81–1.01 (m, 27H)

Using the same procedures as described above, the following compound was prepared:

Compound (129)

$^1$H-NMR (δ ppm, DCDl$_3$) 6.85–8.64 (m, 9H), 5.13–5.17 (m, 1H), 4.45–4.75 (m, 4H), 2.19–2.94 (m, 4H), 1.01–1.92 (m, 45H), 0.78–0.98 (m, 21H)

Scheme 1
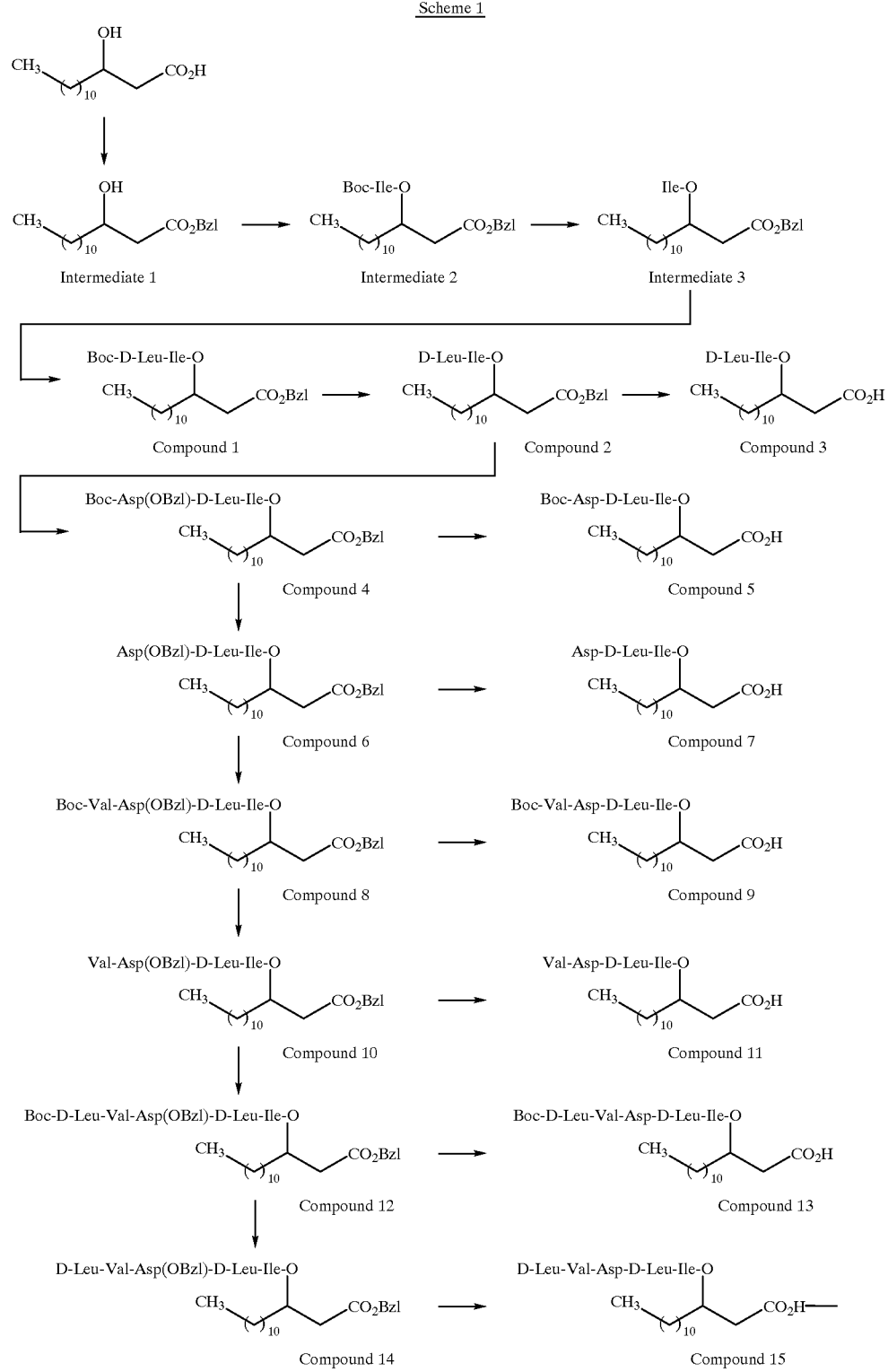

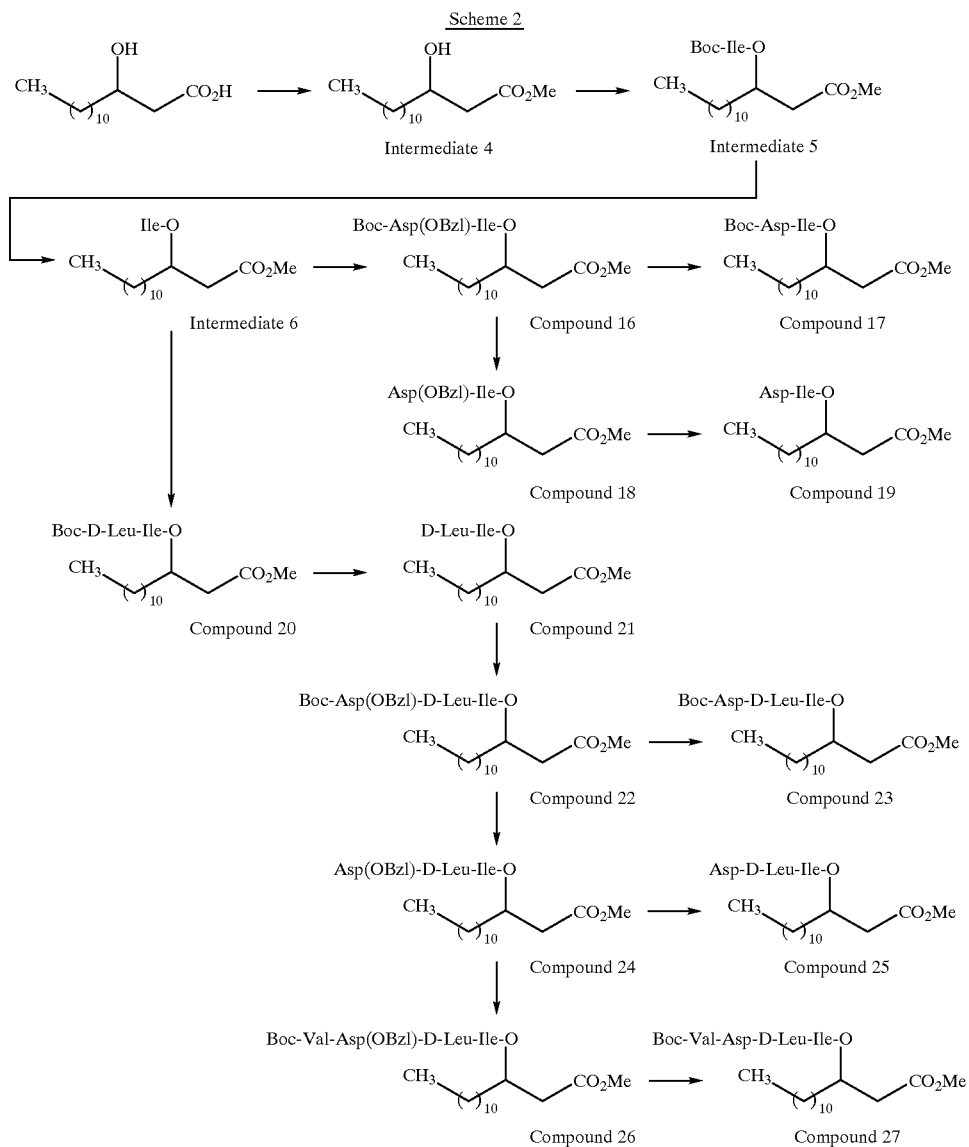
Scheme 2
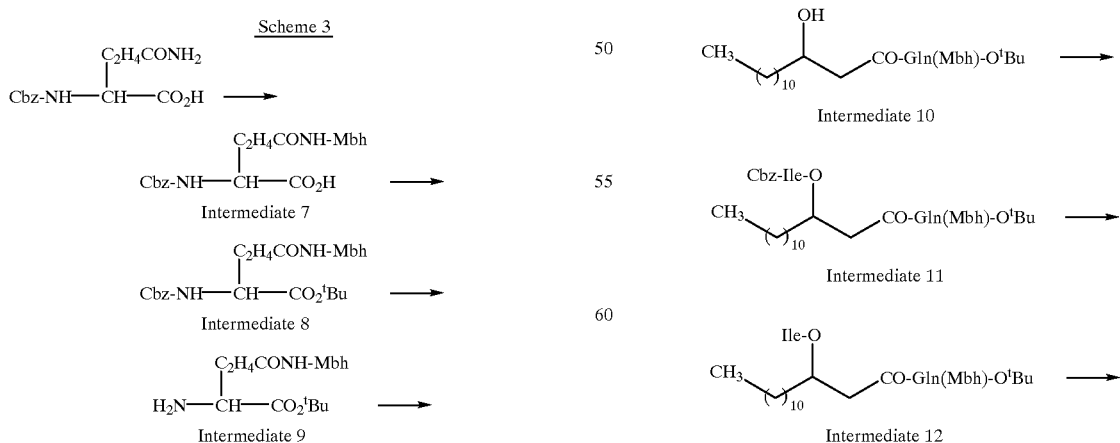
Scheme 3

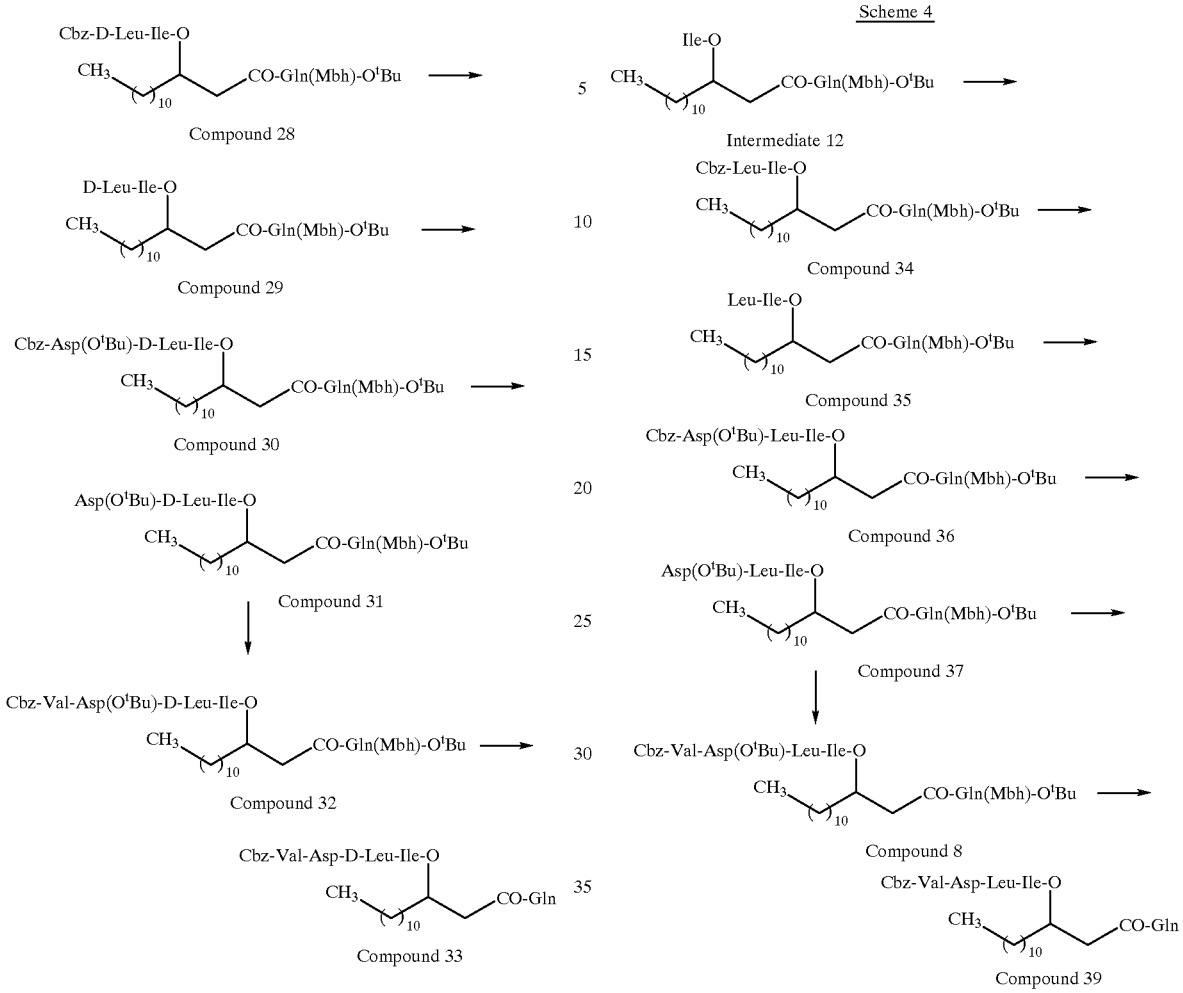
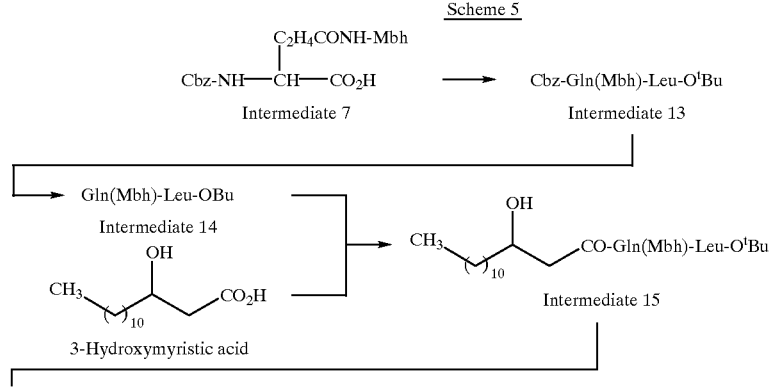

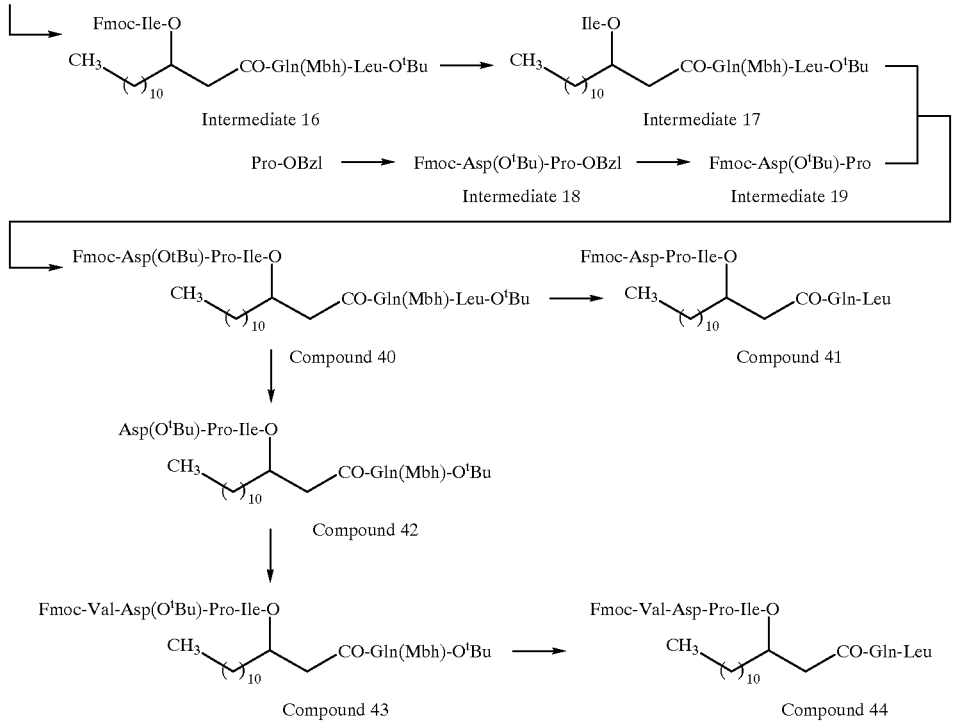
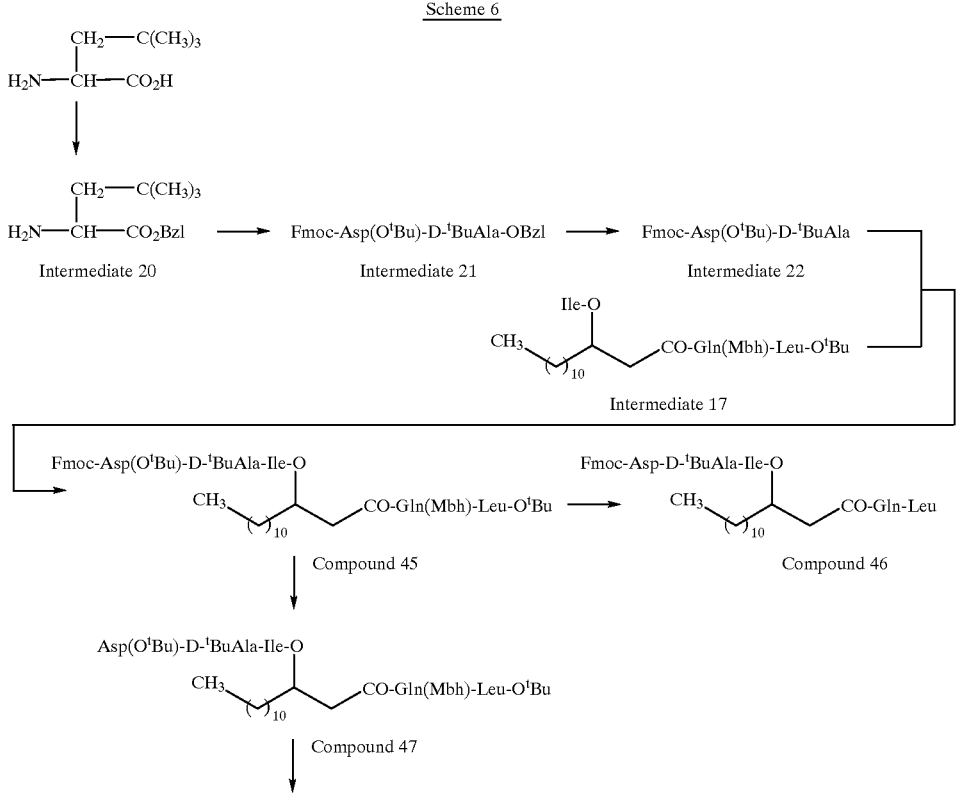
Scheme 6

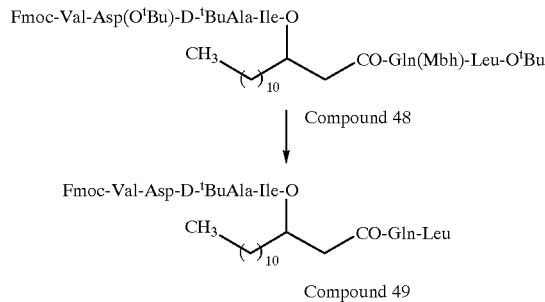
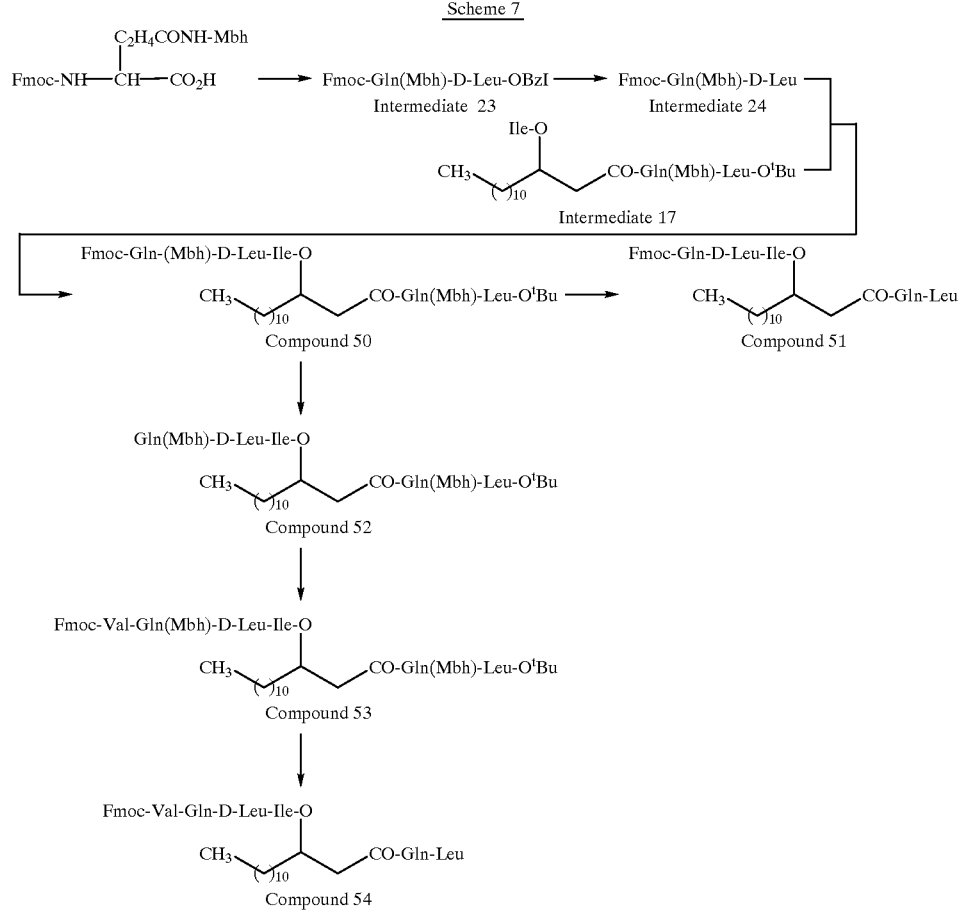
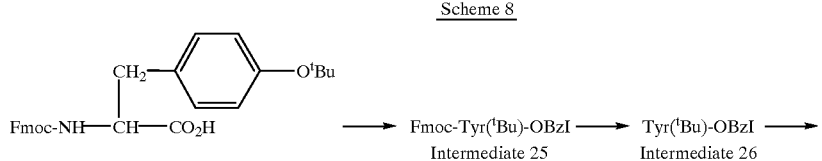

-continued
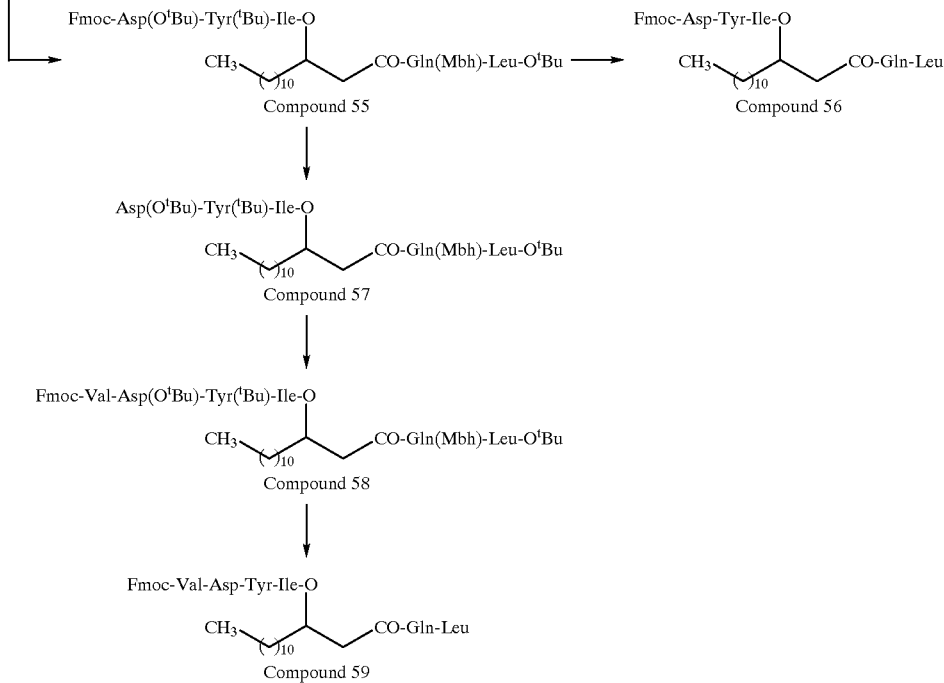
Scheme 9
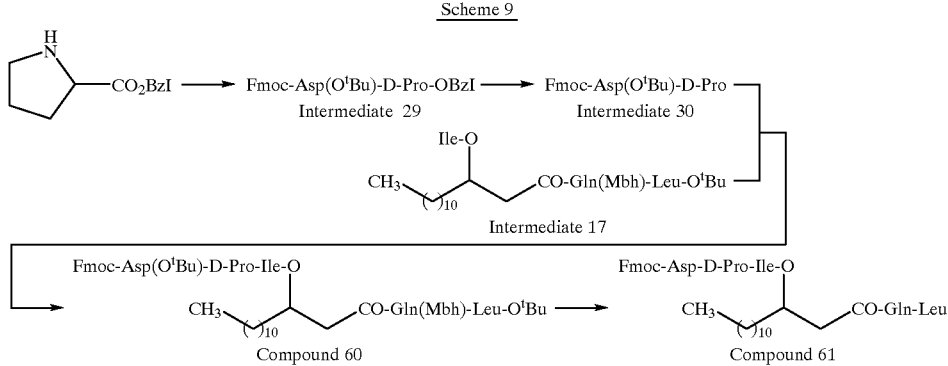

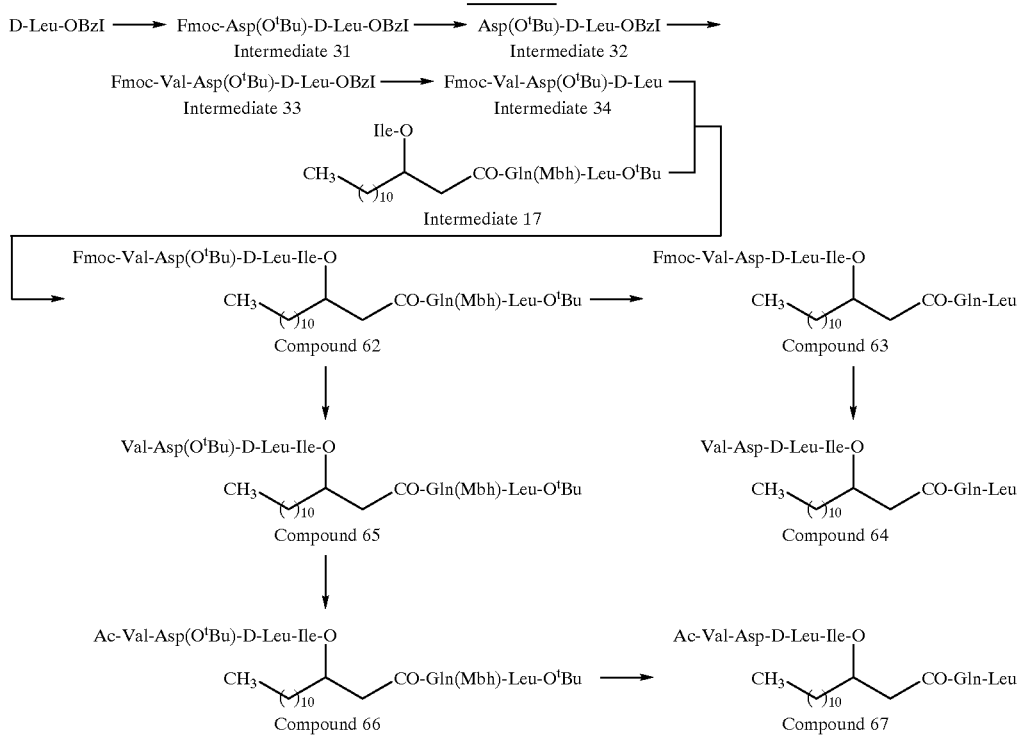
Scheme 10
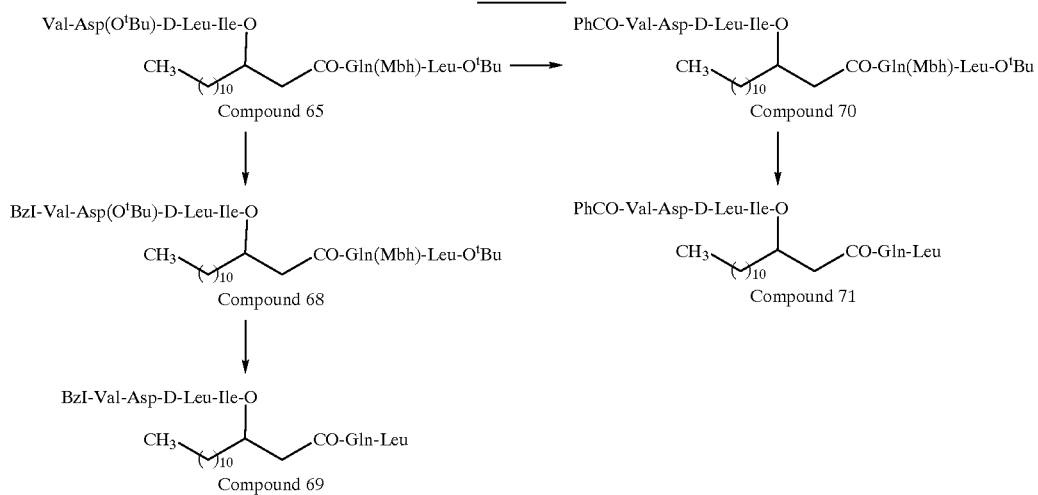
Scheme 11

Scheme 12
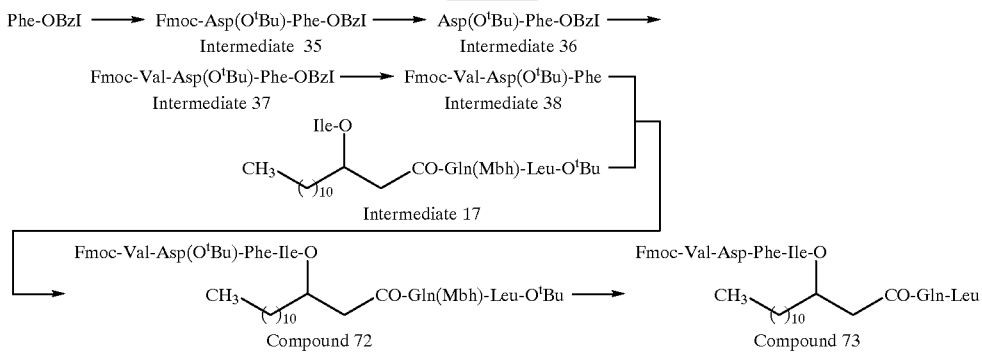
Scheme 13
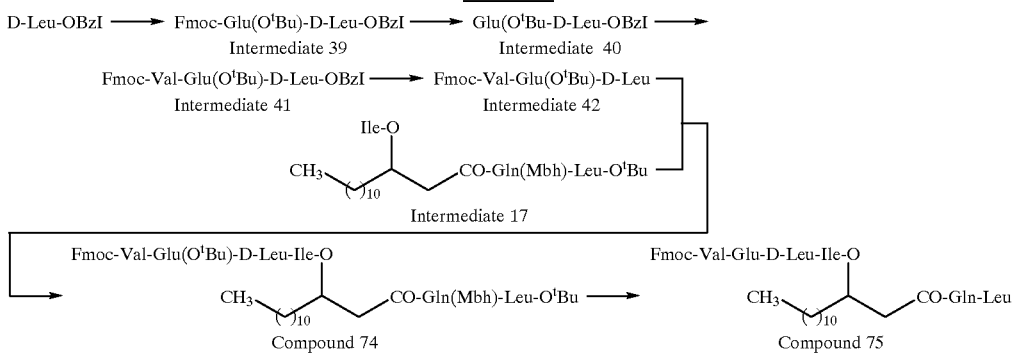
Scheme 14
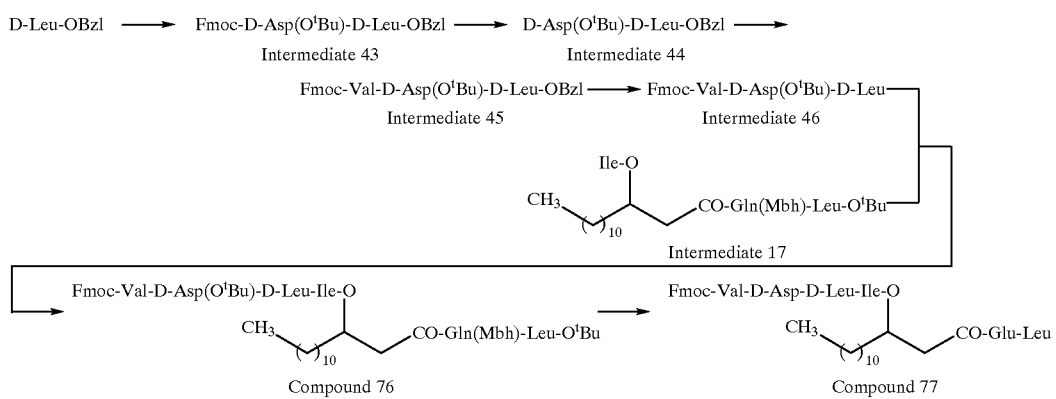

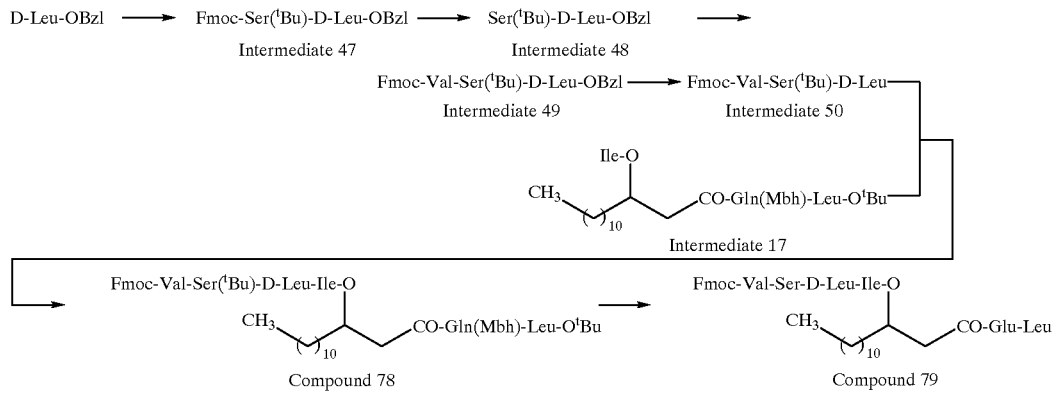
Scheme 15
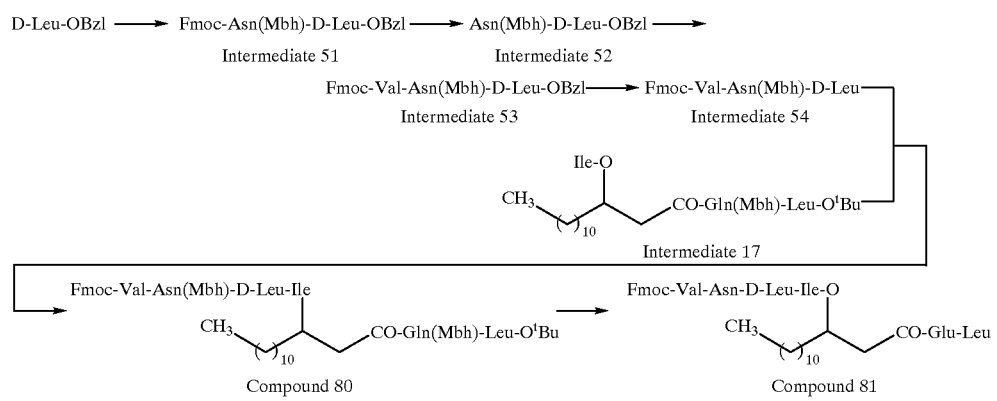
Scheme 16
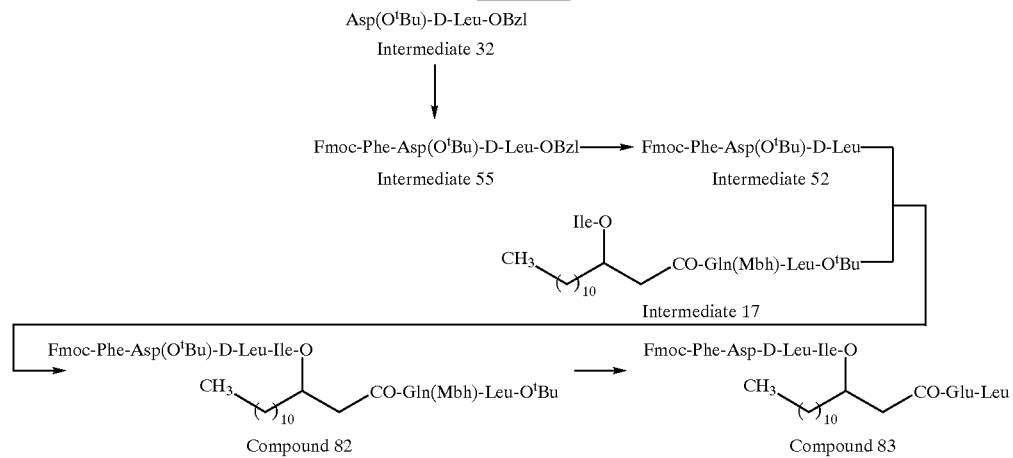
Scheme 17

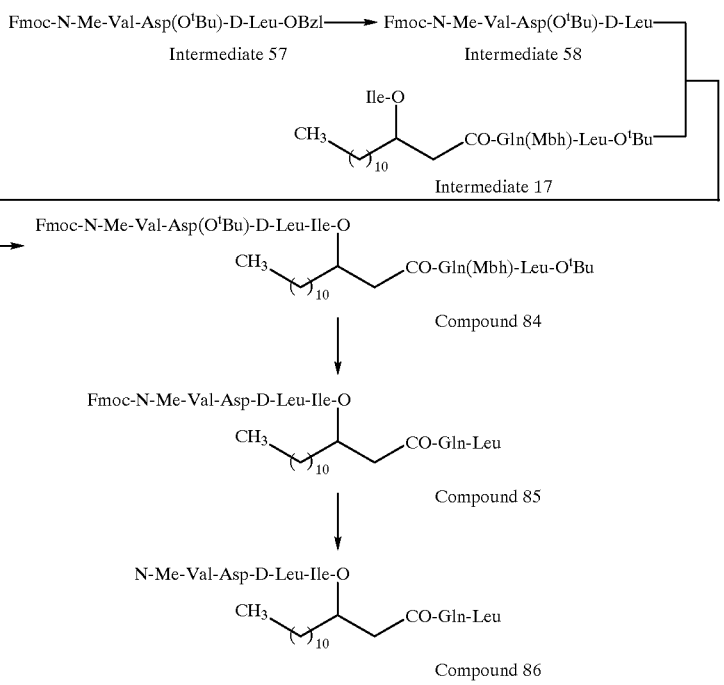
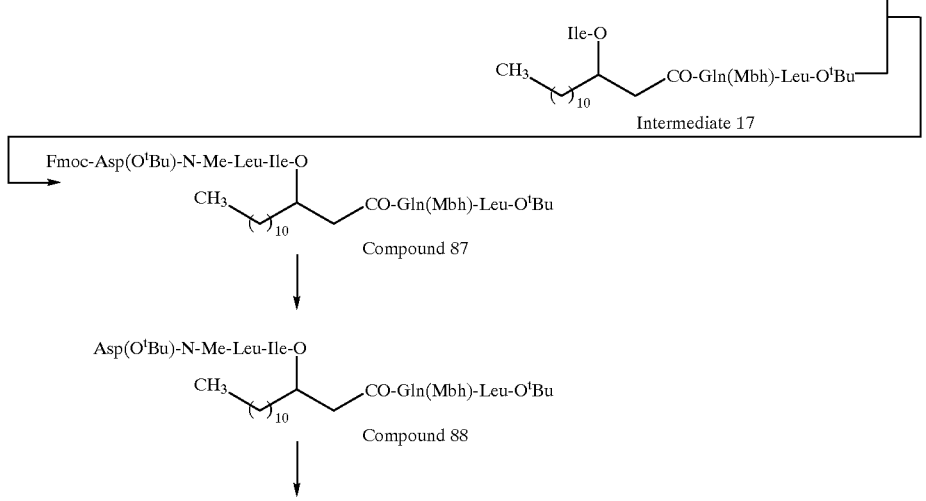

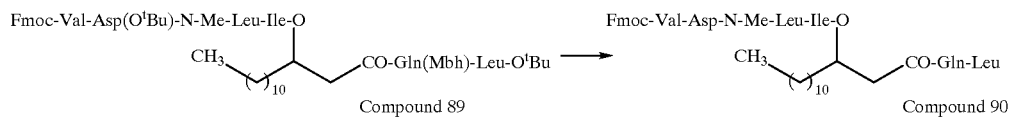
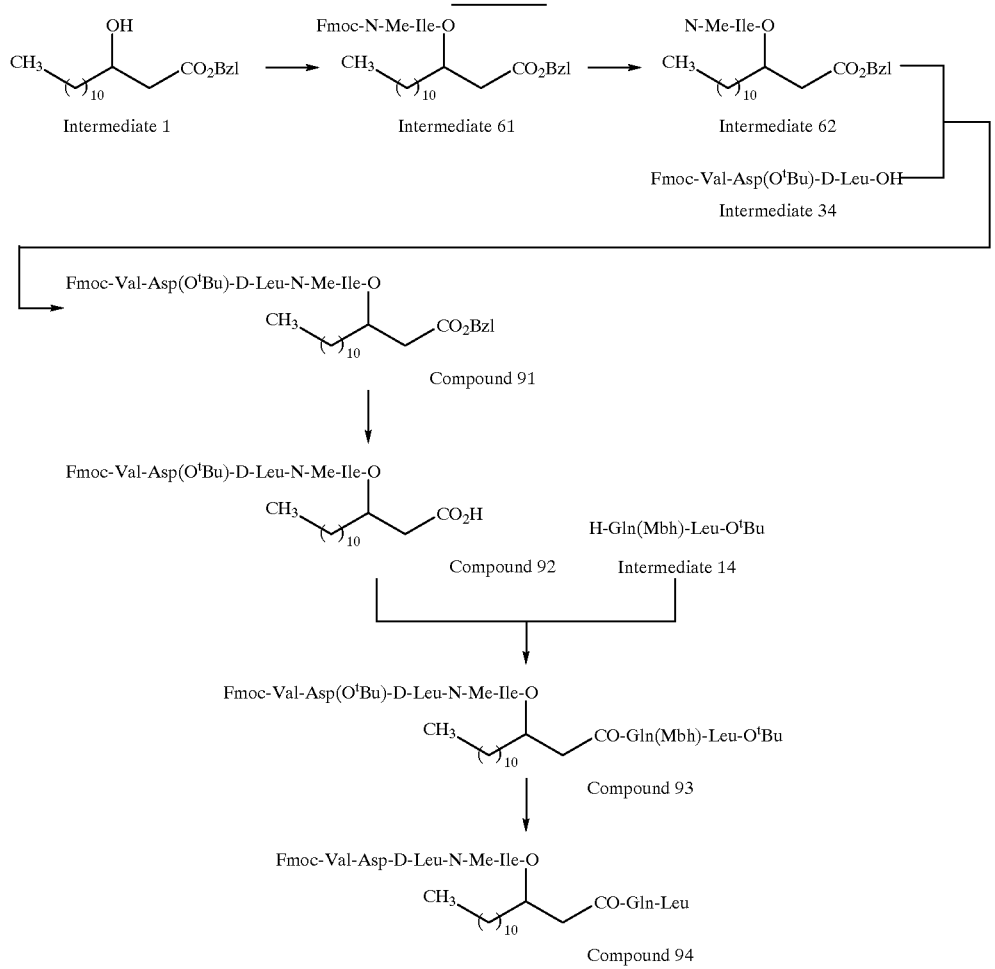
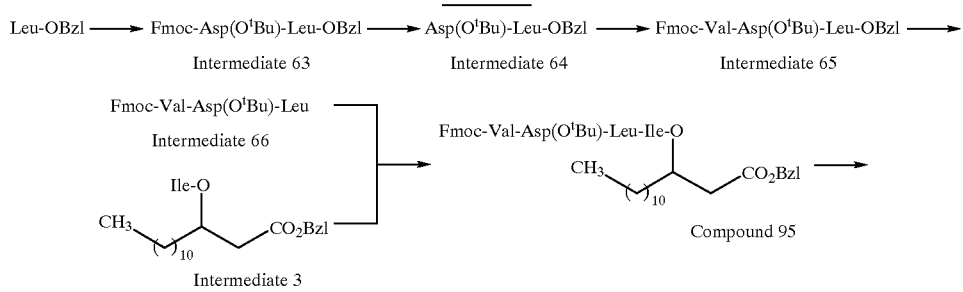

-continued
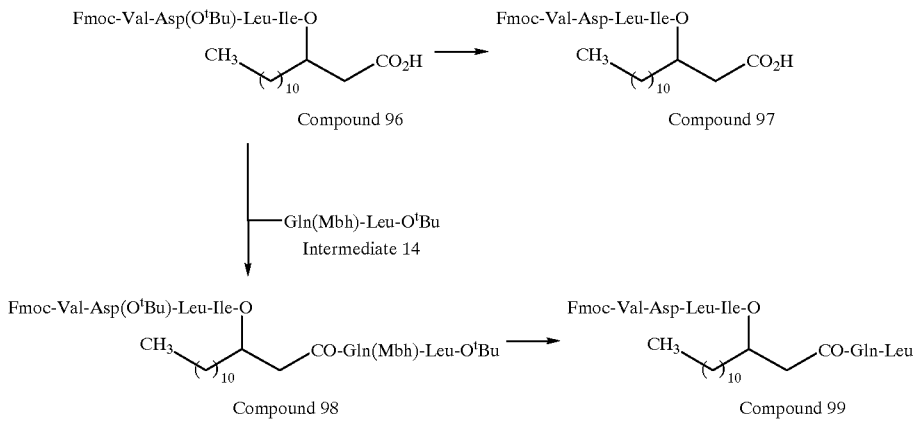
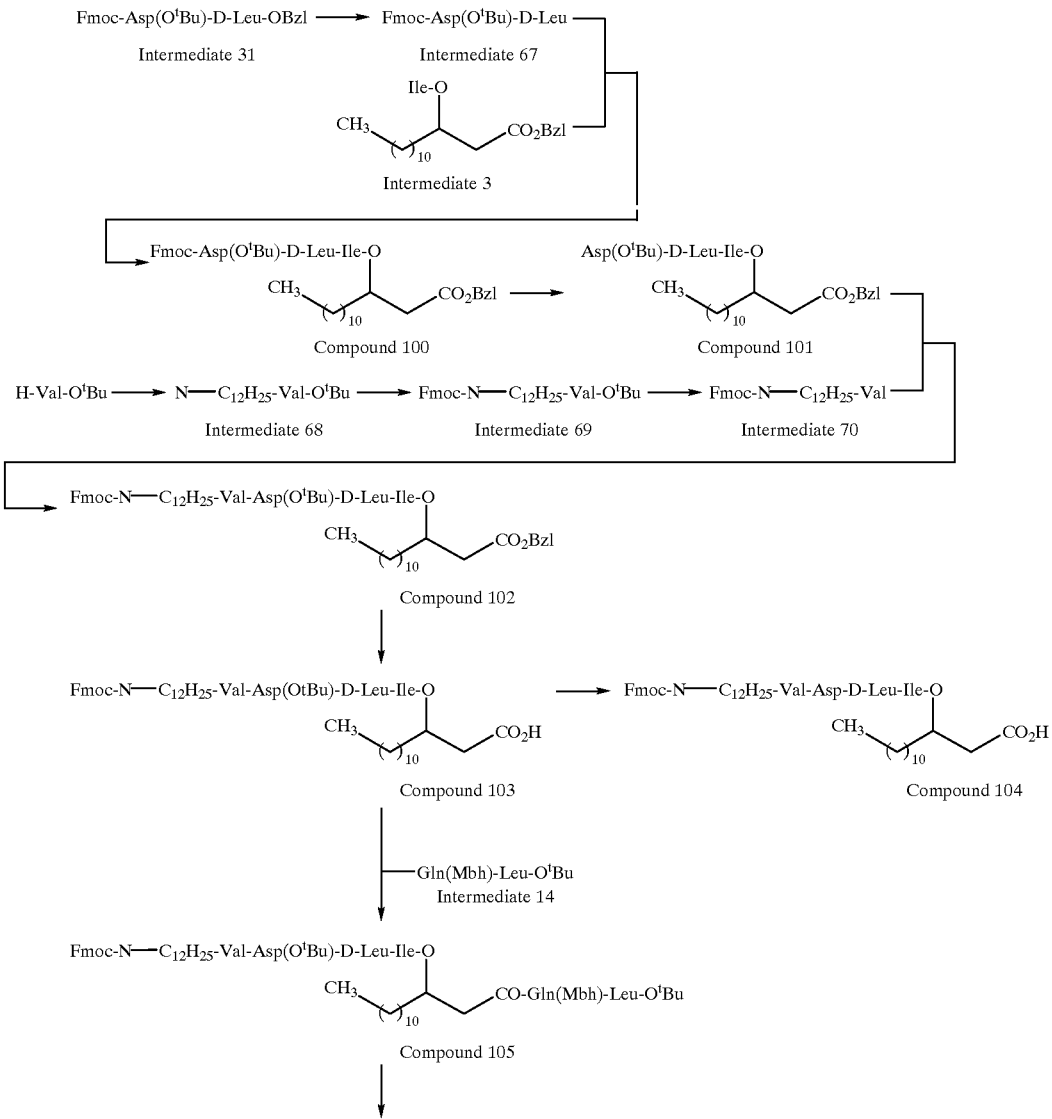
Scheme 22

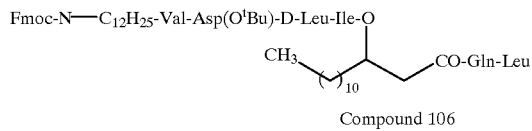
Compound 106
Scheme 23
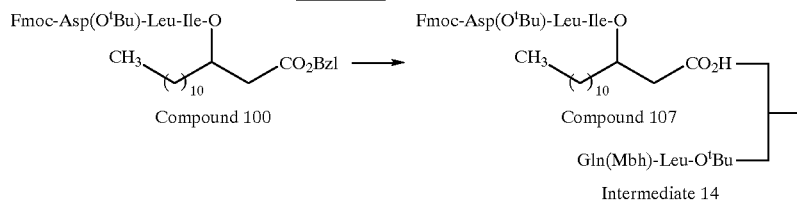
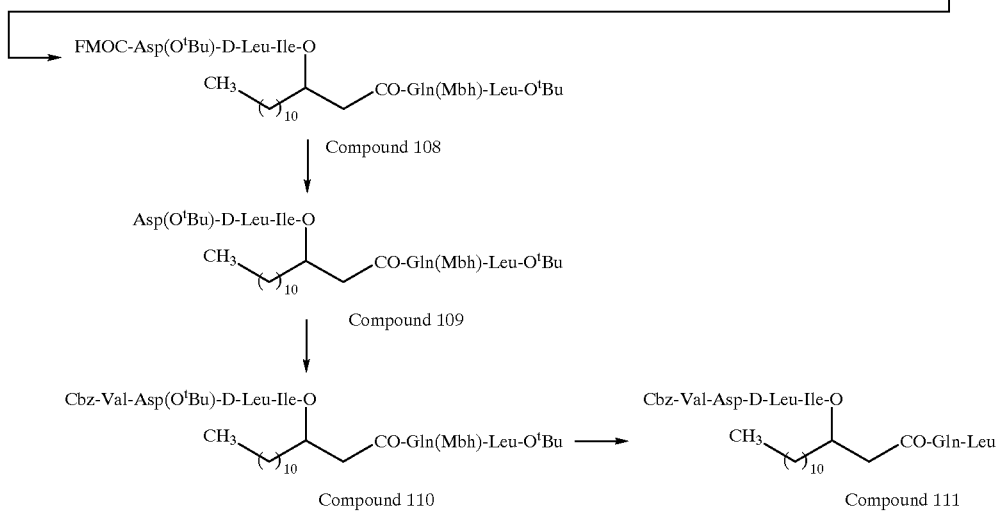
Scheme 24
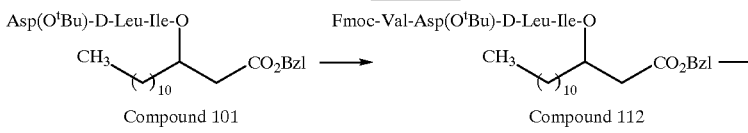
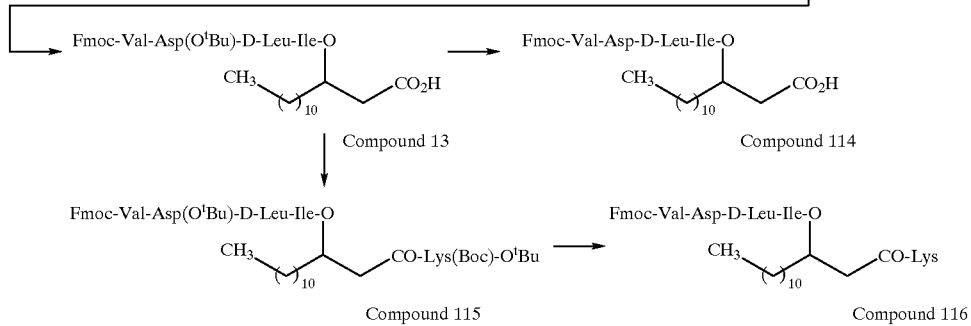

Scheme 25
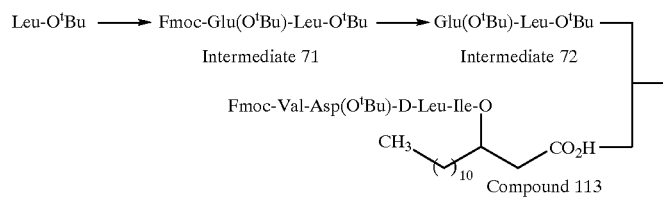
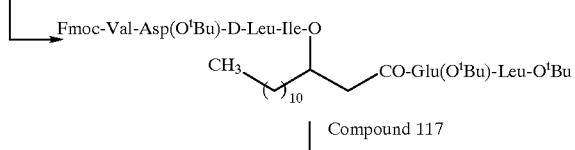
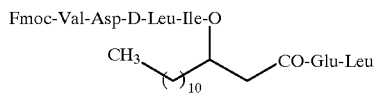
Scheme 26
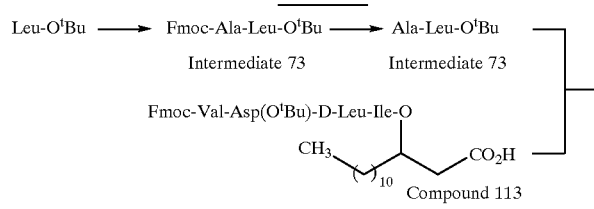
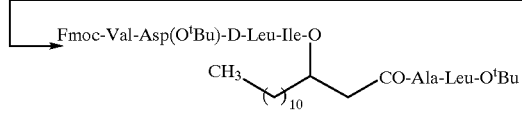
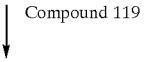
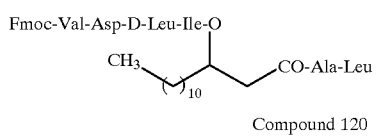

Scheme 27
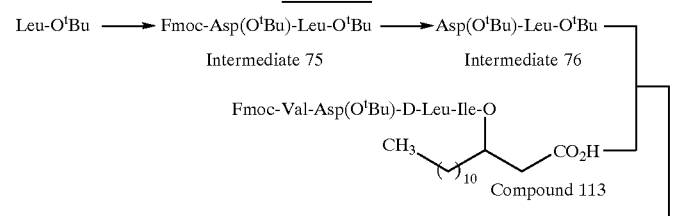
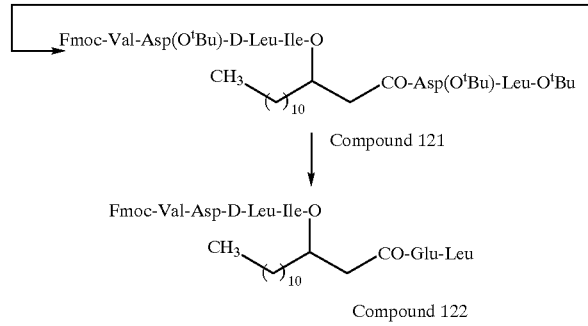
Scheme 28
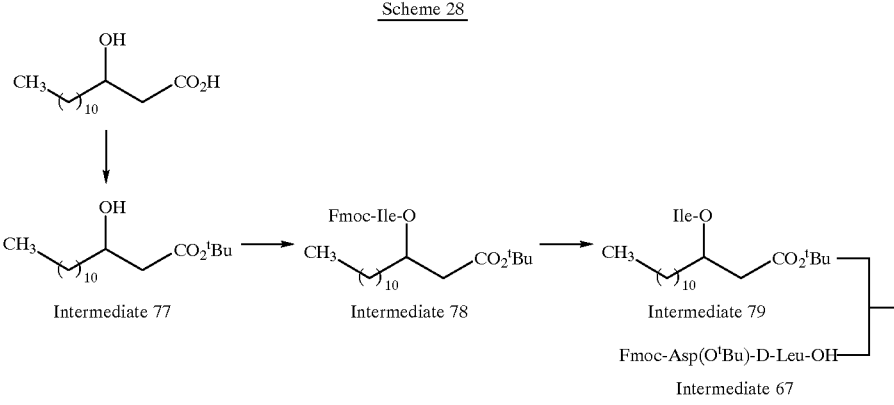
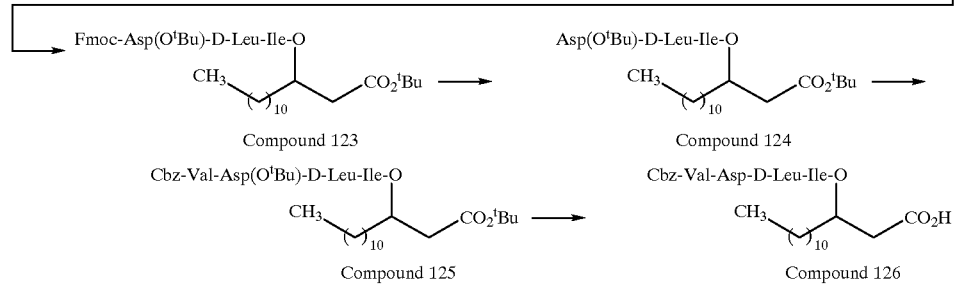

Scheme 29
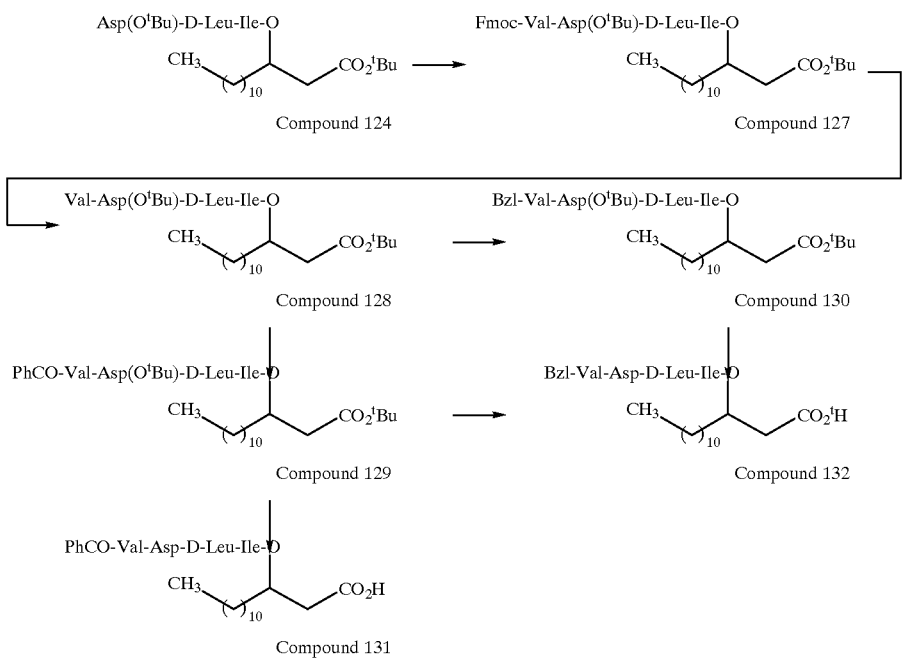
Scheme 30
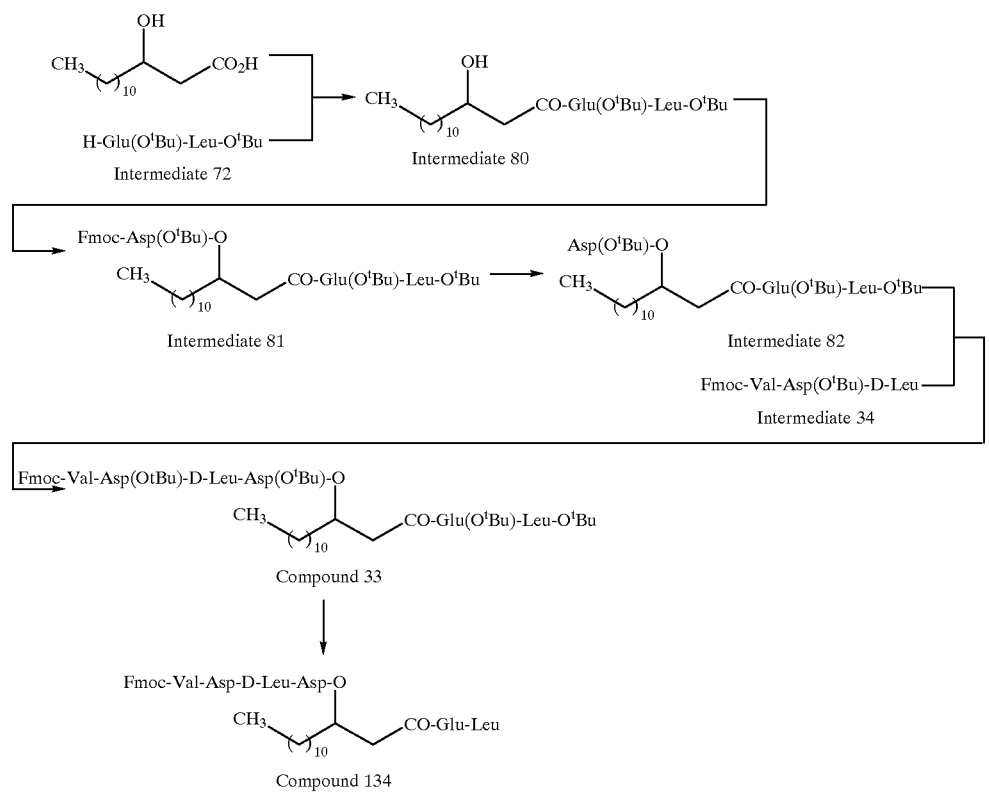

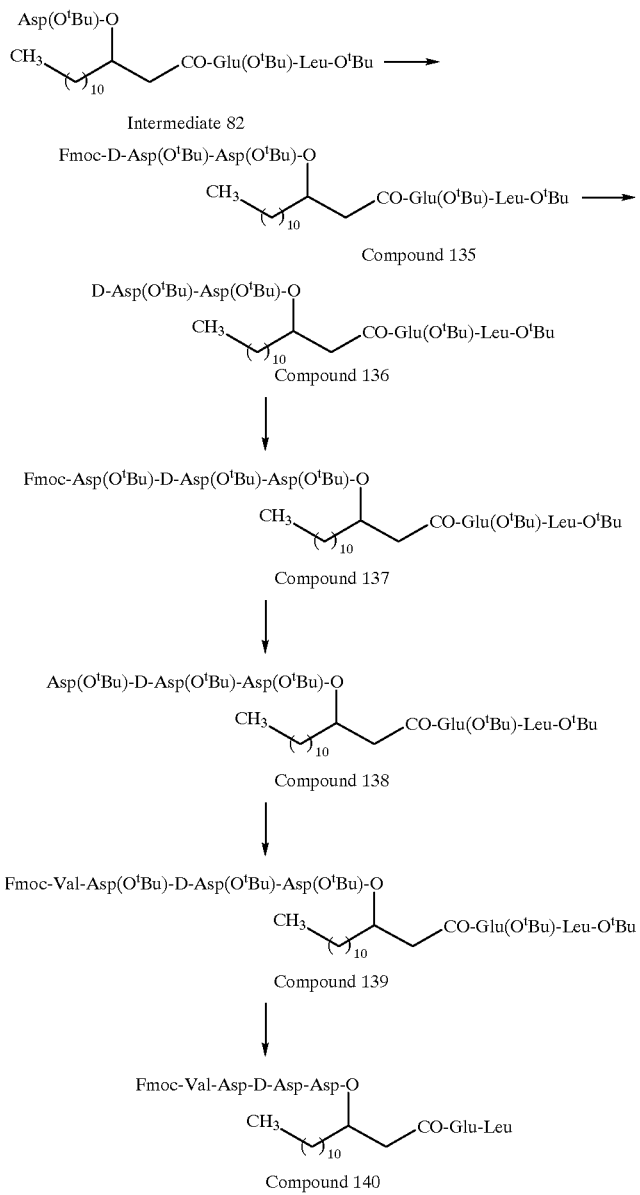
SCHEME 31
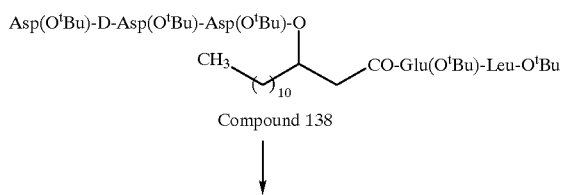
Scheme 32

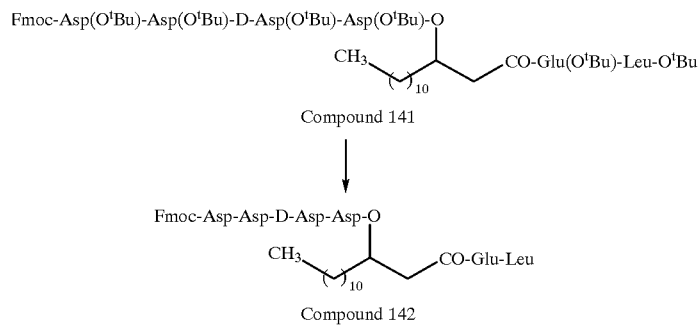
Compound 141
Compound 142
Scheme 33
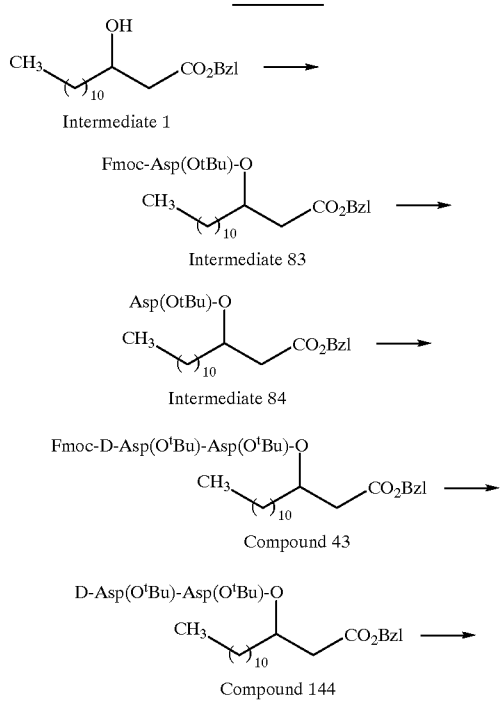
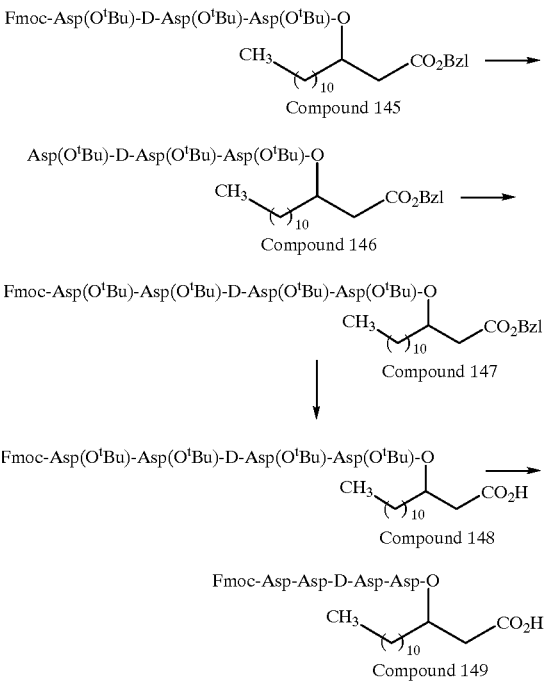
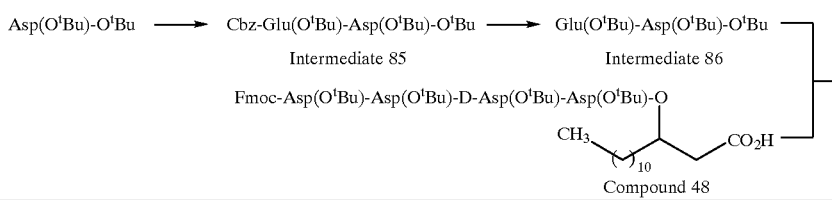
Scheme 34
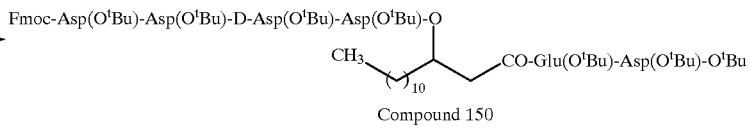

-continued
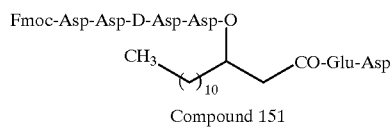
Compound 151
Scheme 35
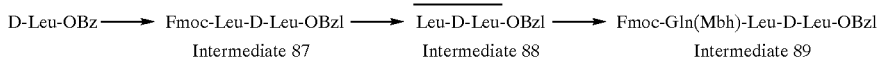
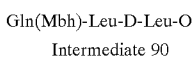
Intermediate 90
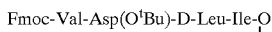
Compound 113
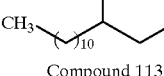
Compound 152
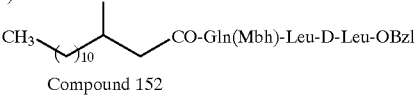
Compound 153
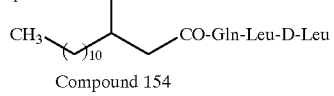
Compound 154
Scheme 36
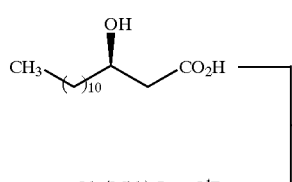
Intermediate 72
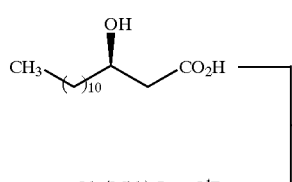
Intermediate 91

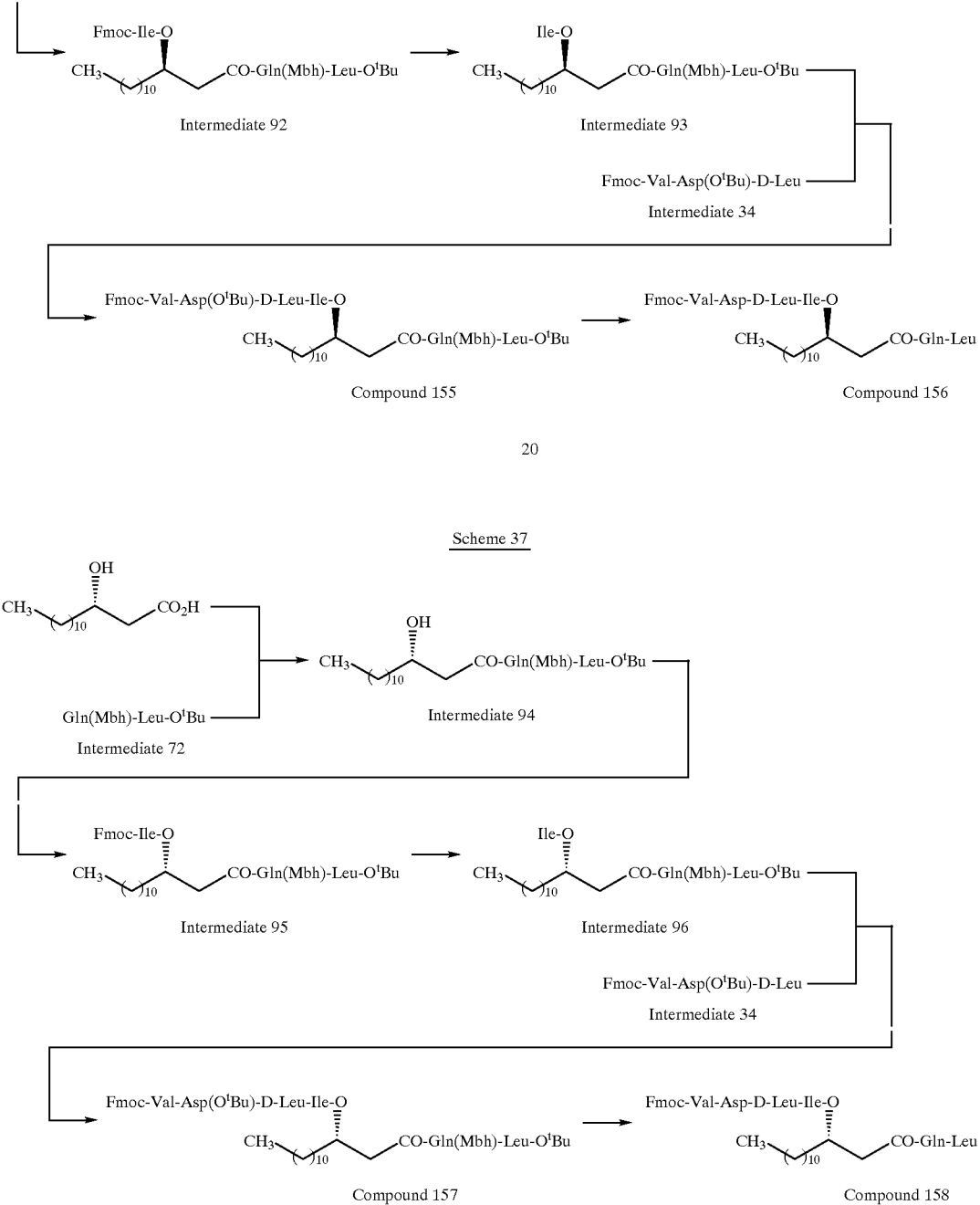

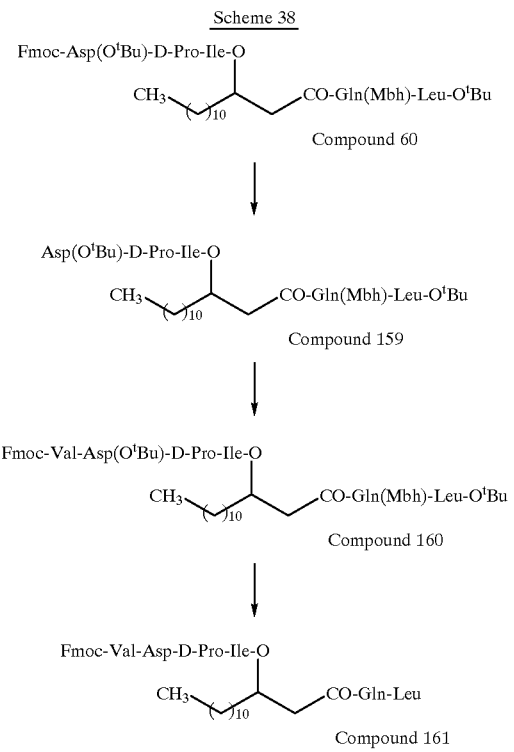

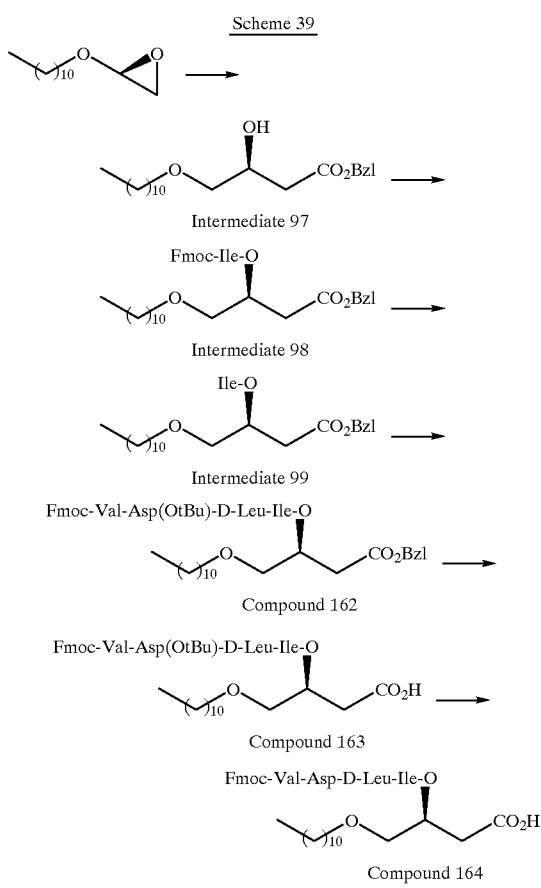

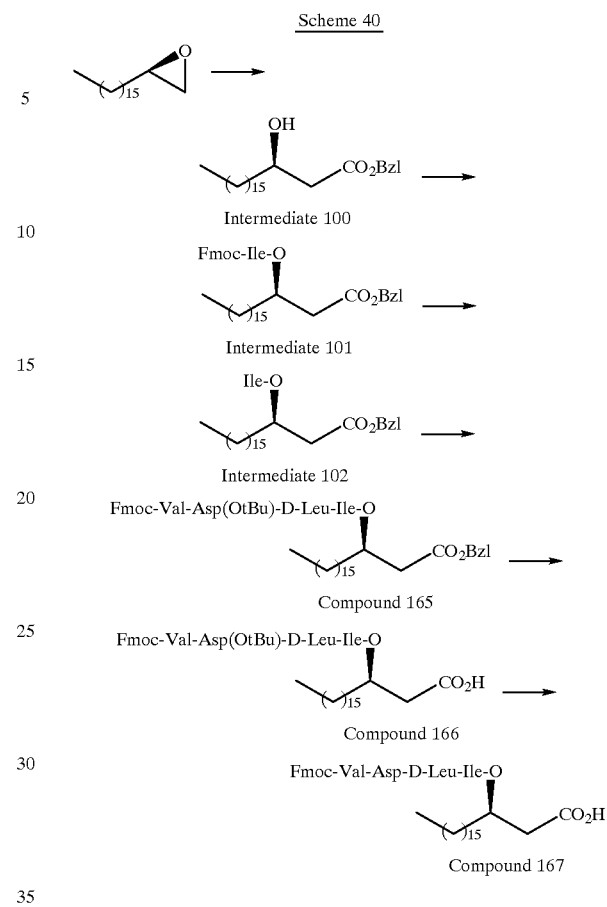

Test Example

It will be explained below that the depsipeptides of the invention show a promoting activity on the producibility of apolipoprotein E in Hep G2 cells, together with the test procedures used.

First, 1 ml portions of Hep G2 cells at $1 \times 10^5$ cells/ml suspended in Dulbeccols modified Eagle medium (manufactured by Nissui Seiyaku K. K.; hereinafter referred to as "D-MEM medium") containing 10% fetal bovine serum were poured into a 24-well tissue culture plate and cultivation was carried out at 37° C. under atmosphere of a mixed gas composed of 5% carbon dioxide and 95% air. After 3 days, the medium was removed by means of a pipette, 1 ml of fresh D-MEM medium was added and further 10 μl of a methanolic solution of the depsipeptide of the invention at the concentration as shown in Table 1 was added. After 18 hours, the medium was again replaced (D-MEM medium), 10 μl of a methanolic solution of the depsipeptide was added and then cultivation was continued at 37° C. for 8 hours and the supernatant was adopted as a sample solution. The apolipoprotein E produced in the cultured broth was assayed by means of an enzyme immunoassay method.

The composition of the buffers used in the enzyme immunoassay is summarized hereinafter. In this connection, PBS represents phosphate-buffered saline, PBS-T represents phosphate-buffered saline having incorporated Tween 20 and a blocking solution is the phosphate buffer containing the immunosuppressive agent "Block Ace", which is derived from lactoprotein and manufactured by Dainippon Pharmaceutical Co., Ltd.

| PBS (pH 7.2) | |
|---|---|
| KH$_2$PO$_4$ | 0.2 g |
| Na$_2$HPO$_4$·12H$_2$O | 2.9 g |
| NaCl | 8.0 g |
| KCl | 0.2 g |
| Distilled water | q.s. |
| Total | 1000 ml |
| PBS-T (pH 7.2) | |
| KH$_2$PO$_4$ | 0.2 g |
| Na$_2$HPO$_4$·12H$_2$O | 2.9 g |
| NaCl | 8.0 g |
| KCl | 0.2 g |
| Tween 20 | 0.5 g |
| Distilled water | q.s. |
| Total | 1000 ml |
| Blocking solution (pH 7.2) | |
| Block Ace | 250 ml |
| KH$_2$PO$_4$ | 0.2 g |
| Na$_2$HPO$_4$·12H$_2$O | 2.9 g |
| NaCl | 8.0 g |
| KCl | 0.2 g |
| Distilled water | q.s. |
| Total | 1000 ml |

1) Determination of apolipoprotein E

The mouse antihuman apolipoprotein E monoclonal antibody (manufactured by BYOSIS, S. A., France) was dissolved in a 0.05M aqueous sodium hydrogencarbonate solution (pH 9.5) at a concentration of 5 µl/ml. 50 µl of this solution was poured in portions into a Nunk immunoplate, which was then allowed to stand at 4° C. for 16 hours. After washing three times with 300 µl of PBS, 300 µl of the blocking solution was added and the mixture was allowed to stand at 37° C. for 2 hours and then at 4° C. for 16 hours.

It was again washed three times with 300 µl of PBS, 50 µl of the above sample solution (the medium for Hep G2 cells) was added and the mixture was allowed to stand at room temperature for 2 hours. After washing three times with 300 µl of PBS-T, 50 µl of a 3000-fold diluted solution (10% aqueous Block Ace solution) of goat anti-apolipoprotein E polyclonal antibody (manufactured by Chemicon Co., Ltd., U.S.A.) was added and the mixture was allowed to stand at room temperature for 2 hours. The mixture was washed three times with 300 µl of PBS-T, a 5000-fold diluted solution (a 10% aqueous solution of Block Ace) of a peroxidase-labeled anti-goat IgG polyclonal antibody (manufactured by Bindingsite Co., Ltd., U. K.) was added and the mixture was allowed to stand at room temperature for 2 hours. After washing five times with 300 µl of PBS-T, 100 µl of a coloring solution (Composition: 0.1M potassium citrate (pH 4.5) 1 ml, 30% aqueous hydrogen peroxide 0.4 µl, orthophenylenediamine 1 mg) was added and the mixture was allowed to stand as such for 2 minutes. The reaction was discontinued by the addition of 100 µl of 2N sulfuric acid and absorbance at 490 nm was measured using absorbance at 650 nm as a control. An absolute amount of apolipoprotein E in the present depsipeptide was determined upon a calibration curve drawn up when a commercially available apolipoprotein E (Chemicon Co., Ltd., U.S.A.) was used as a standard.

In this Test Example, the same procedure as described above was carried out except that methanol was added instead of the methanolic solution of the depsipeptide to measure an apolipoprotein E amount, which was used as a control. A relative apolipoprotein E amount by the present depsipeptide was represented in terms of a relative value (%) when the control was defined as 100.

As shown in Table 1, it was proved that the depsipeptides of the invention have a potent activity of promoting producibility of apolipoprotein E at 1, 5 or 10 µM.

TABLE 1

| Compound | Conc. (µM) | Relative amount of apolipoprotein E (%) |
|---|---|---|
| Compound 5 | 10 | 168 |
| Compound 7 | 10 | 168 |
| Compound 9 | 5 | 306 |
| Compound 11 | 5 | 364 |
| Compound 13 | 5 | 458 |
| Compound 15 | 5 | 390 |
| Compound 33 | 10 | 288 |
| Compound 39 | 10 | 665 |
| Compound 41 | 1 | 192 |
| Compound 44 | 1 | 194 |
| Compound 46 | 1 | 130 |
| Compound 49 | 1 | 277 |
| Compound 56 | 1 | 185 |
| Compound 59 | 1 | 135 |
| Compound 61 | 1 | 144 |
| Compound 63 | 1 | 370 |
| Compound 64 | 1 | 155 |
| Compound 67 | 1 | 132 |
| Compound 69 | 1 | 173 |
| Compound 71 | 1 | 196 |
| Compound 75 | 1 | 221 |
| Compound 77 | 1 | 216 |
| Compound 83 | 1 | 204 |
| Compound 85 | 1 | 201 |
| Compound 86 | 1 | 153 |
| Compound 90 | 1 | 244 |
| Compound 94 | 1 | 130 |
| Compound 99 | 1 | 172 |
| Compound 111 | 1 | 207 |
| Compound 114 | 1 | 330 |
| Compound 116 | 1 | 228 |
| Compound 118 | 1 | 239 |
| Compound 122 | 1 | 254 |
| Compound 126 | 1 | 219 |
| Compound 131 | 1 | 153 |
| Compound 134 | 1 | 197 |
| Compound 140 | 1 | 199 |
| Compound 142 | 1 | 178 |
| Compound 149 | 1 | 221 |
| Compound 151 | 1 | 241 |
| Compound 154 | 1 | 273 |
| Compound 156 | 1 | 268 |
| Compound 161 | 1 | 177 |
| Compound 164 | 1 | 210 |
| Compound 167 | 1 | 132 |
| Control | 0 | 100 |

Preparation Examples

Examples of the pharmaceutical preparations containing as an active ingredient the depsipeptide of the invention will be given below.

Preparation Example 1: Tablets (per tablet)

| Compound (39) | 20 mg |
|---|---|
| Magnesium silicate | 20 mg |
| Lactose | 98.5 mg |
| Hydroxypropylcellulose | 7.5 mg |
| Magnesium stearate | 1 mg |
| Hydrogenated vegetable oil | 3 mg |
| Total | 150 mg |

Compound (39), magnesium silicate and lactose were admixed and kneaded with an alcoholic solution of hydroxypropylcellulose and then granulated to appropriate particle size, dried, and sized. Then, magnesium stearate and hydrogenated vegetable oil were added and blended to form uniform granules. The granules were then prepared to tablets, each having a diameter of 7.0 mm, a weight of 150 mg and a hardness of 6 kg, by means of a rotary tableting machine.

Preparation Example 2: Granules

| Compound (39) | 10 mg |
| Magnesium oxide | 40 mg |
| Calcium hydrogenphosphate | 38 mg |
| Lactose | 10 mg |
| Hydroxypropylcellulose | 20 mg |

All the materials except for hydroxypropylcellulose were uniformly admixed, kneaded with an alcoholic solution of hydroxypropylcellulose and then granulated by means of an extrusion granulation machine and dried to form granules. The granules were sized so as to pass through a 12 mesh sieve and remain on a 48 mesh sieve, thereby forming granules.

Preparation Example 3: Syrups

| Compound (39) | 1.000 g |
| Sucrose | 30.000 g |
| D-Sorbitol 70 w/v % | 25.000 g |
| Ethyl paraoxybenzoate | 0.030 g |
| Propyl paraoxybenzoate | 0.015 g |
| Flavoring agent | 0.200 g |
| Glycerol | 0.150 g |
| 96% Ethanol | 0.500 g |
| Purified water | q.s. |
| Total | 100 ml |

Sucrose, D-sorbitol, ethyl paraoxybenzoate, propyl paraoxybenzoate and Compound (39) were dissolved in 60 g of purified water (warm water). After cooling, a solution of flavoring agent in glycerol and ethanol was added and then to the mixture was added purified water to make up a volume to 100 ml.

Preparation Example 4: Injections

| Sodium salt of Compound (13) | 10.0 mg |
| Sodium chloride | 81.0 mg |
| Sodium hydrogencarbonate | 8.40 mg |
| Distilled water for injection | q.s. |
| Total | 10.0 ml |

Sodium hydrogencarbonate, sodium chloride and the sodium salt of Compound (13) were dissolved in distilled water to make up a total amount to 10.0 ml.

Preparation Example 5: Suppositories

| Compound (39) | 2 g |
| Macrogol 4000 | 20 g |
| Glycerol | 78 g |
| Total | 100 g |

Compound (39) was dissolved in glycerol and then Macrogol 4000 was added and dissolved by warming. Then, the mixture was injected into a suppository die and solidified by cooling to prepare suppositories, each weighing 1.5 g.

INDUSTRIAL APPLICABILITY

The depsipeptides of the present invention have an activity of promoting the production of apolipoprotein E. Since apolipoprotein E has an action of repairing neurologic damages, the depsipeptides of the invention are useful as a therapeutic agent for neurologic damages, especially for dementia. Moreover, since apolipoprotein E has an activity of lowering blood cholesterol and triglyceride levels, the present depsipeptides are useful as a therapeutic agent for hyperlipemia.

What is claimed is:

1. A depsipeptide represented by the formula (1):

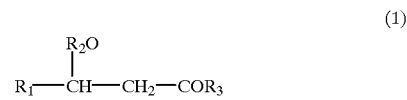

(1)

$R_1$ is a straight or branched alkyl group of 5–20 carbon atoms or a straight or branched alkoxymethyl group of 5–15 carbon atoms;

$R_2$ is —A—B, —A—B—W, —A—B—W—D or —A—B—W—D—E, $R_3$ is a hydroxyl group, a lower alkoxy group, a benzyloxy group, —Z, —Z—G or —Z—G—J, said A, B, D, E, G and J independently of each other are an amino acid selected from alanine, valine, leucine, isoleucine, serine, threonine, lysine, hydroxylysine, arginine, cysteine, methionine, phenylalanine, tyrosine, tryptophan, histidine, proline, 4-hydroxyproline, piperizine-4-carboxylic acid, homoproline, octahydroindole-2-carboxylic acid, norvaline, norleucine, α-t-butylglycine, cyclohexylglycine, azetidine-2-carboxylic acid, 3-(3-pyridyl)alanine, (3-N-methyl)piperizylalanine, 3-(2-naphthyl)alanine, β-cyclohexylalanine, β-t-butylalanine, 9-anthracenylalanine, α-methylalanine, 2-aminobutanoic acid, aspartic acid, asparagine, glutamic acid and glutamine or an N—($C_1$–$C_4$) alkyl derivative of said amino acid residue;

said W and Z independently of each other are an amino acid selected from aspartic acid, asparagine, glutamic acid, glutamine, alanine, serine or lysine; and wherein a free amino group, a free carboxyl group, ω-carbamido group of said amino acid residue or an N-terminal amino group optionally protected by a protecting group commonly used in peptide chemistry, and when said amino acid residue in the above A, B, D, E, G, J, W and Z is a residue of lysine, hydroxylysine, glutamic acid or aspartic acid, the amino group or carboxyl group is capable of being bound to an adjacent amino acid by a peptide linkage at either the α-position or the ω-position; or a pharmacologically acceptable salt thereof.

2. The depsipeptide of the formula (1) as claimed in claim 1 wherein A, B, D, E, G and J independently Qf each other are alanine, valine, leucine, isoleucine, phenylalanine, tyrosine, proline, β-t-butylalanine or aspartic acid, and W and Z independently of each other are aspartic acid, asparagine, glutamic acid, glutamine, alanine, serine or lysine, or a pharmacologically acceptable salt thereof.

3. The depsipeptide of the formula (1) as claimed in claim 1 wherein A is isoleucine, alanine or aspartic acid, B is leucine, phenylalanine, β-t-butylalanine or aspartic acid, D is valine, phenylalanine, alanine or aspartic acid, E is leucine or alanine, G is leucine or alanine, J is leucine or alanine, W is aspartic acid, glutamic acid, asparagine, glutamine or serine and Z is aspartic acid, glutamic acid, asparagine, glutamine or lysine, or a pharmacologically acceptable salt thereof.

4. The depsipeptide of the formula (1) as claimed in claim 1 wherein A is isoleucine or alanine, B is leucine or alanine, D is valine or alanine, E is leucine, alanine or glutamic acid, G is leucine or alanine, J is leucine or alanine, W is aspartic acid or glutamic acid and Z is glutamin asparagine, glutamic acid, aspartic acid or lysine, or a pharmacologically acceptable salt thereof.

5. The depsipeptide of the formula (1) as claimed in claim 1 wherein A is isoleucine, B is leucine, D is valine, E is leucine, G is leucine, J is leucine, W is aspartic acid or glutamic acid and Z is glutamine, asparagine, glutamic acid, aspartic acid or lysine, or a pharmacologically acceptable salt thereof.

6. A pharmaceutical composition which contains as an active ingredient a depsipeptide as claimed in claim 1 or a pharmacologically acceptable salt thereof; and a pharmaceutically inert ingredient.

7. A method for promoting the production of apolipoprotein E, which comprises administering an amount of the depsipeptide as claimed in claim 1 effective to promote apolipoprotein E production in a patient in need thereof.

8. A method for the treatment of neurologic damages which comprises administering an amount of the depsipeptide as claimed in claim 1 effective to treat neurologic damage in a patient in need thereof.

9. A method for the treatment of dementia which comprises administering an amount of the depsipeptide as claimed in claim 1 effective to treat dementia in a patient in need thereof.

10. A method for the treatment of hyperlipemia which comprises administering an amount of the depsipeptide as claimed in claim 1 effective to treat hyperlipemia in a patient in need thereof.

* * * * *

UNITED STATES PATENT AND TRADEMARK OFFICE
CERTIFICATE OF CORRECTION

PATENT NO.     : 6,255,286 B1
DATED          : July 3, 2001
INVENTOR(S)    : Makoto Yanai et al.

Page 1 of 1

It is certified that error appears in the above-identified patent and that said Letters Patent is hereby corrected as shown below:

Column 76,
Line 15, "formula (1):" should read -- formula (1) wherein: --;
Line 48, "group, ω-carbamido" should read -- group, a free ω-carbamido --;
Line 61, Qf each" should read -- of each --.

Column 77,
Line 14, "glutamin asparagine," should read -- glutamine asparagine --.

Signed and Sealed this

Fifth Day of March, 2002

Attest:

JAMES E. ROGAN
Attesting Officer
Director of the United States Patent and Trademark Office